US008308679B2

(12) United States Patent
Hanson et al.

(10) Patent No.: US 8,308,679 B2
(45) Date of Patent: Nov. 13, 2012

(54) ALIGNMENT SYSTEMS AND METHODS

(75) Inventors: Ian B. Hanson, Northridge, CA (US); Paul F. Bente, IV, South Pasadena, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 256 days.

(21) Appl. No.: 12/649,619

(22) Filed: Dec. 30, 2009

(65) Prior Publication Data

US 2011/0160654 A1   Jun. 30, 2011

(51) Int. Cl.
*A61M 31/00*   (2006.01)
(52) U.S. Cl. ......................................................... 604/67
(58) Field of Classification Search .................... 604/67, 604/131, 151, 506
See application file for complete search history.

(56) References Cited

U.S. PATENT DOCUMENTS

| | | | |
|---|---|---|---|
| 3,994,295 A | 11/1976 | Wulff | |
| 4,633,232 A | 12/1986 | Nelson et al. | |
| 5,628,309 A | 5/1997 | Brown | |
| 5,662,612 A | 9/1997 | Niehoff | |
| 6,283,943 B1 * | 9/2001 | Dy et al. | 604/141 |
| 6,699,218 B2 * | 3/2004 | Flaherty et al. | 604/131 |
| 6,740,059 B2 * | 5/2004 | Flaherty | 604/67 |
| 6,749,587 B2 * | 6/2004 | Flaherty | 604/151 |
| 6,945,760 B2 * | 9/2005 | Gray et al. | 417/417 |
| 7,018,360 B2 * | 3/2006 | Flaherty et al. | 604/123 |
| 7,396,353 B2 | 7/2008 | Lorenzen et al. | |
| 2001/0034506 A1 | 10/2001 | Hirschman et al. | |
| 2001/0041869 A1 | 11/2001 | Causey et al. | |
| 2006/0079765 A1 | 4/2006 | Neer et al. | |
| 2007/0060871 A1 | 3/2007 | Istoc et al. | |
| 2007/0073236 A1 | 3/2007 | Mernoe et al. | |
| 2007/0191770 A1 | 8/2007 | Moberg et al. | |
| 2007/0270744 A1 | 11/2007 | Dacquay et al. | |
| 2008/0051714 A1 | 2/2008 | Moberg et al. | |
| 2008/0097321 A1 | 4/2008 | Mounce et al. | |

(Continued)

FOREIGN PATENT DOCUMENTS

EP   0 937 475   8/1999

(Continued)

OTHER PUBLICATIONS

Search Report dated Jul. 13, 2011 from related PCT application No. PCT/US2010/060895.

(Continued)

*Primary Examiner* — Nicholas Lucchesi
*Assistant Examiner* — Diva K Chander
(74) *Attorney, Agent, or Firm* — Foley & Lardner LLP

(57) ABSTRACT

A delivery system for delivering fluidic media may include a second housing configured to be selectively operatively engaged with and disengaged from a first housing portion adapted to be carried by a user. One of the housing portions may support a reservoir for containing fluidic media and a plunger head moveable within the reservoir. A drive device may be supported by the other of the housing portions for coupling with the reservoir upon the housing portions being operatively engaged. A first interactive element may be supported on the first housing portion for interacting with a second interactive element supported on the second housing portion. Circuitry may be configured to detect an interaction between the interactive elements and configured to provide a signal or a change in state in response to the housing portions being operatively engaged and an interaction between the interactive elements being detected.

48 Claims, 32 Drawing Sheets

U.S. PATENT DOCUMENTS

| | | |
|---|---|---|
| 2008/0097381 A1* | 4/2008 | Moberg et al. ............ 604/506 |
| 2008/0319414 A1 | 12/2008 | Yodfat et al. |
| 2009/0156990 A1 | 6/2009 | Wenger et al. |
| 2009/0182301 A1 | 7/2009 | Bassarab et al. |
| 2009/0259183 A1 | 10/2009 | Chong et al. |
| 2009/0259198 A1 | 10/2009 | Chong et al. |

FOREIGN PATENT DOCUMENTS

| | | |
|---|---|---|
| EP | 2 077 128 B1 | 12/2010 |
| GB | 2 327 151 | 1/1999 |
| JP | 11-339439 | 12/1999 |
| WO | WO-2006/121921 A2 | 11/2006 |
| WO | WO-2008/024812 A2 | 2/2008 |
| WO | WO-2008/024814 A2 | 2/2008 |
| WO | WO-2008/092782 | 8/2008 |
| WO | WO-2008/133702 A1 | 11/2008 |
| WO | WO-2009/033032 A1 | 3/2009 |
| WO | WO-2009/093759 A1 | 7/2009 |
| WO | WO-2009/098291 A1 | 8/2009 |
| WO | WO-2009/125398 A2 | 10/2009 |
| WO | WO-2009/135667 | 11/2009 |
| WO | WO-2009/144726 A1 | 12/2009 |

OTHER PUBLICATIONS

US Office Action dated Oct. 7, 2010 from related U.S. Appl. No. 12/649,172.
Partial Search Report dated Mar. 1, 2011 from related patent application No. PCT/US2010/060892.
Partial Search Report dated Mar. 21, 2011 from related patent application No. PCT/US2010/060895.
Partial Search Report dated Mar. 23, 2011 from related patent application No. PCT/US2010/047590.
US Office Action dated Mar. 3, 2011 from related U.S. Appl. No. 12/649,172.
International Search Report and Written Opinion from related patent application No. PCT/US2010/062414.
IPRP dated Mar. 6, 2012 from related PCT/US2010/047590 application.

* cited by examiner

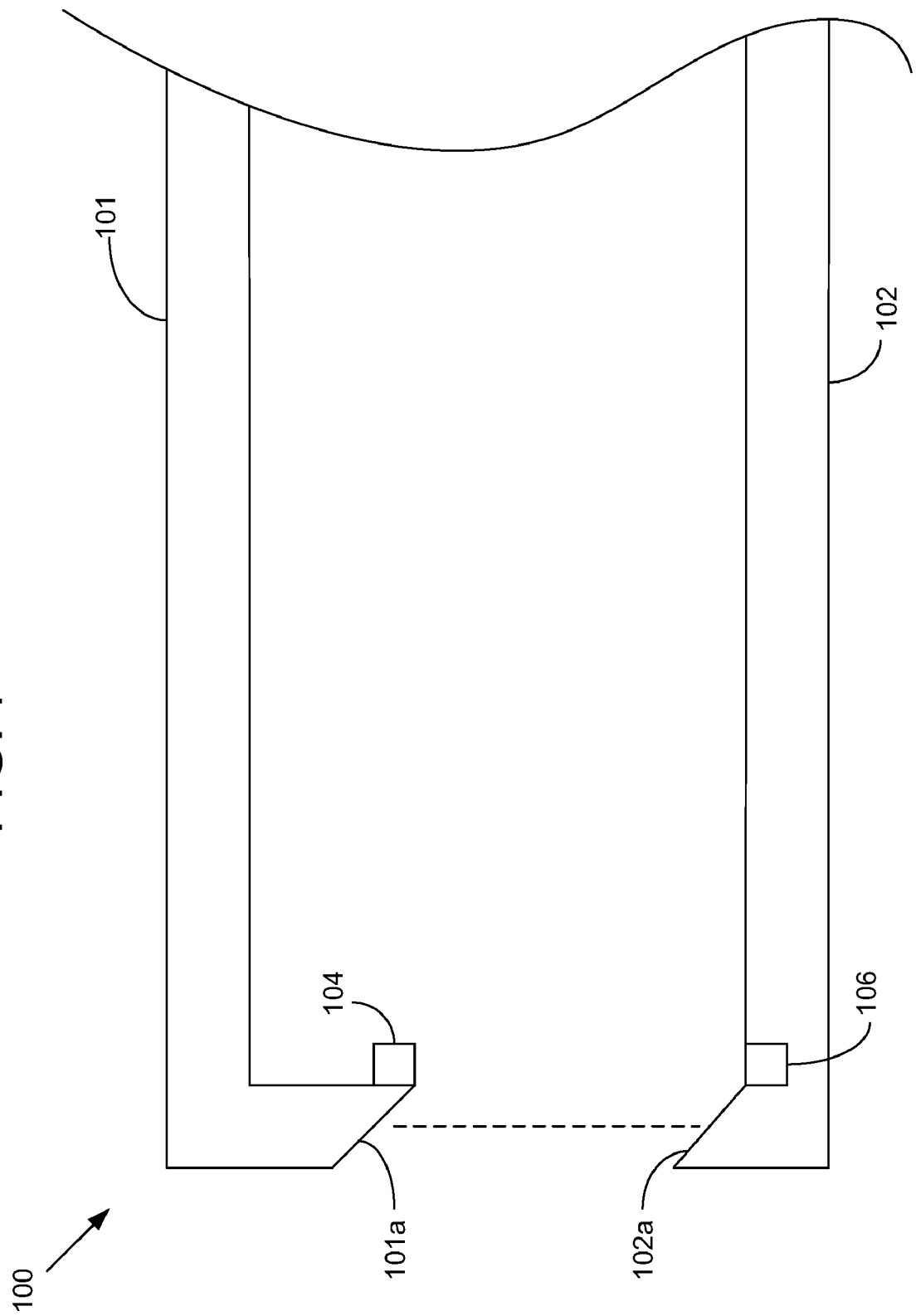

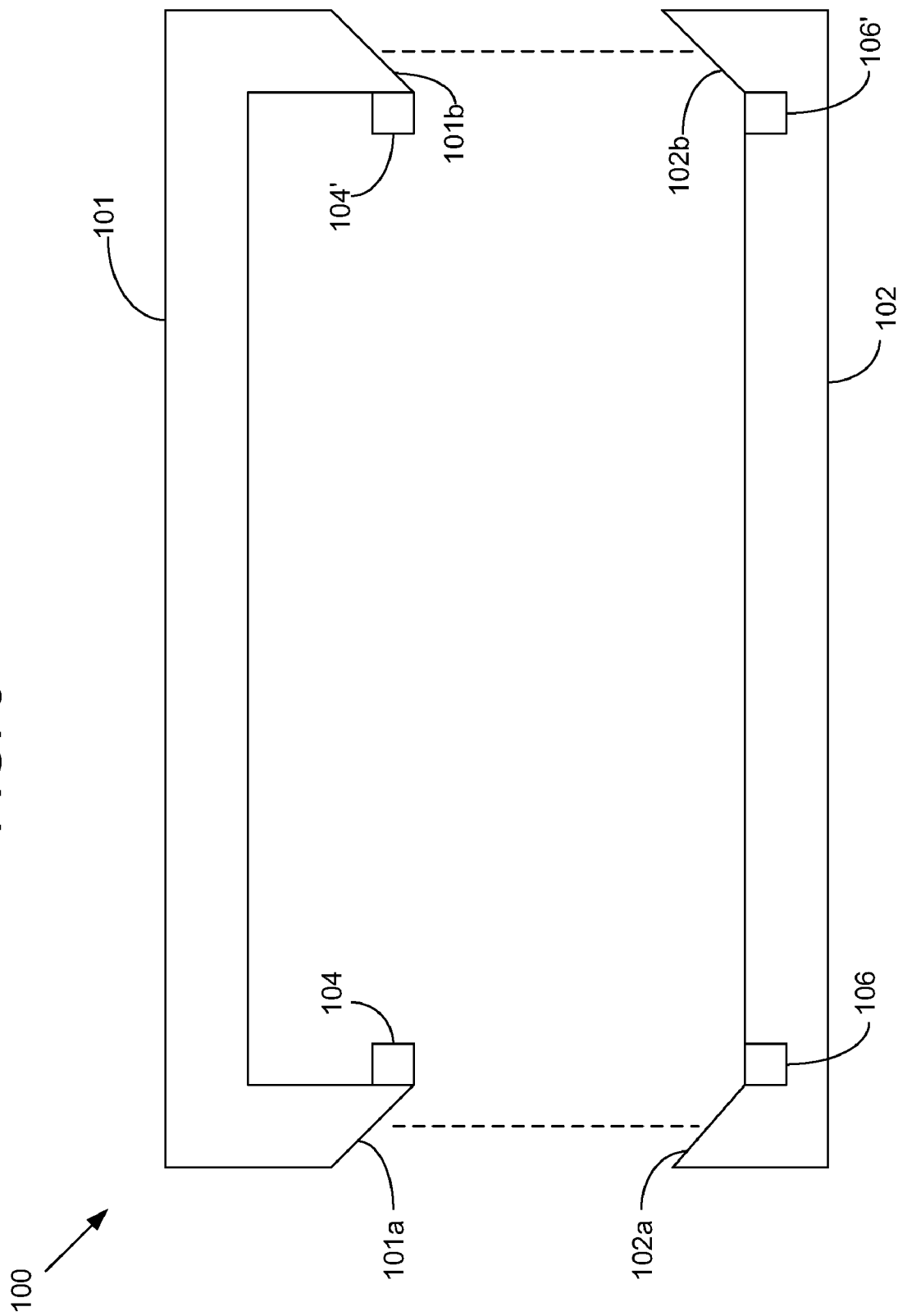

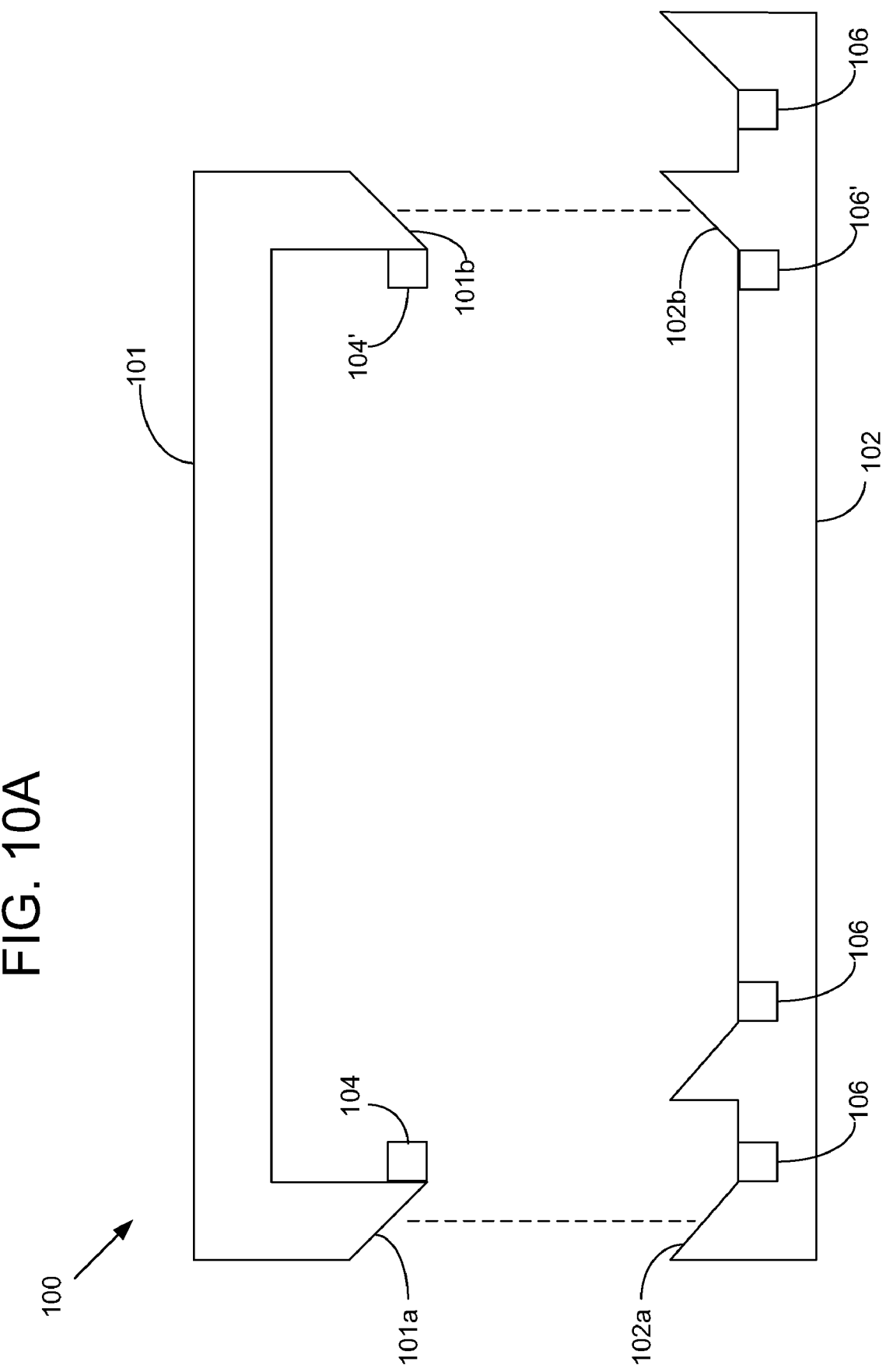

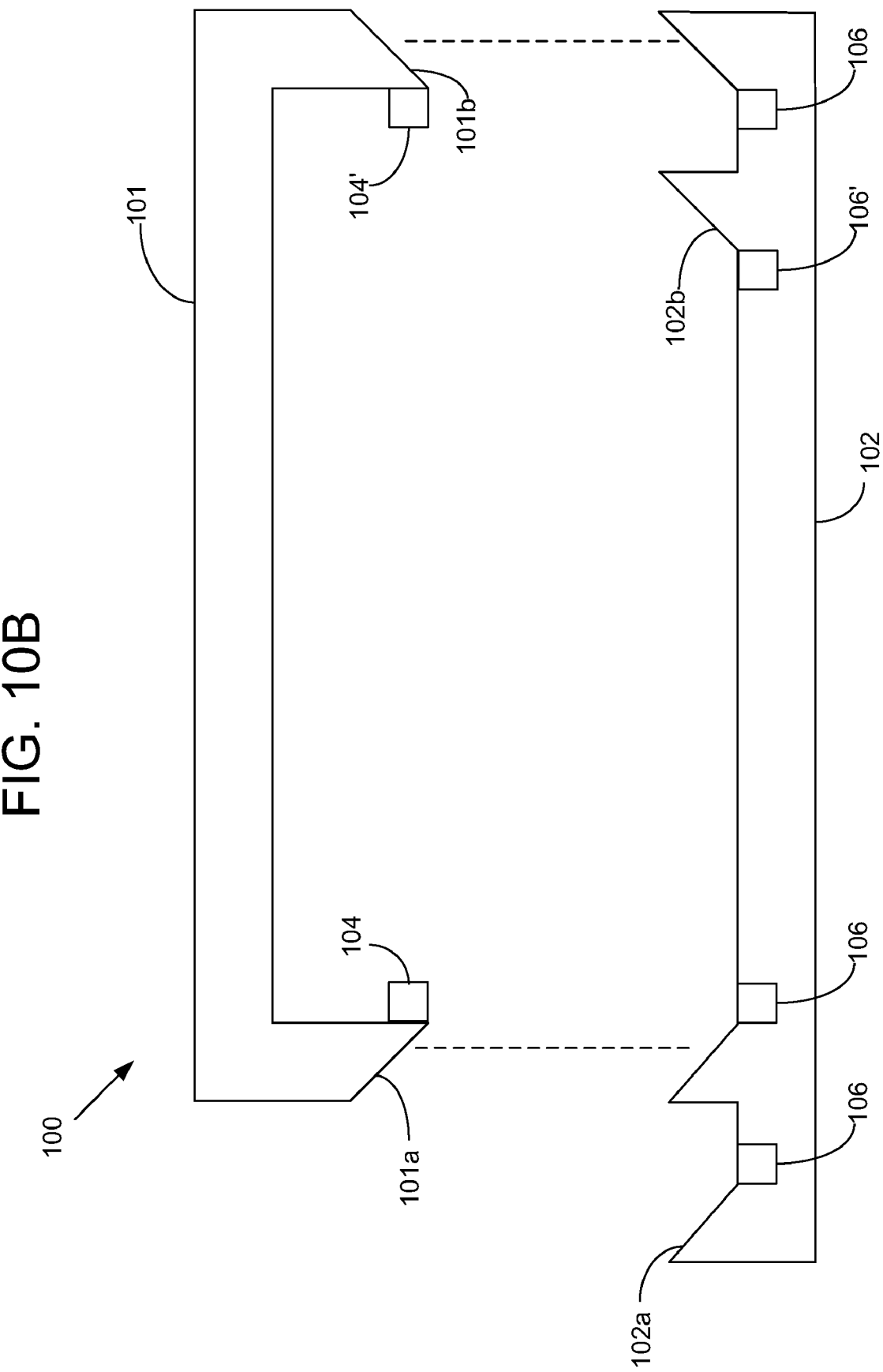

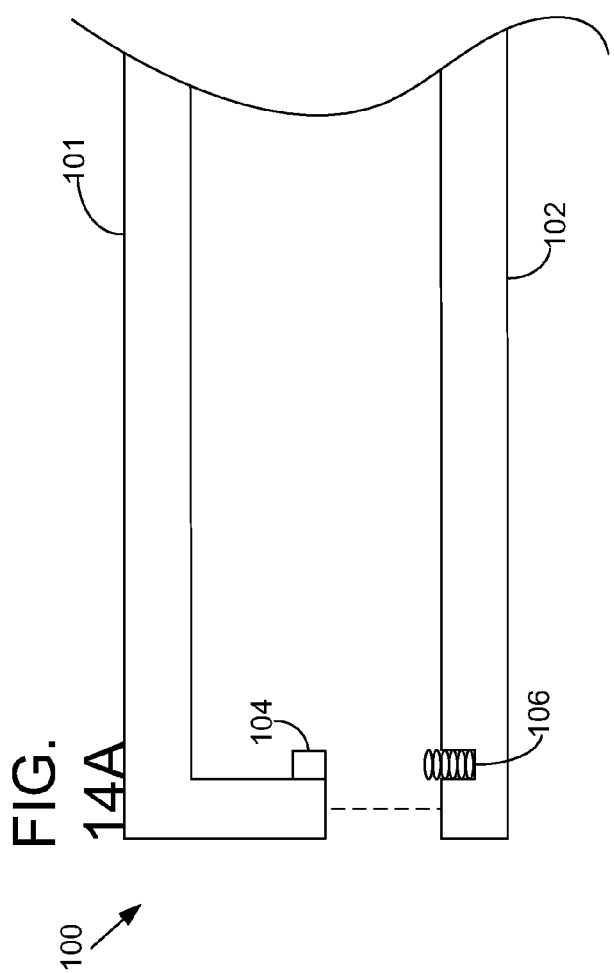
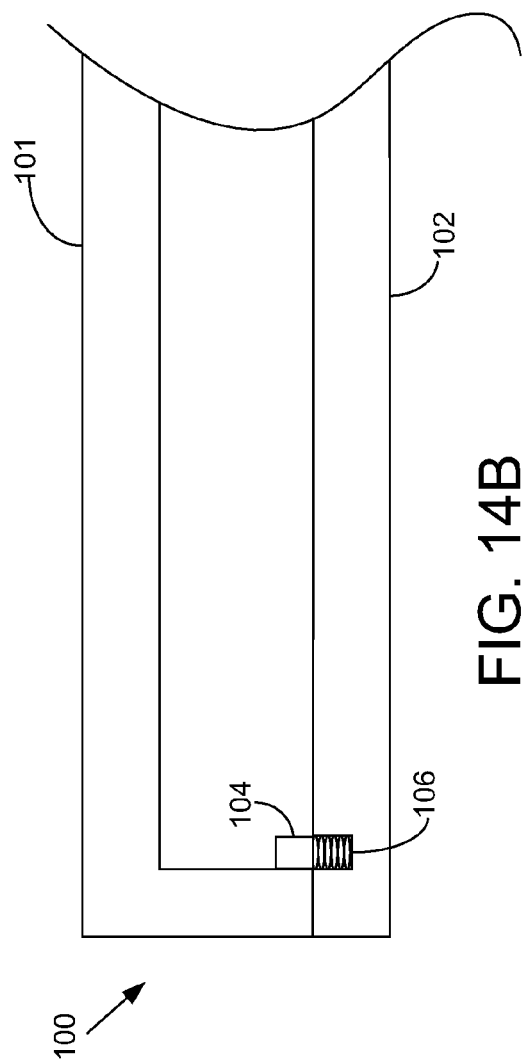

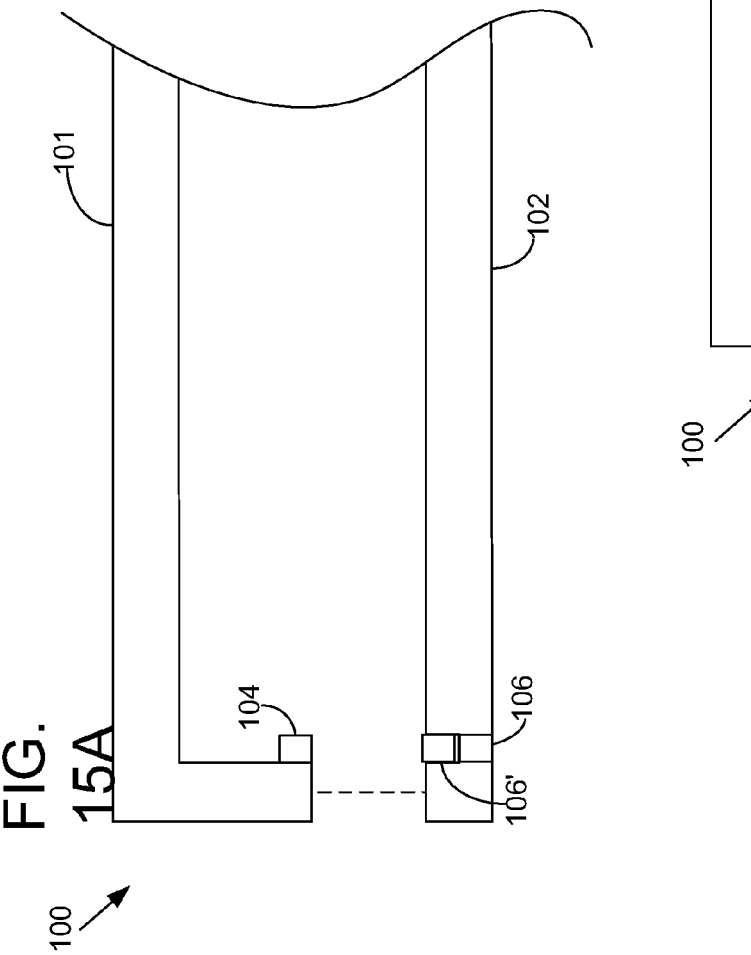
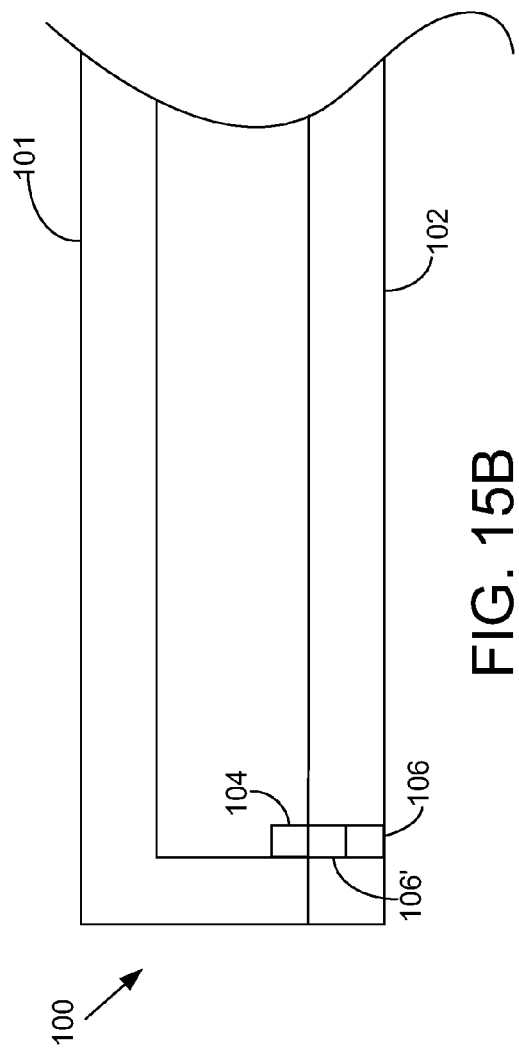

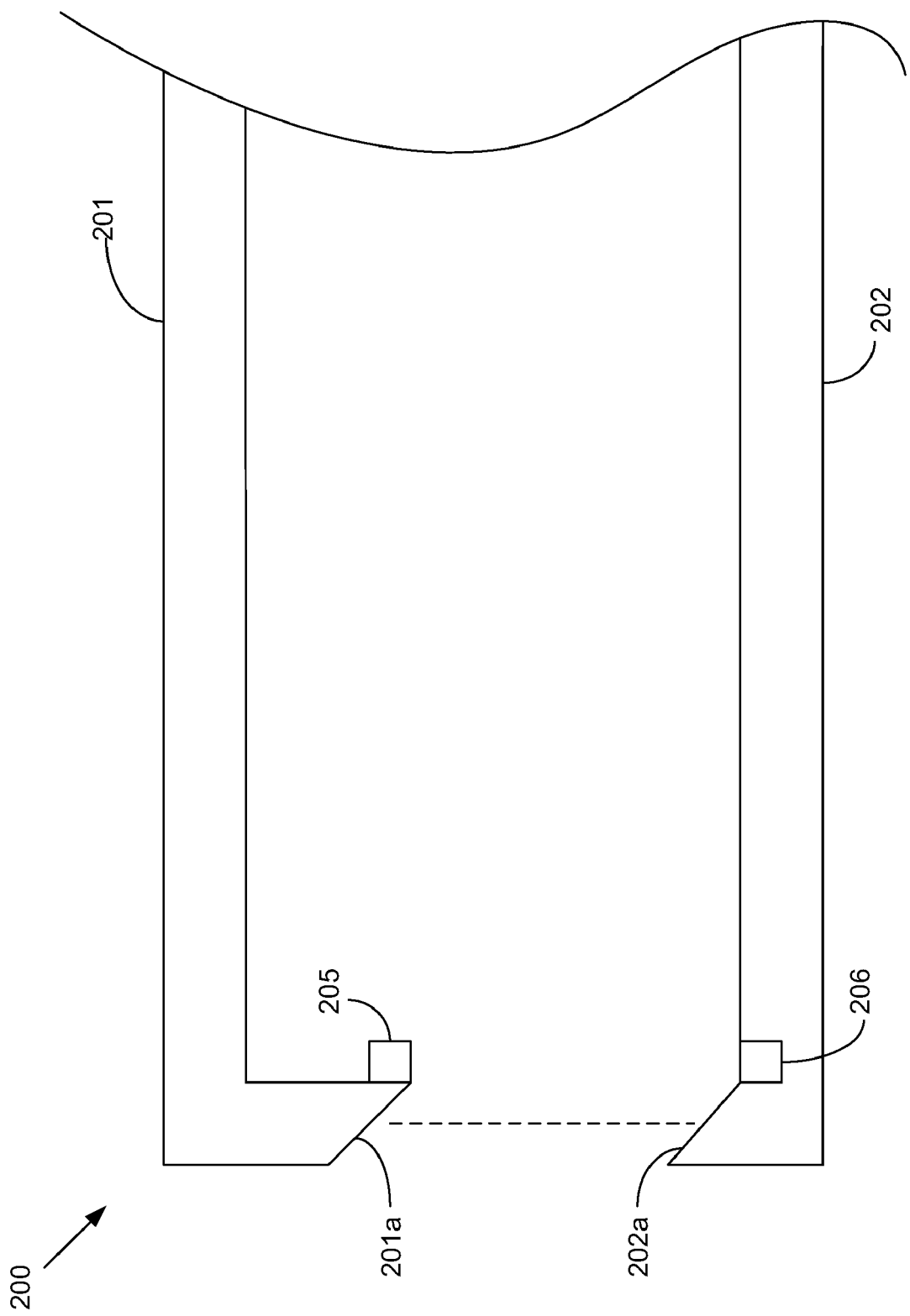

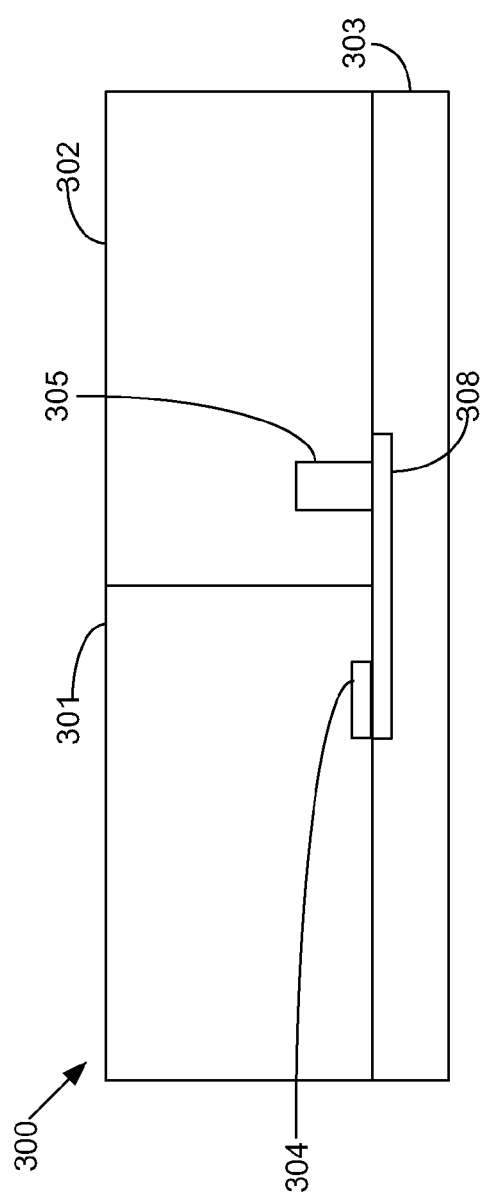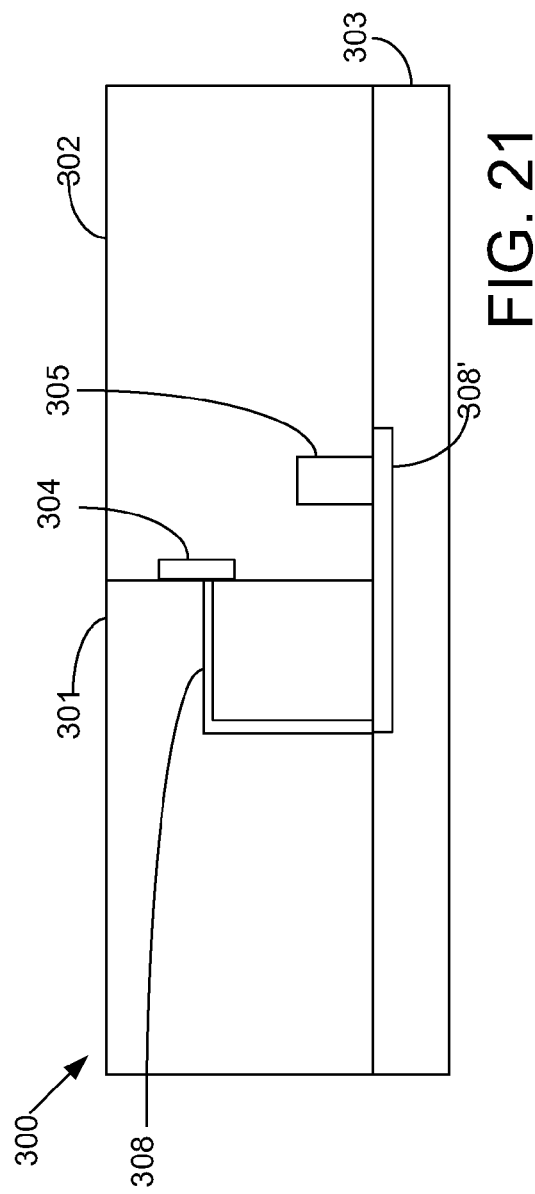

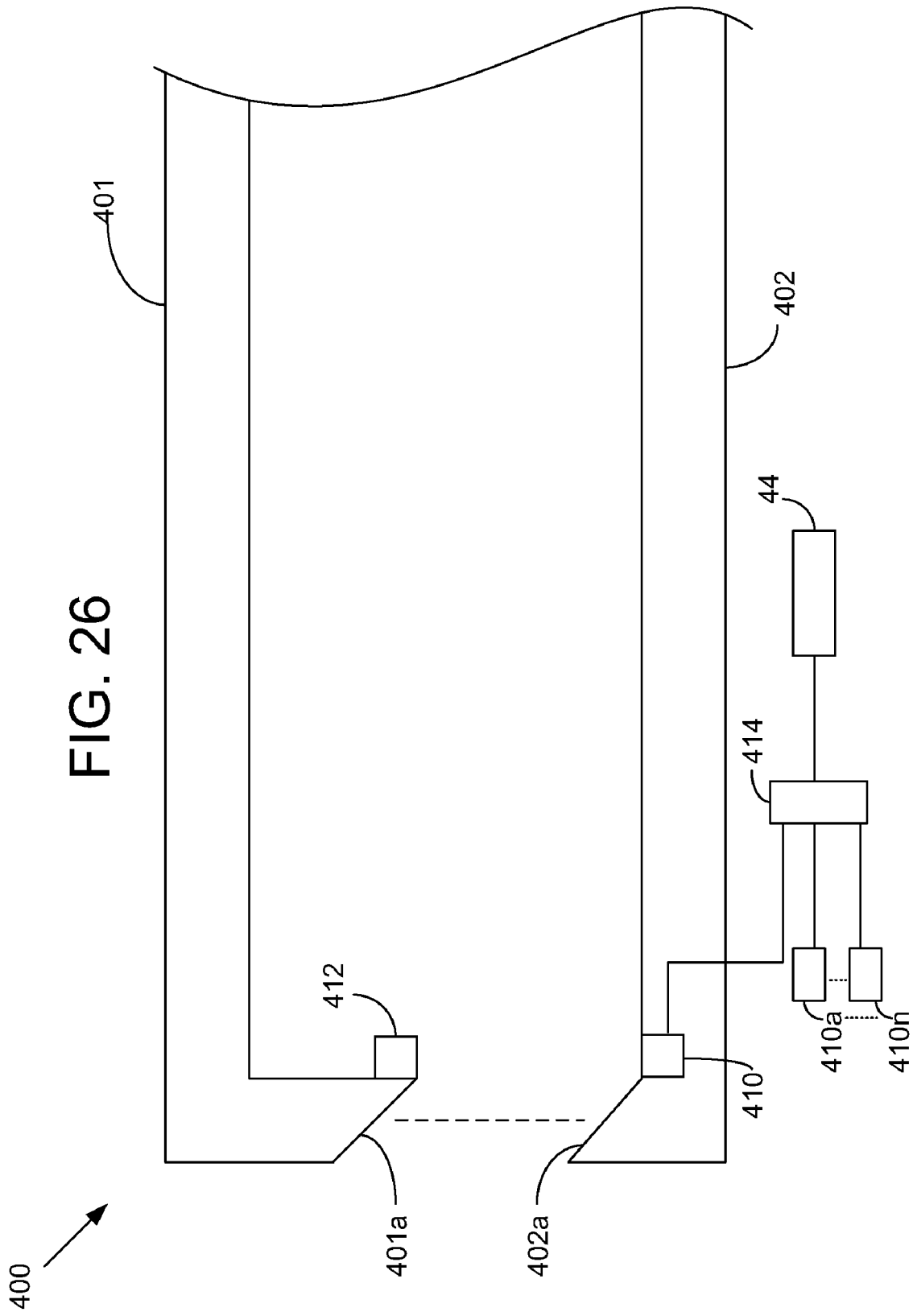

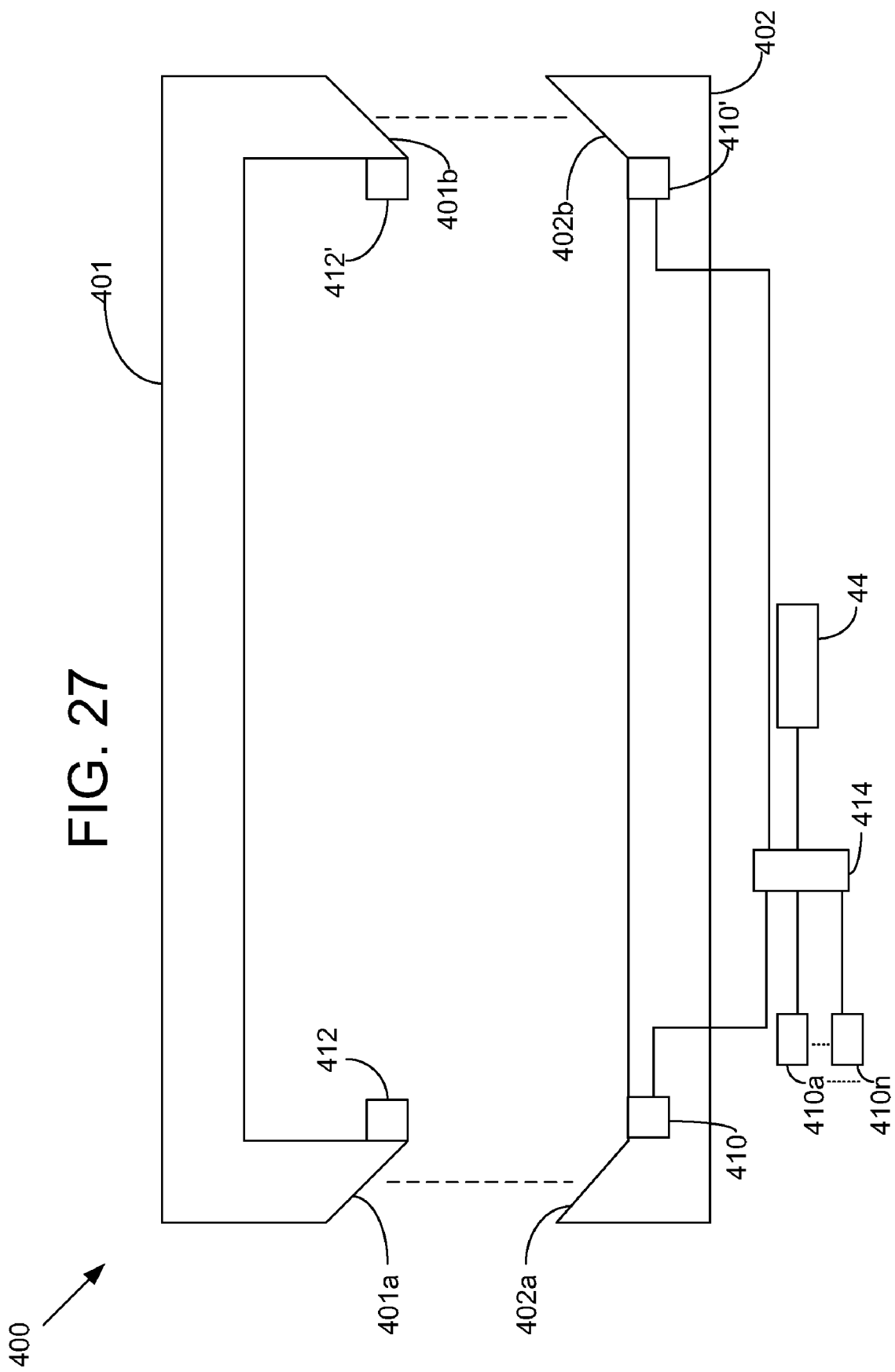

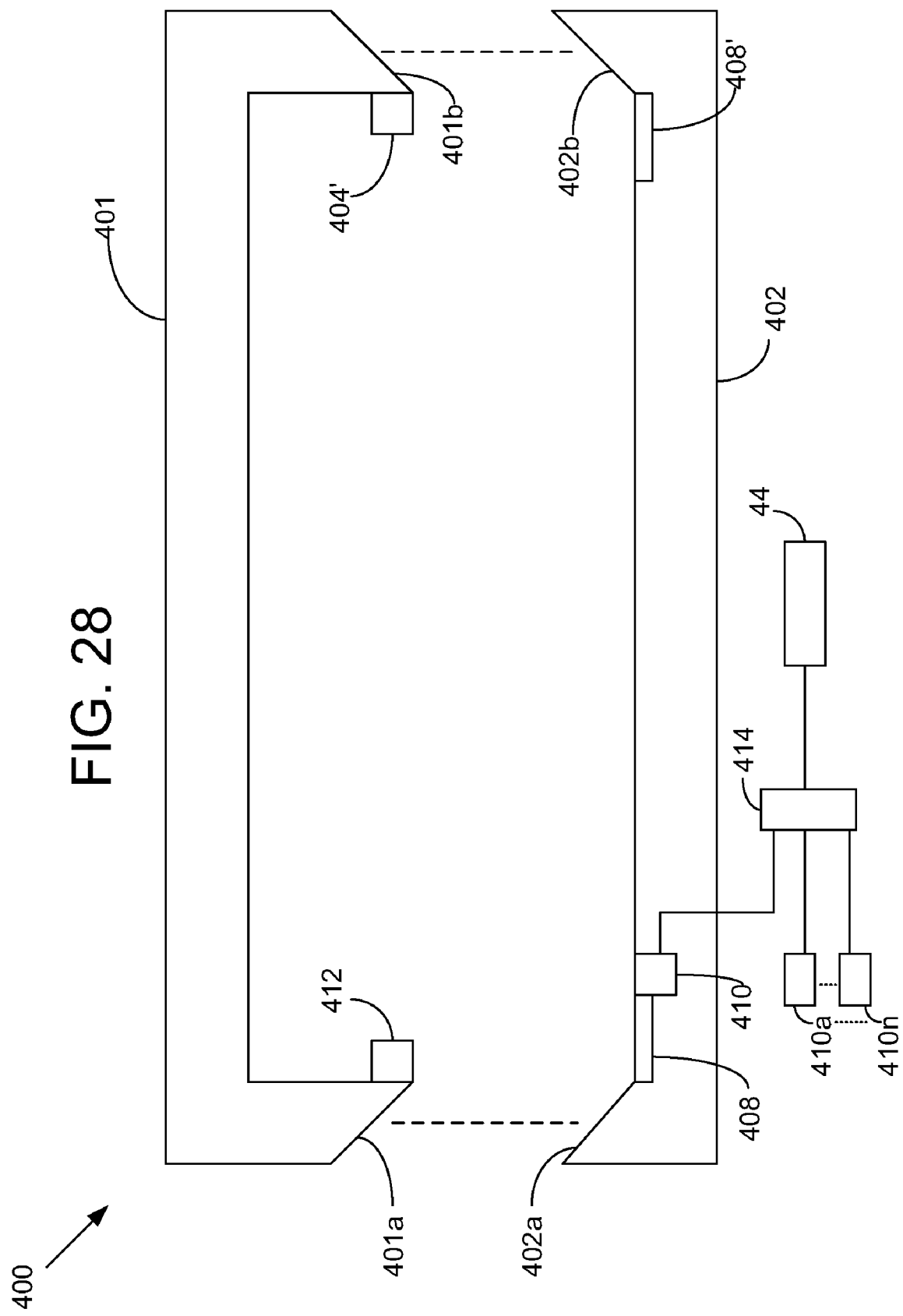

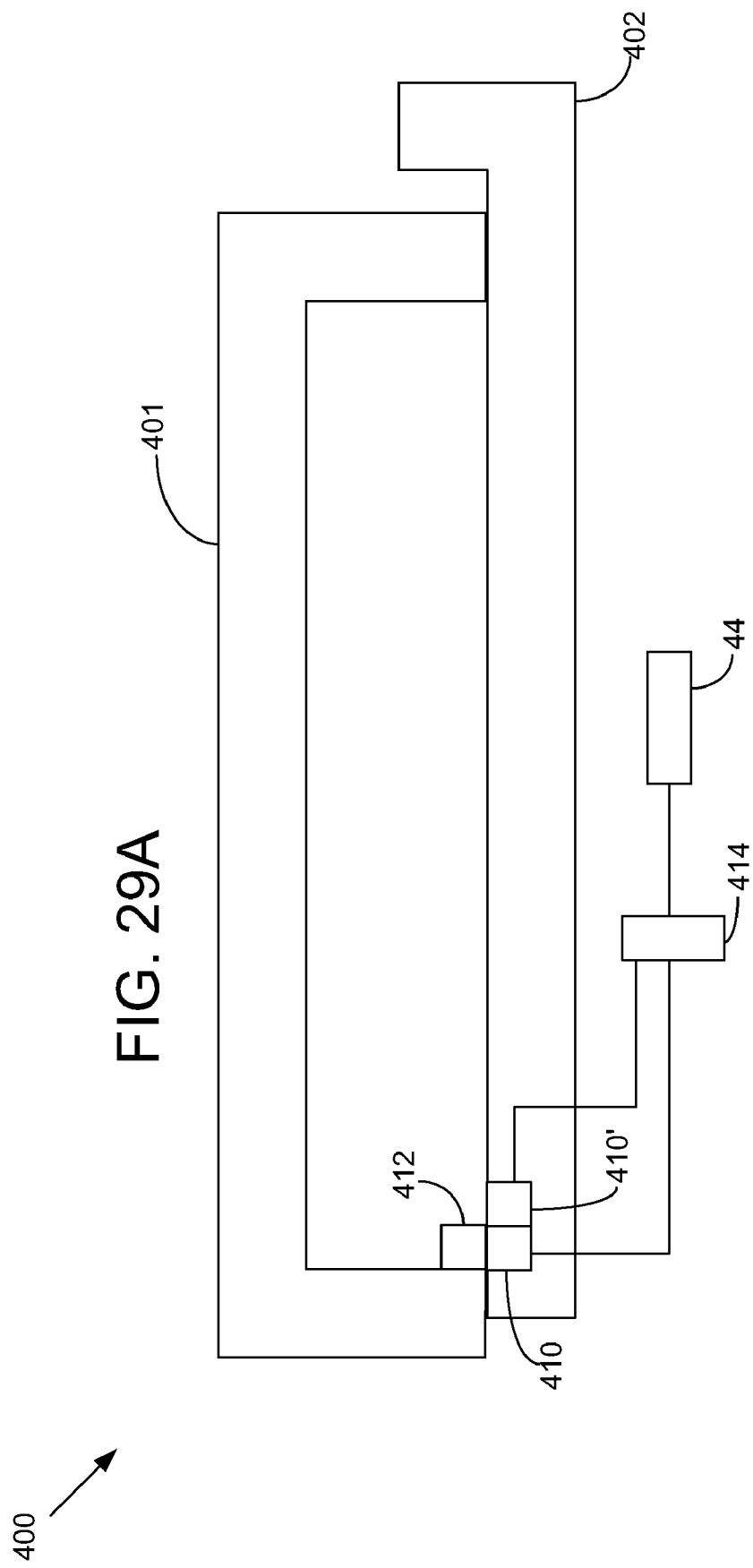

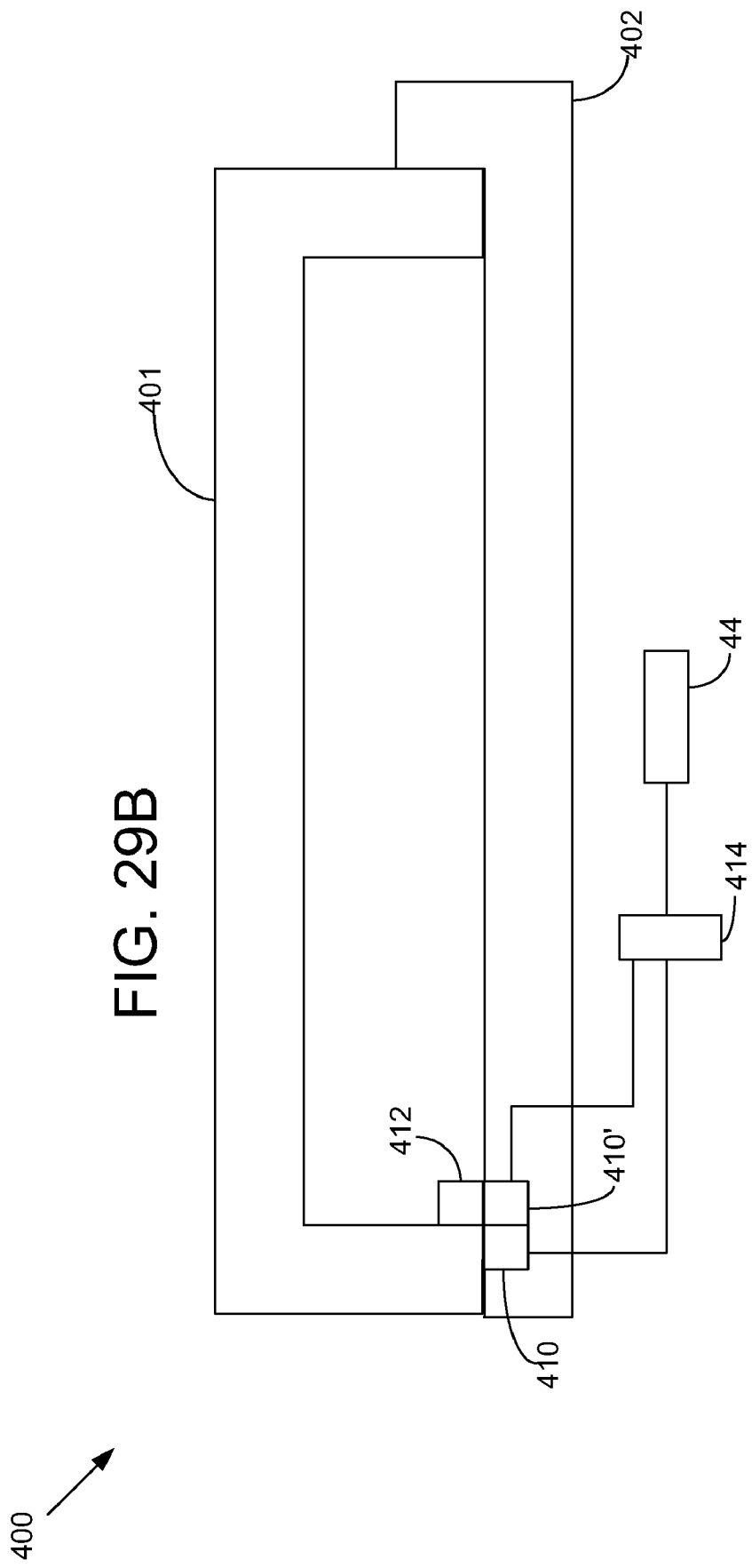

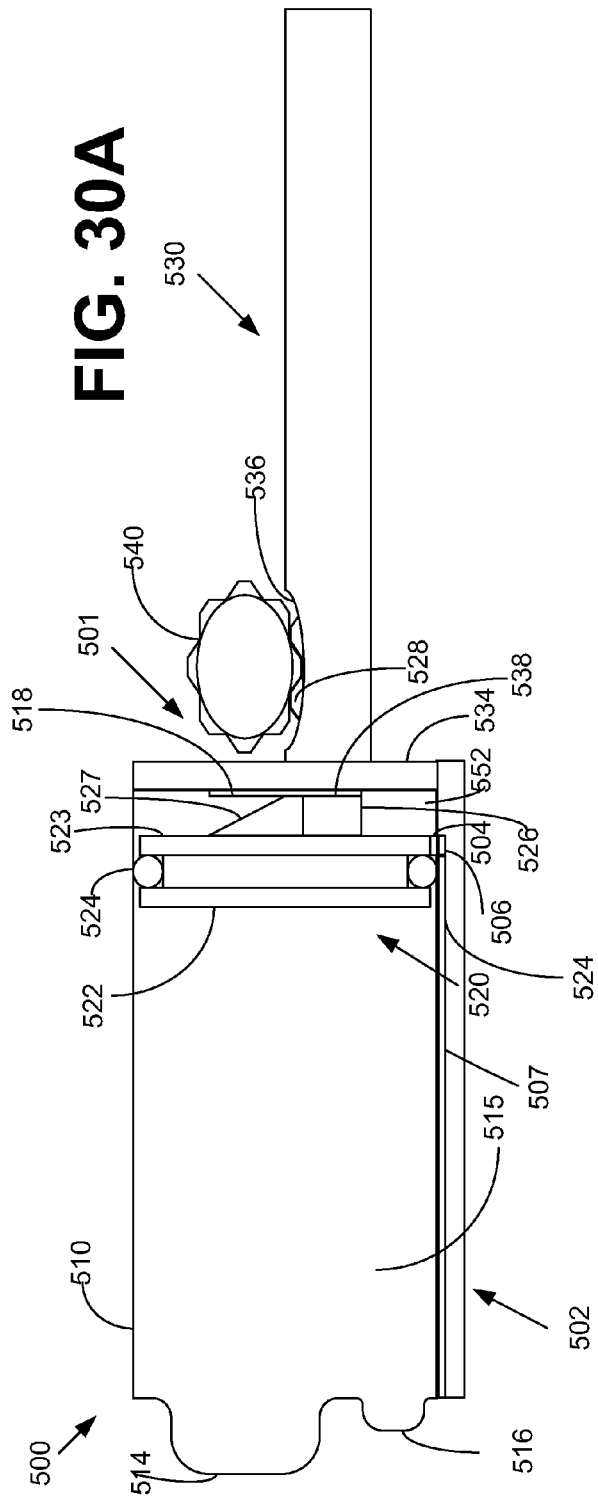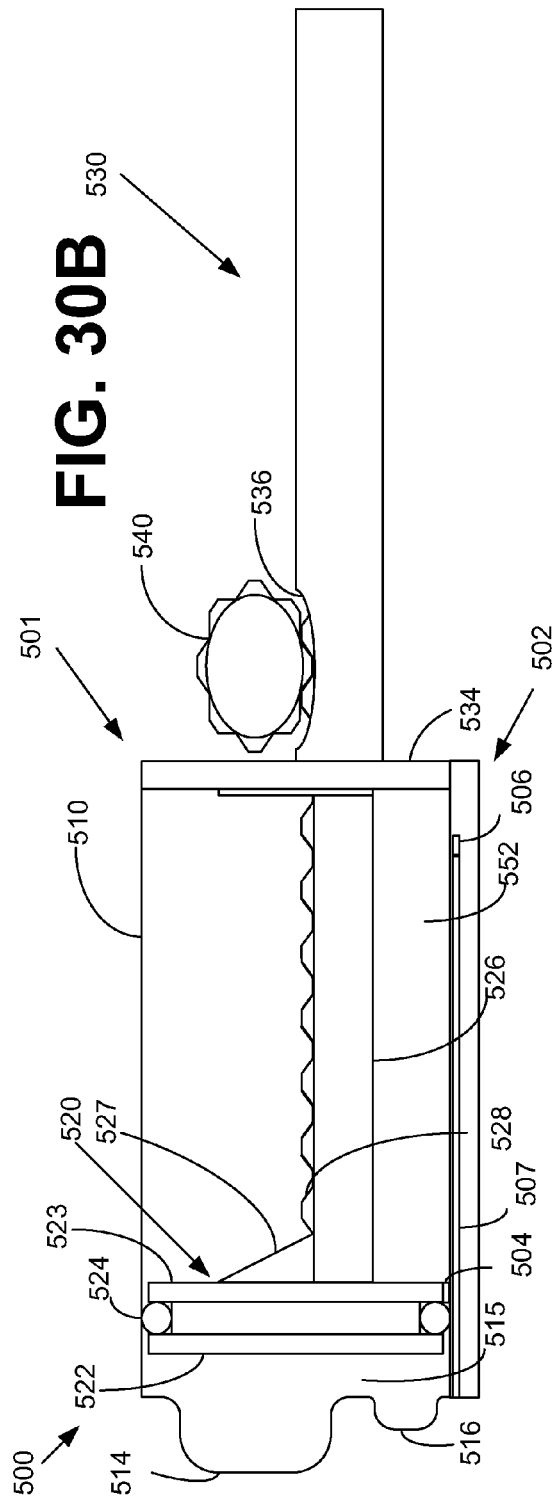

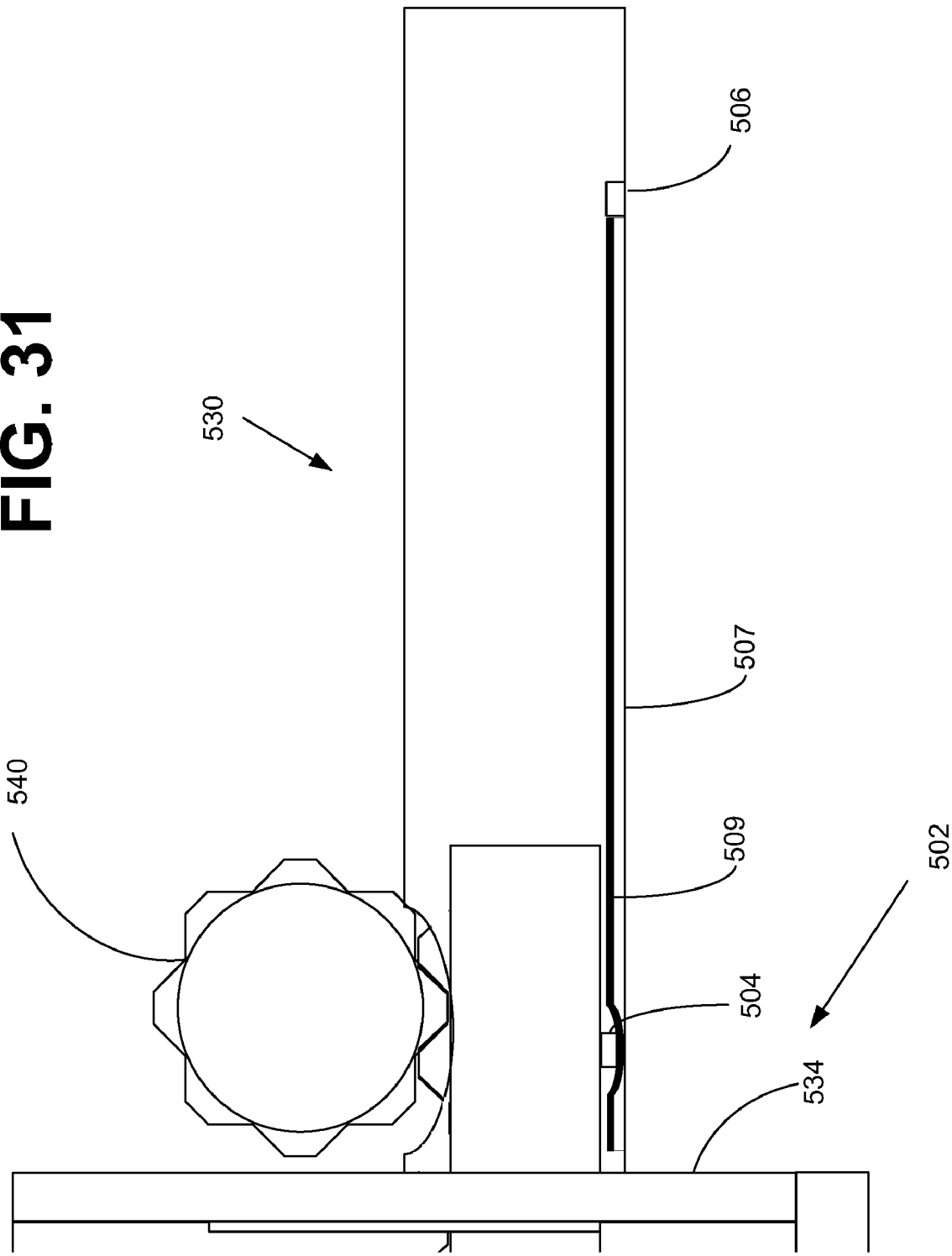

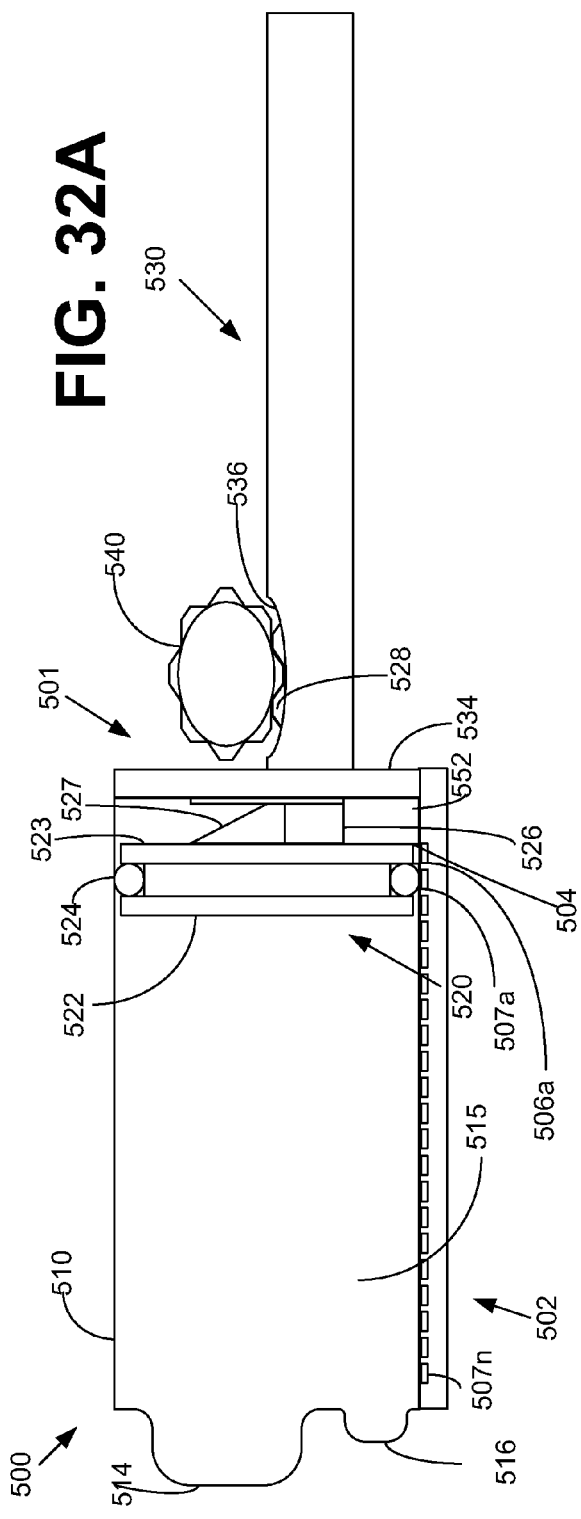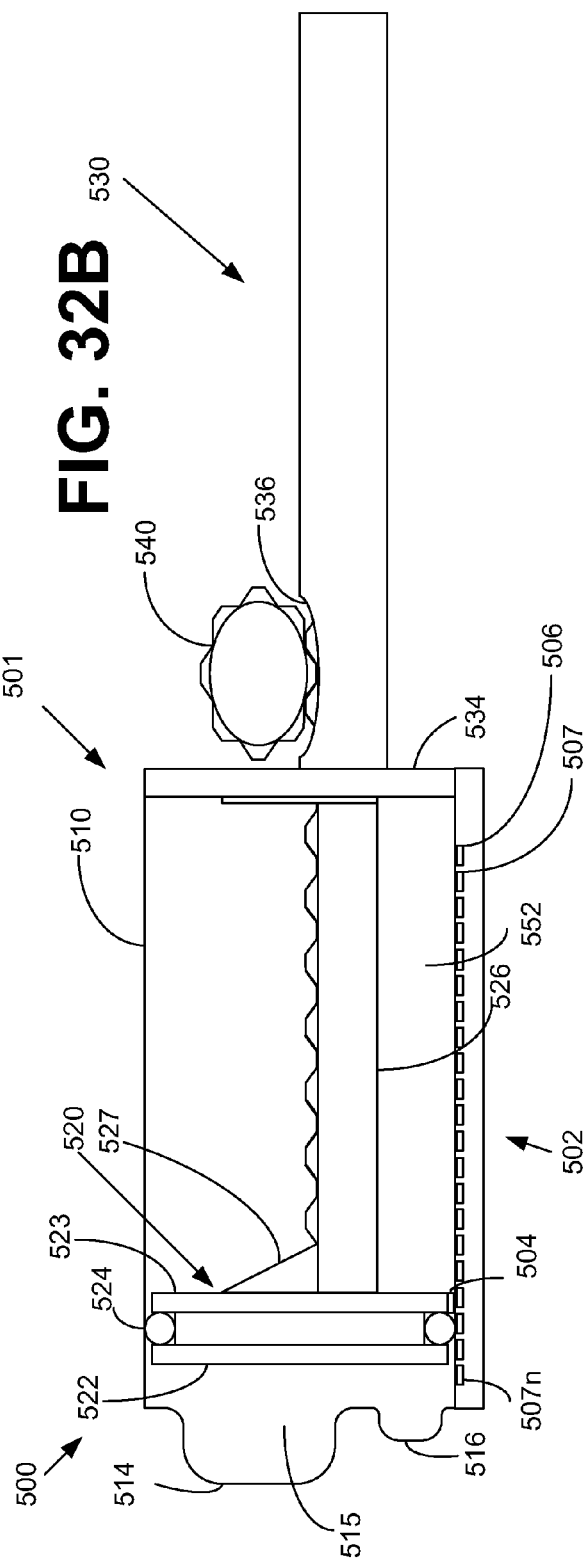

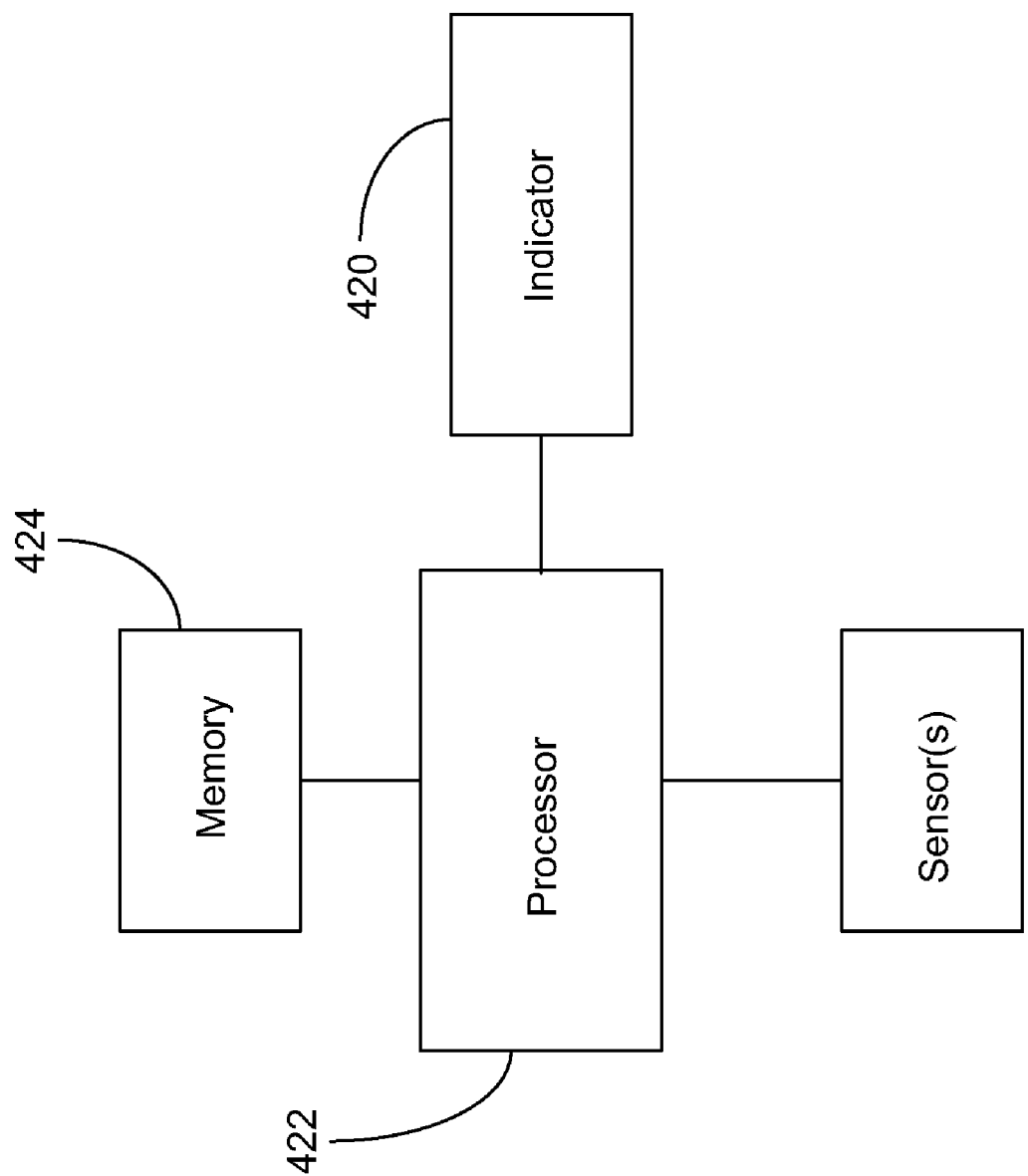

ALIGNMENT SYSTEMS AND METHODS

BACKGROUND

1. Field of the Invention

Embodiments of the present invention generally relate to medical device systems and methods, and, in specific embodiments, such systems and methods that include alignment and/or connection features for aligning and/or connecting components of a medical device system.

2. Related Art

According to modern medical techniques, certain chronic diseases may be treated by delivering a medication or other substance to the body of a patient. For example, diabetes is a chronic disease that is commonly treated by delivering defined amounts of insulin to a patient at appropriate times. Traditionally, manually operated syringes and insulin pens have been employed for delivering insulin to a patient. More recently, modern systems have been designed to include programmable pumps for delivering controlled amounts of medication to a patient.

Pump type delivery devices have been configured in external devices, which connect to a patient, and have been configured in implantable devices, which are implanted inside of the body of a patient. External pump type delivery devices include devices designed for use in a stationary location, such as a hospital, a clinic, and/or the like, and further include devices configured for ambulatory or portable use, such as devices designed to be carried by a patient, and/or the like. External pump-type delivery devices may contain reservoirs of fluidic media, such as, but is not limited to, insulin.

External pump-type delivery devices may be connected in fluid flow communication to a patient or user-patient, for example, through suitable hollow tubing. The hollow tubing may be connected to a hollow needle that is designed to pierce the skin of the patient and to deliver fluidic media there through. Alternatively, the hollow tubing may be connected directly to the patient as through a cannula, and/or the like.

Examples of some external pump type delivery devices are described in U.S. patent application Ser. No. 11/211,095, filed Aug. 23, 2005, titled "Infusion Device And Method With Disposable Portion" and Published PCT Application WO 01/70307 (PCT/US01/09139) titled "Exchangeable Electronic Cards For Infusion Devices" (each of which is owned by the assignee of the present invention), Published PCT Application WO 04/030716 (PCT/US2003/028769) titled "Components And Methods For Patient Infusion Device," Published PCT Application WO 04/030717 (PCT/US2003/029019) titled "Dispenser Components And Methods For Infusion Device," U.S. Patent Application Publication No. 2005/0065760 titled "Method For Advising Patients Concerning Doses Of Insulin," and U.S. Pat. No. 6,589,229 titled "Wearable Self-Contained Drug Infusion Device," each of which is incorporated herein by reference in its entirety.

External pump-type delivery devices may be connected in fluid-flow communication to a patient-user, for example, through suitable hollow tubing. The hollow tubing may be connected to a hollow needle that is designed to pierce the patient-user's skin and deliver an infusion medium to the patient-user. Alternatively, the hollow tubing may be connected directly to the patient-user as or through a cannula or set of micro-needles.

In contexts in which the hollow tubing is connected to the patient-user through a hollow needle that pierces skin of the user-patient, a manual insertion of the needle into the patient-user can be somewhat traumatic to the user-patient. Accordingly, insertion mechanisms have been made to assist the insertion of a needle into the user-patient, whereby a needle is forced by a spring to move quickly from a retracted position into an extended position. As the needle is moved into the extended position, the needle is quickly forced through the skin of the user-patient in a single, relatively abrupt motion that can be less traumatic to certain user-patients as compared to a slower, manual insertion of a needle. While a quick thrust of the needle into the skin of the user-patient may be less traumatic to some user-patients than a manual insertion, it is believed that, in some contexts, some user-patients may feel less trauma if the needle is moved a very slow, steady pace.

Examples of insertion mechanisms that may be used with and may be built into a delivery device are described in: U.S. patent application Ser. No. 11/645,435, filed Dec. 26, 2006, titled "Infusion Medium Delivery system, Device And Method With Needle Inserter And Needle Inserter Device And Method,"; and U.S. patent application Ser. No. 11/211,095, filed Aug. 23, 2005, titled "Infusion Device And Method With Disposable Portion" (each of which is assigned to the assignee of the present invention), each of which is incorporated herein by reference in its entirety. Other examples of insertion tools are described in U.S. Patent Application Publication No. 2002/0022855, titled "Insertion Device For An Insertion Set And Method Of Using The Same" (assigned to the assignee of the present invention), which is incorporated herein by reference in its entirety. Other examples of needle/cannula insertion tools that may be used (or modified for use) to insert a needle and/or cannula, are described in, for example U.S. patent application Ser. No. 10/389,132 filed Mar. 14, 2003, and entitled "Auto Insertion Device For Silhouette Or Similar Products," and/or U.S. patent application Ser. No. 10/314,653 filed Dec. 9, 2002, and entitled "Insertion Device For Insertion Set and Method of Using the Same," both of which are incorporated herein by reference in their entirety.

Pump-type delivery devices can allow accurate doses of insulin to be calculated and delivered automatically to a patient-user at any time during the day or night. Furthermore, when used in conjunction with glucose sensors or monitors, insulin pumps may be automatically controlled to provide appropriate doses of infusion medium at appropriate times of need, based on sensed or monitored levels of blood glucose.

Pump-type delivery devices have become an important aspect of modern medical treatments of various types of medical conditions, such as diabetes. As pump technologies improve and as doctors and patient-users become more familiar with such devices, the popularity of external medical infusion pump treatment increases and is expected to increase substantially over the next decade.

SUMMARY OF THE DISCLOSURE

A delivery system for delivering fluidic media to a user may include, but is not limited to, a first housing portion, a second housing portion, a drive device, a pair of interactive elements, and circuitry. The first housing portion may be adapted to be carried by a user. The second housing portion may be configured to be selectively operatively engaged with and disengaged from the first housing portion. One of the first housing portion and the second housing portion may support a reservoir having an interior volume for containing fluidic media and a plunger head moveable within the interior volume of the reservoir along an axial direction of the reservoir.

A drive device may be supported by the other of the first housing portion and the second housing portion relative to the one of the first housing portion and the second housing portion supporting the reservoir such that upon the first housing portion and the second housing portion being operatively engaged, the reservoir is operatively coupled to the drive device. The pair of interactive elements may include a first interactive element supported on the first housing portion and a second interactive element supported on the second housing portion at a location to be interactable with the first interactive element. The circuitry may be configured to detect an interaction between the first interactive element and the second interactive element. The circuitry may be configured to provide a signal or a change in state in response to the first housing portion and the second housing portion being operatively engaged and an interaction between the first interactive element and the second interactive element being detected.

In some embodiments, the first interactive element and the second interactive element may be configured to be interactable with each other in a case where the first housing portion and the second housing portion are operatively engaged and positioned relative to each other in a predetermined manner. In further embodiments, the first housing portion and the second housing portion may be positioned relative to each other in a predetermined manner in a case where the first housing portion and the second housing portion are aligned in more than one dimension. In further embodiments, the first housing portion and the second housing portion may be positioned relative to each other in a predetermined manner in a case where the first interactive element and the second interactive element are sufficiently proximate to each other.

In some embodiments, the first interactive element and the second interactive element may be configured to be interactable with each other in a case where the first housing portion and the second housing portion are operatively engaged and the first interactive element and the second interactive element are sufficiently proximate to each other. In further embodiments, the first interactive element and the second interactive element may be sufficiently proximate to each other in a case where the first interactive element and the second interactive element contact each other.

In some embodiments, the delivery system may further include a user-perceptible indicator operatively connected to the circuitry. The user-perceptible indicator may be for providing a user-perceptible indication in response to a signal or a change in state by the circuitry in a case where the first housing portion and the second housing portion are operatively engaged and an interaction between the first interactive element and the second interactive element is detected. In further embodiments, the user-perceptible indication may comprise at least one of an audible indication, a visual indication, and a tactile indication.

In some embodiments, the first interactive element and the second interactive element may be configured to be electronically interactable with each other. In some embodiments, one of the first interactive element and the second interactive element may comprise an electrical contact and the other of the first interactive element and the second interactive element comprises an electrically conductive material. The circuitry may be configured to detect an interaction in a case where the first housing portion and the second housing portion are operatively engaged and the electrical contact contacts the electrically conductive material. In further embodiments, one of the electrical contact and the electrically conductive material may comprise at least one of a spring and a protrusion adapted to contact the other of the electrical contact and the electrically conductive material upon the first housing portion and the second housing portion being operatively engaged.

In some embodiments, the delivery system may further include control electronics operatively connected to the circuitry for controlling the drive device to drive fluid from the reservoir based upon the signal or the state provided by the circuitry. In further embodiments, the control electronics may be configured to inhibit operation of the drive device unless the signal or the state provided by the circuitry corresponds to the signal or the state when the first housing portion and the second housing portion are operatively engaged. In further embodiments, the control electronics may be configured to change from a first power state to a second power state in a case where the first housing portion and the second housing portion are operatively engaged and an interaction between the first interactive element and the second interactive element is detected.

In some embodiments, at least one of the first interactive element and the second interactive element may be arranged on a movable portion of at least one of the reservoir and the drive device. A position of the first interactive element relative to the second interactive element may correspond to reservoir data. In some embodiments, at least one of the first interactive element and the second interactive element may be configured to be moveable relative to the other of the first interactive element and the second interactive element. A position of the first interactive element relative to the second interactive element may correspond to reservoir data.

In further embodiments, the reservoir data may include data relating to a volume of fluidic media in the reservoir. In further embodiments, the drive device may include at least one of a plunger head for driving fluid out from the reservoir and a plunger arm operatively connected to the plunger head for moving the plunger head. The at least one of the first interactive element and the second interactive element may be supported on at least one of the plunger head and the plunger arm. In further embodiments, at least one of the first interactive element and the second interactive element may comprise a linear sensor. In yet further embodiments, the linear sensor may be configured to sense a linear position. In further embodiments, at least one of the first interactive element and the second interactive element may comprise one of a linear conductor and a linear resistor.

In some embodiments, at least one of the first interactive element and the second interactive element may be configured to be moveable relative to the other of the first interactive element and the second interactive element. At least one of the first interactive element and the second interactive element may comprise a plurality of conductors. A position of the other of the first interactive element and the second interactive element relative to one of the plurality of conductors may correspond to reservoir data.

In some embodiments, the delivery system may further include a second pair of interactive elements including a third interactive element supported on the first housing portion and a fourth interactive element supported on the second housing portion at a location to be interactable with the third interactive element. The circuitry may be configured to detect an interaction between the third interactive element and the fourth interactive element. The circuitry may be configured to provide a signal or a change in state in response to the first housing portion and the second housing portion being operatively engaged and an interaction between the third interactive element and the fourth interactive element being detected.

In further embodiments, at least one of the third interactive element and the fourth interactive element may be configured to be moveable relative to the other of the first interactive element and the second interactive element. In yet further embodiments, a position of the third interactive element relative to the fourth interactive element may correspond to reservoir data. In yet further embodiments, the drive device may comprise at least one of a plunger head for driving fluid out from the reservoir and a plunger arm operatively connected to the plunger head for moving the plunger head. The at least one of the third interactive element and the fourth interactive element may be supported on at least one of the plunger head and the plunger arm. In yet further embodiments, at least one of the third interactive element and the fourth interactive element may comprise a linear sensor. In even further embodiments, the linear sensor may be configured to sense a linear position.

In some embodiments, at least one of the first interactive element and the second interactive element may be adapted to be insert mold labeled to the first housing portion and the second housing portion respectively. In some embodiments, the delivery system may further include a film cover for supporting at least one of the first interactive element and the second interactive element on the first housing portion and the second housing portion respectively.

In some embodiments, the delivery system may further include a reservoir supported by one of the first housing portion and the second housing portion. The reservoir may have an interior volume for containing fluidic media. In some embodiments, the one of the first housing portion and the second portion may comprise a reservoir supported by one of the first housing portion and the second housing portion. The reservoir may have an interior volume for containing fluidic media.

In some embodiments, the circuitry may comprise a responsive device configured to provide the signal or the change in state in response to the first housing portion and the second housing portion being operatively engaged and the interaction between the first interactive element and the second interactive element being detected.

In some embodiments, the delivery system may further include a bias mechanism for biasing at least one of the first interactive element and the second interactive element toward each other. In some embodiments, one of the first interactive element and the second interactive element may comprise a flexible conductive membrane. The other of the first interactive element and the second interactive element may be configured to press against the flexible conductive membrane upon the first housing portion and the second housing portion being operatively engaged.

In some embodiments, the first interactive element may comprise a detectable feature. The second interactive element may comprise a sensor configured to sense the detectable feature. The circuitry may be configured to provide a signal or a change in state in a case where the first housing portion and the second housing portion are operatively engaged and the detectable feature is detected by the sensor.

In further embodiments, at least one of the sensor and the detectable feature may comprise at least one of a linear resistor and a discrete contact switch. In further embodiments, the detectable feature may comprise at least one of a coded resistor pattern, an electrical contact, an electromechanical switch.

In further embodiments, the sensor may comprise an optical sensor. In yet further embodiments, the optical sensor may comprise at least one of a color detector and a grayscale detector. In yet further embodiments, the optical sensor may comprise a bar code reader. The detectable feature may comprise a bar code.

In further embodiments, the sensor may comprise an ultrasonic sensor. The detectable feature may comprise an ultrasonic signature. In further embodiments, the detectable feature may comprise a radio frequency identification device.

In various embodiments, one of the first interactive element and the second interactive element may have a capacitance that is measurable. The other of the one of the first interactive element and the second interactive element may be configured to affect the capacitance. The circuitry may be configured to provide a signal or a change in state in a case where the first housing portion and the second housing portion are operatively engaged and the capacitance is affected by the other of the one of the first interactive element and the second interactive element.

In various embodiments, one of the first interactive element and the second interactive element may have an inductance that is measurable. The other of the one of the first interactive element and the second interactive element may be configured to affect the inductance. The circuitry may be configured to provide a signal or a change in state in a case where the first housing portion and the second housing portion are operatively engaged and the inductance is affected by the other of the one of the first interactive element and the second interactive element.

In further embodiments, the sensor may comprise at least one magnetic sensor. The detectable feature may comprise a magnetic material. In further embodiments, one of the sensor and the detectable feature may comprise an occlusion sensor of the delivery system for sensing an occlusion in the reservoir.

A method of making a delivery system may include, but is not limited to, any one of or combination of: (i) adapting a first housing portion to be carried by a user; (ii) configuring a second housing portion to be selectively operatively engaged with and disengaged from the first housing portion, one of the first housing portion and the second housing portion supporting a reservoir having an interior volume for containing fluidic media and a plunger head moveable within the interior volume of the reservoir along an axial direction of the reservoir; (iii) supporting a drive device on the other of the first housing portion and the second housing portion relative to the one of the first housing portion and the second housing portion supporting the reservoir such that upon the first housing portion and the second housing portion being operatively engaged, the reservoir is operatively coupled to the drive device; (iv) supporting a pair of interactive elements including supporting a first interactive element on the first housing portion and supporting a second interactive element on the second housing portion at a location to be interactable with the first interactive element; and (v) configuring circuitry to detect an interaction between the first interactive element and the second interactive element, the circuitry configured to provide a signal or a change in state in response to the first housing portion and the second housing portion being operatively engaged and an interaction between the first interactive element and the second interactive element being detected.

BRIEF DESCRIPTION OF THE DRAWINGS

FIG. 7 illustrates a portion of a medical device system in accordance with an embodiment of the present invention;

FIG. 8 illustrates a medical device system in accordance with an embodiment of the present invention;

FIG. 10A illustrates a medical device system in accordance with an embodiment of the present invention;

FIG. 10B illustrates a medical device system in accordance with an embodiment of the present invention;

FIG. 14A illustrates a portion of a medical device system in accordance with an embodiment of the present invention;

FIG. 14B illustrates a portion of a medical device system in accordance with an embodiment of the present invention;

FIG. 15A illustrates a portion of a medical device system in accordance with an embodiment of the present invention FIG. 15B illustrates a portion of a medical device system in accordance with an embodiment of the present invention FIG. 16 illustrates a portion of a medical device system in accordance with an embodiment of the present invention;

FIG. 20 illustrates a medical device system in accordance with an embodiment of the present invention;

FIG. 21 illustrates a medical device system in accordance with an embodiment of the present invention;

FIG. 26 illustrates a medical device system in accordance with an embodiment of the present invention;

FIG. 27 illustrates a medical device system in accordance with an embodiment of the present invention;

FIG. 28 illustrates a medical device system in accordance with an embodiment of the present invention;

FIG. 29A illustrates a medical device system in accordance with an embodiment of the present invention;

FIG. 29B illustrates a medical device system in accordance with an embodiment of the present invention;

FIG. 30A illustrates a medical device system in accordance with an embodiment of the present invention;

FIG. 30B illustrates a medical device system in accordance with an embodiment of the present invention;

FIG. 31 illustrates a portion of a medical device system in accordance with an embodiment of the present invention;

FIG. 32A illustrates a medical device system in accordance with an embodiment of the present invention;

FIG. 32B illustrates a medical device system in accordance with an embodiment of the present invention; and FIG. 33 illustrates a block diagram of an electrical configuration of a medical device system in accordance with an embodiment of the present invention.

DETAILED DESCRIPTION

Figure 1:
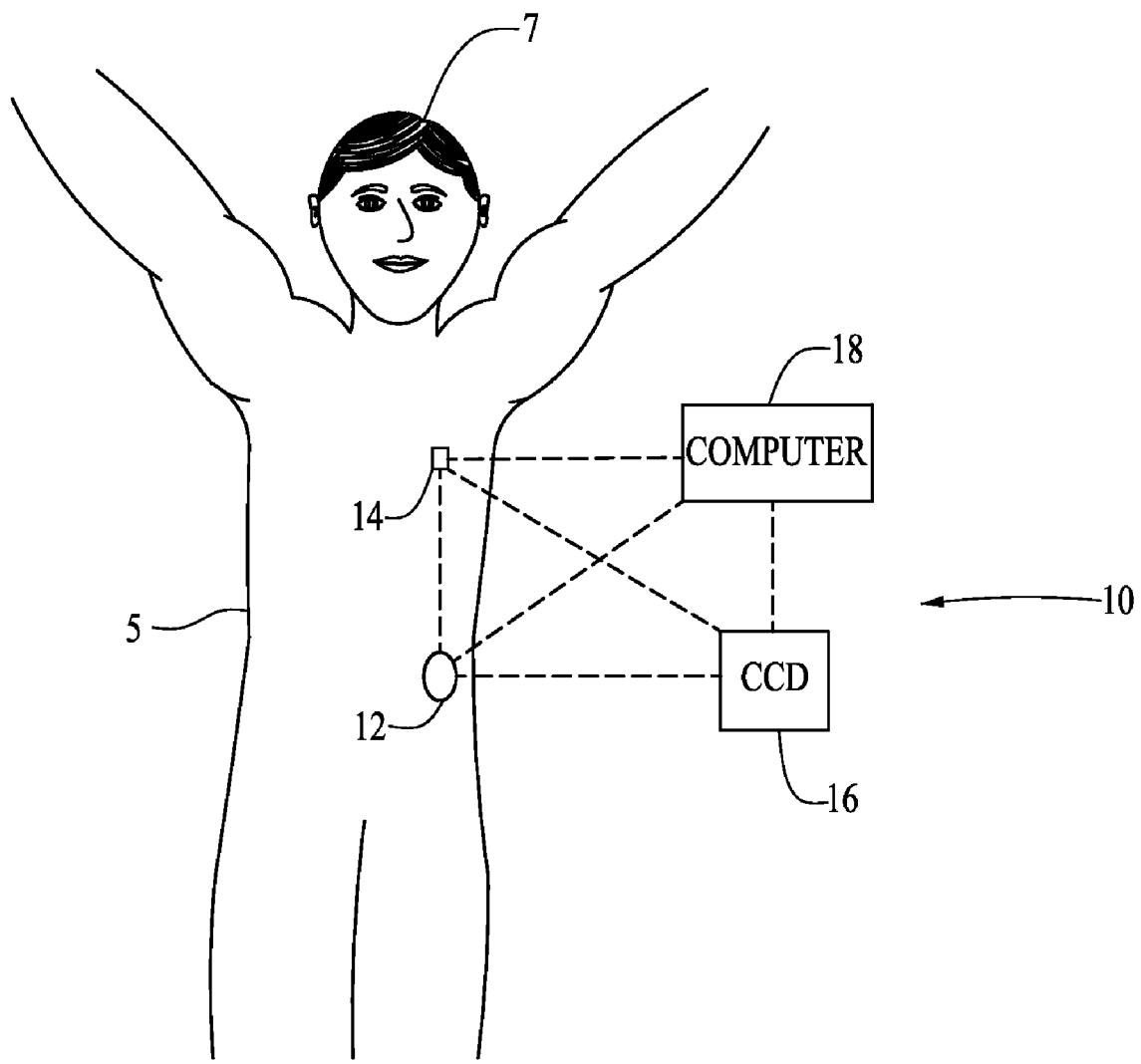
FIG. 1 illustrates a generalized representation of a system in accordance with an embodiment of the present invention.

FIG. 1 illustrates a generalized representation of a system 10 in accordance with an embodiment of the present invention. The system 10 may include a delivery device 12. The system 10 may further include a sensing device 14, a command control device (CCD) 16, and a computer 18. In various embodiments, the delivery device 12 and the sensing device 14 may be secured at desired locations on the body 5 of a patient or user-patient 7. The locations at which the delivery device 12 and the sensing device 14 are secured to the body 5 of the user-patient 7 in FIG. 1 are provided only as representative, non-limiting, examples. It should be noted that user-patient as used throughout the disclosure may include patient-user, patient, or user (e.g., a patient, a medical professional, or other treating the patient).

The system 10, the delivery device 12, the sensing device 14, the CCD 16, and computer 18 may be similar to those described in the following U.S. patent applications that were assigned to the assignee of the present invention, where each of following patent applications is incorporated herein by reference in its entirety: (i) U.S. patent application Ser. No. 11/211,095, filed Aug. 23, 2005, "Infusion Device And Method With Disposable Portion"; (ii) U.S. patent application Ser. No. 11/515,225, filed Sep. 1, 2006, "Infusion Medium Delivery Device And Method With Drive Device For Driving Plunger In Reservoir"; (iii) U.S. patent application Ser. No. 11/588,875, filed Oct. 27, 2006, "Systems And Methods Allowing For Reservoir Filling And Infusion Medium Delivery"; (iv) U.S. patent application Ser. No. 11/588,832, filed Oct. 27, 2006, "Infusion Medium Delivery Device And Method With Drive Device For Driving Plunger In Reservoir"; (v) U.S. patent application Ser. No. 11/588,847, filed Oct. 27, 2006, "Infusion Medium Delivery Device And Method With Compressible Or Curved Reservoir Or Conduit"; (vi) U.S. patent application Ser. No. 11/589,323, filed Oct. 27, 2006, "Infusion Pumps And Methods And Delivery Devices And Methods With Same"; (vii) U.S. patent application Ser. No. 11/602,173, filed Nov. 20, 2006, "Systems And Methods Allowing For Reservoir Filling And Infusion Medium Delivery"; (viii) U.S. patent application Ser. No. 11/602,052, filed Nov. 20, 2006, "Systems And Methods Allowing For Reservoir Filling And Infusion Medium Delivery"; (ix) U.S. patent application Ser. No. 11/602,428, filed Nov. 20, 2006, "Systems And Methods Allowing For Reservoir Filling And Infusion Medium Delivery"; (x) U.S. patent application Ser. No. 11/602,113, filed Nov. 20, 2006, "Systems And Methods Allowing For Reservoir Filling And Infusion Medium Delivery"; (xi) U.S. patent application Ser. No. 11/604,171, filed Nov. 22, 2006, "Infusion Medium Delivery Device And Method With Drive Device For Driving Plunger In Reservoir"; (xii) U.S. patent application Ser. No. 11/604,172, filed Nov. 22, 2006, "Infusion Medium Delivery Device And Method With Drive Device For Driving Plunger In Reservoir"; (xiii) U.S. patent application Ser. No. 11/606,703, filed Nov. 30, 2006, "Infusion Pumps And Methods And Delivery Devices And Methods With Same"; (xiv) U.S. patent application Ser. No. 11/606,836, filed Nov. 30, 2006, "Infusion Pumps And Methods And Delivery Devices And Methods With Same"; U.S. patent application Ser. No. 11/636,384, filed Dec. 8, 2006, "Infusion Medium Delivery Device And Method With Compressible Or Curved Reservoir Or Conduit"; (xv) U.S. patent application Ser. No. 11/645,993, filed Dec. 26, 2006, "Infusion Medium Delivery Device And Method With Compressible Or Curved Reservoir Or Conduit"; U.S. patent application Ser. No. 11/645,972, filed Dec. 26, 2006, "Infusion Medium Delivery System, Device And Method With Needle Inserter And Needle Inserter Device And Method"; (xvi) U.S. patent application Ser. No. 11/646,052, filed Dec. 26, 2006, "Infusion Medium Delivery System, Device And Method With Needle Inserter And Needle Inserter Device And Method"; (xvii) U.S. patent application Ser. No. 11/645,435, filed Dec. 26, 2006, "Infusion Medium Delivery System, Device And Method With Needle Inserter And Needle Inserter Device And Method"; (xviii) U.S. patent application Ser. No. 11/646,000, filed Dec. 26, 2006, "Infusion Medium Delivery System, Device And Method With Needle Inserter And Needle Inserter Device And Method"; and (xix) U.S. patent application Ser. No. 11/759,725, filed Jun. 7, 2007, "Infusion Medium Delivery Device And Method With Drive Device For Driving Plunger In Reservoir"; (xx) U.S. patent application Ser. No. 11/606,837, filed Nov. 30, 2006, "Method And Apparatus For Enhancing The Integrity Of An Implantable Sensor Device"; (xxi) U.S. patent application Ser. No. 11/702,713, filed Feb. 5, 2007, "Selective Potting For Controlled Failure And Electronic Devices Employing The Same"; (xxii) U.S. patent application Ser. No. 11/843,601, filed Aug. 22, 2007, "System And Method For Sensor Recalibration"; (xxiii) U.S. patent application Ser. No. 11/868,898, filed Oct. 8, 2007, "Multilayer Substrate"; (xxiv) U.S. patent application Ser. No. 11/964,649, filed Dec. 26, 2007, "System And Methods Allowing For Reservoir Air Bubble Management"; (xxv) U.S. patent application Ser. No. 12/111,751, filed Apr. 29, 2008, "Systems And Methods For Reservoir Filling"; (xxvi) U.S. patent application Ser. No. 12/111,815, filed Apr. 29, 2008, "Systems And Methods For Reservoir Air Bubble Management"; (xxvii) U.S. patent application Ser. No. 11/924,402, filed Oct. 25, 2007, "Sensor Substrate And Method Of Fabricating Same"; (xxviii) U.S. patent application Ser. No. 11/929,428, filed Oct. 30, 2007, "Telemetry System And Method With Variable Parameters"; (xxix) U.S. patent application Ser. No. 11/965,578, filed Dec. 27, 2007, "Reservoir Pressure Equalization Systems And Methods"; (xxx) U.S. patent application Ser. No. 12/107,580, filed Apr. 22, 2008, "Automative Filling Systems And Methods"; (xxxi) U.S. patent application Ser. No. 11/964,663, filed Dec. 26, 2007, "Medical Device With Full Options And Selective Enablement/Disablement"; (xxxii) U.S. patent application Ser. No. 10/180,732, filed Jun. 26, 2002, "Communication Station And Software For Interfacing With An Infusion Pump, Analyte Monitor, Analyte Meter, And/or the like"; (xxxiii) U.S. patent application Ser. No. 12/099,738, filed Apr. 8, 2008, "Systems And Methods Allowing For Reservoir Air Bubble Management"; (xxxiv) U.S. patent application Ser. No. 12/027,963, filed Feb. 7, 2008, "Adhesive Patch Systems And Methods"; (xxxv) U.S. patent application Ser. No. 12/121,647, filed May 15, 2008, "Multi-Lumen Catheter"; (xxxvi) U.S. Patent Provisional App. Ser. No. 61/044,269, filed Apr. 11, 2008, "Reservoir Plunger Head Systems And Methods"; (xxxvii) U.S. Patent App. Ser. No. 61/044,292, filed Apr. 11, 2008, "Reservoir Barrier Layer Systems And Methods"; (xxxviii) U.S. Patent Provisional App. Ser. No. 61/044,322, filed Apr. 11, 2008, "Reservoir Seal Retainer Systems And Methods"; (xxxix) U.S. patent application Ser. No. 12/179,502, filed Jul. 24, 2008, "Method For Formulating And Immobilizing A Matrix Protein And A Matrix Protein For Use In A Sensor"; (xl) U.S. patent application Ser. No. 12/336,367, filed Dec. 16, 2008, "Needle Insertions Systems And Methods"; (xli) U.S. patent application Ser. No. 12/166,210, filed Jul. 1, 2008, "Electronic Device For Controlled Failure"; (xlii) U.S. patent application Ser. No. 12/271,134, filed Nov. 14, 2008, "Multilayer Circuit Devices And Manufacturing Methods Using Electroplated Sacrificial Structures"; (xliii) U.S. patent application Ser. No. 12/171,971, filed Jul. 11, 2008, "Infusion Medium Delivery System, Device And Method With Needle Inserter And Needle Inserter Device And Method"; (xliv) U.S. patent application Ser. No. 12/189,077, filed Aug. 8, 2008, "Packaging System"; (xlv) U.S. patent application Ser. No. 12/179,536, filed Jul. 24, 2008, "Real Time Self-Adjusting Calibration Algorithm"; (xlvii) U.S. patent application Ser. No. 12/277,186, filed Nov. 24, 2008, "Infusion Medium Delivery System, Device And Method With Needle Inserter And Needle Inserter Device And Method"; (xlviii) U.S. patent application Ser. No. 12/211,783, filed Sep. 16, 2008, "Implantable Sensor Method And System"; (xlix) U.S. patent application Ser. No. 12/247,945, filed Oct. 8, 2008, "Infusion Medium Delivery Device And Method With Drive Device For Driving Plunger In Reservoir"; (l) U.S. patent application Ser. No. 12/360,077, filed Jan. 26, 2009, "Reservoir Barrier Layer Systems And Methods"; (li) U.S. patent application Ser. No. 12/345,362, filed Dec. 29, 2008, "Reservoir Seal Retainer Systems And Methods"; (lii) U.S. patent application Ser. No. 12/353,181, filed Jan. 13, 2009, "Systems And Methods Allowing For Reservoir Filling And Infusion Medium Delivery"; and (liii) U.S. patent application Ser. No. 12/360,813, filed Jan. 27, 2009, "Multi-Position Infusion Set Device And Process." In other embodiments, the system 10, delivery device 12, sensing device 14, CCD 16, and computer 18 may have other suitable configurations.

The delivery device 12 may be configured to deliver fluidic media to the body 5 of the user-patient 7. In various embodiments, fluidic media may include a liquid, a fluid, a gel, or the like. In some embodiments, fluidic media may include a medicine or a drug for treating a disease or a medical condition. For example, fluidic media may include insulin for treating diabetes, or may include a drug for treating pain, cancer, a pulmonary disorder, HIV, or the like. In some embodiments, fluidic media may include a nutritional supplement, a dye, a tracing medium, a saline medium, a hydration medium, or the like.

The sensing device 14 may include a sensor, a monitor, or the like, for providing sensor data or monitor data. In various embodiments, the sensing device 14 may be configured to sense a condition of the user-patient 7. For example, the sensing device 14 may include electronics and enzymes reactive to a biological condition, such as a blood glucose level, or the like, of the user-patient 7.

In various embodiments, the sensing device 14 may be secured to the body 5 of the user-patient 7 or embedded in the body 5 of the user-patient 7 at a location that is remote from the location at which the delivery device 12 is secured to the body 5 of the user-patient 7. In various other embodiments, the sensing device 14 may be incorporated within the delivery device 12. In other embodiments, the sensing device 14 may be separate and apart from the delivery device, and may be, for example, part of the CCD 16. In such embodiments, the sensing device 14 may be configured to receive a biological sample, analyte, or the like, to measure a condition of the user-patient 7.

In further embodiments, the sensing device 14 and/or the delivery device 12 may utilize a closed-loop system. Examples of sensing devices and/or delivery devices utilizing closed-loop systems may be found at, but are not limited to, the following references: (i) U.S. Pat. No. 6,088,608, entitled "Electrochemical Sensor And Integrity Tests Therefor"; (ii) U.S. Pat. No. 6,119,028, entitled "Implantable Enzyme-Based Monitoring Systems Having Improved Longevity Due To Improved Exterior Surfaces"; (iii) U.S. Pat. No. 6,589,229, entitled "Implantable Enzyme-Based Monitoring Systems Adapted for Long Term Use"; (iv) U.S. Pat. No. 6,740,072, entitled "System And Method For Providing Closed Loop Infusion Formulation Delivery"; (v) U.S. Pat. No. 6,827,702, entitled "Safety Limits For Closed-Loop Infusion Pump Control"; (vi) U.S. Pat. No. 7,323,142, entitled "Sensor Substrate And Method Of Fabricating Same"; (vii) U.S. patent application Ser. No. 09/360,342, filed Jul. 22, 1999, entitled "Substrate Sensor"; and (viii) U.S. Provisional Patent App. Ser. No. 60/318,060, filed Sep. 7, 2001, entitled "Sensing Apparatus and Process", all of which are incorporated herein by reference in their entirety.

In such embodiments, the sensing device 14 may be configured to sense a condition of the user-patient 7, such as, but not limited to, blood glucose level, or the like. The delivery device 12 may be configured to deliver fluidic media in response to the condition sensed by the sensing device 14. In turn, the sensing device 14 may continue to sense a new condition of the user-patient, allowing the delivery device 12 to deliver fluidic media continuously in response to the new condition sensed by the sensing device 14 indefinitely. In some embodiments, the sensing device 14 and/or the delivery device 12 may be configured to utilize the closed-loop system only for a portion of the day, for example only when the user-patient is asleep or awake.

Each of the delivery device 12, the sensing device 14, the CCD 16, and the computer 18 may include transmitter, receiver, or transceiver electronics that allow for communication with other components of the system 10. The sensing device 14 may be configured to transmit sensor data or monitor data to the delivery device 12. The sensing device 14 may also be configured to communicate with the CCD 16. The delivery device 12 may include electronics and software that are configured to analyze sensor data and to deliver fluidic media to the body 5 of the user-patient 7 based on the sensor data and/or preprogrammed delivery routines.

The CCD 16 and the computer 18 may include electronics and other components configured to perform processing, delivery routine storage, and to control the delivery device 12. By including control functions in the CCD 16 and/or the computer 18, the delivery device 12 may be made with more simplified electronics. However, in some embodiments, the delivery device 12 may include all control functions, and may operate without the CCD 16 and the computer 18. In various embodiments, the CCD 16 may be a portable electronic device. In addition, in various embodiments, the delivery device 12 and/or the sensing device 14 may be configured to transmit data to the CCD 16 and/or the computer 18 for display or processing of the data by the CCD 16 and/or the computer 18.

In some embodiments, the sensing device 14 may be integrated into the CCD 16. Such embodiments may allow the user-patient to monitor a condition by providing, for example, a sample of his or her blood to the sensing device 14 to assess his or her condition. In some embodiments, the sensing device 14 and the CCD 16 may be for determining glucose levels in the blood and/or body fluids of the user-patient without the use of, or necessity of, a wire or cable connection between the delivery device 12 and the sensing device 14 and/or the CCD 16.

In some embodiments, the CCD 16 may be for providing information to the user-patient that facilitates the user-patient's subsequent use of a drug delivery system. For example, the CCD 16 may provide information to the user-patient to allow the user-patient to determine the rate or dose of medication to be administered into the body of the user-patient. In other embodiments, the CCD 16 may provide information to the delivery device 12 to control the rate or dose of medication administered into the body of the user-patient Examples of the types of communications and/or control capabilities, as well as device feature sets and/or program options may be found in the following references: (i) U.S. patent application Ser. No. 10/445,477, filed May 27, 2003, entitled "External Infusion Device with Remote Programming, Bolus Estimator and/or Vibration Alarm Capabilities"; (ii) U.S. patent application Ser. No. 10/429,385, filed May 5, 2003, entitled "Handheld Personal Data Assistant (PDA) with a Medical Device and Method of Using the Same"; and (iii) U.S. patent application Ser. No. 09/813,660, filed Mar. 21, 2001, entitled "Control Tabs for Infusion Devices and Methods of Using the Same," all of which are incorporated herein by reference in their entirety.

Figure 2:
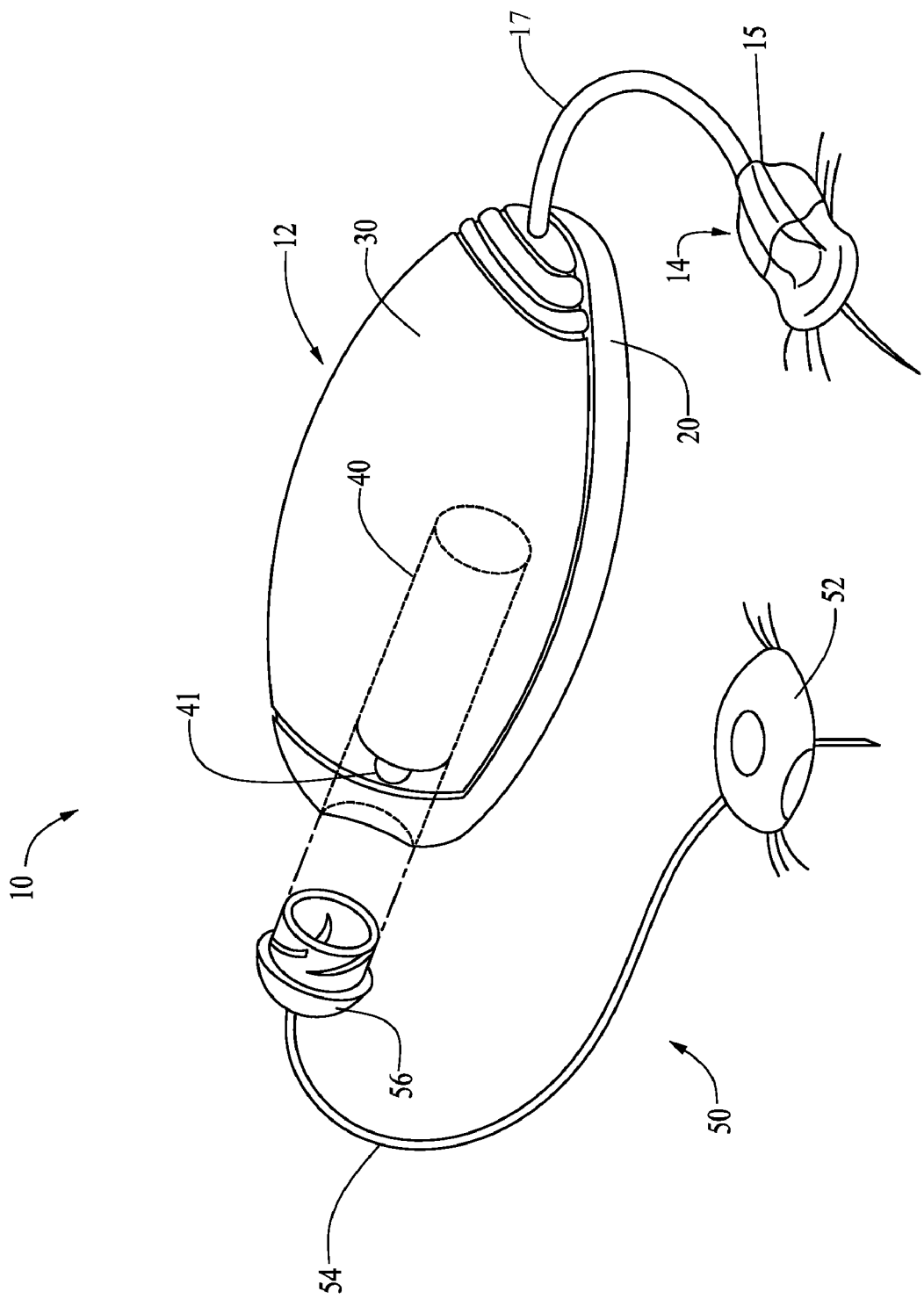
FIG. 2 illustrates an example of a system in accordance with an embodiment of the present invention.

FIG. 2 illustrates an example of the system 10 in accordance with an embodiment of the present invention. The system 10 in accordance with the embodiment illustrated in FIG. 2 includes the delivery device 12 and the sensing device 14. The delivery device 12 in accordance with an embodiment of the present invention may include a disposable housing 20, a durable housing 30, and a reservoir system 40. The delivery device 12 may further include an infusion path 50.

Elements of the delivery device 12 that ordinarily contact the body of a user-patient or that ordinarily contact fluidic media during operation of the delivery device 12 may be considered as a disposable portion of the delivery device 12. For example, a disposable portion of the delivery device 12 may include the disposable housing 20 and the reservoir system 40. The disposable portion of the delivery device 12 may be recommended for disposal after a specified number of uses.

On the other hand, elements of the delivery device 12 that do not ordinarily contact the body of the user-patient or fluidic media during operation of the delivery device 12 may be considered as a durable portion of the delivery device 12. For example, a durable portion of the delivery device 12 may include the durable housing 30, electronics (not shown in FIG. 2), a drive device having a motor and drive linkage (not shown in FIG. 2), and the like. Elements of the durable housing portion of the delivery device 12 are typically not contaminated from contact with the user-patient or fluidic media during normal operation of the delivery device 12 and, thus, may be retained for re-use with replaced disposable portions of the delivery device 12.

In various embodiments, the disposable housing 20 may support the reservoir system 40 and has a bottom surface (facing downward and into the page in FIG. 2) configured to secure to the body of the user-patient. An adhesive may be employed at an interface between the bottom surface of the disposable housing 20 and the skin of the user-patient to adhere the disposable housing 20 to the skin of the user-patient. In various embodiments, the adhesive may be provided on the bottom surface of the disposable housing 20, with a peelable cover layer covering the adhesive material. In this manner, the cover layer may be peeled off to expose the adhesive material, and the adhesive side of the disposable housing 20 may be placed against the user-patient, for example against the skin of the user-patient. Thus in some embodiments, the delivery device 12 may be attached to the skin of the user-patient.

In other embodiments, the disposable housing 20 and/or the remaining portions of the delivery device 12 may be worn or otherwise attached on or underneath clothing of the user-patient. Similarly, the delivery device 12 may be supported by any suitable manner, such as, but not limited to, on a belt, in a pocket, and the like. Representative examples of such delivery devices 12, and delivery devices in general, may include, but is not limited to, the MiniMed Paradigm 522 Insulin Pump, MiniMed Paradigm 722 Insulin Pump, MiniMed Paradigm 515 Insulin Pump, MiniMed Paradigm 715 Insulin Pump, MiniMed Paradigm 512R Insulin Pump, MiniMed Paradigm 712R Insulin Pump, MiniMed 508 Insulin Pump, MiniMed 508R Insulin Pump, and any other derivatives thereof.

The reservoir system 40 may be configured for containing or holding fluidic media, such as, but not limited to insulin. In various embodiments, the reservoir system 40 may include a hollow interior volume for receiving fluidic media, such as, but not limited to, a cylinder-shaped volume, a tubular-shaped volume, or the like. In some embodiments, the reservoir system 40 may be provided as a cartridge or canister for containing fluidic media. In various embodiments, the reservoir system 40 can be refilled with fluidic media. In further embodiments, the reservoir system 40 is pre-filled with fluidic media.

The reservoir system 40 may be supported by the disposable housing 20 in any suitable manner. For example, the disposable housing 20 may be provided with projections or struts (not shown), or a trough feature (not shown), for holding the reservoir system 40. In some embodiments, the reservoir system 40 may be supported by the disposable housing 20 in a manner that allows the reservoir system 40 to be removed from the disposable housing 20 and replaced with another reservoir. Alternatively, or in addition, the reservoir system 40 may be secured to the disposable housing 20 by a suitable adhesive, a strap, or other coupling structure.

In various embodiments, the reservoir system 40 may include at least one port 41 for allowing fluidic media to flow into and/or flow out of the interior volume of the reservoir system 40. In some embodiments, the infusion path 50 may include a connector 56, a tube 54, and a needle apparatus 52. The connector 56 of the infusion path 50 may be connectable to the port 41 of the reservoir system 40. In various embodiments, the disposable housing 20 may be configured with an opening near the port 41 of the reservoir system 40 for allowing the connector 56 of the infusion path 50 to be selectively connected to and disconnected from the port 41 of the reservoir system 40.

In various embodiments, the port 41 of the reservoir system 40 may be covered with or supports a septum (not shown in FIG. 2), such as a self-sealing septum, or the like. The septum may be configured to prevent fluidic media from flowing out of the reservoir system 40 through the port 41 when the septum is not pierced. In addition, in various embodiments, the connector 56 of the infusion path 50 may include a needle for piercing the septum covering the port 41 of the reservoir system 40 to allow fluidic media to flow out of the interior volume of the reservoir system 40.

Examples of needle/septum connectors can be found in U.S. patent application Ser. No. 10/328,393, filed Dec. 22, 2003, entitled "Reservoir Connector," which is incorporated herein by reference in its entirety. In other alternatives, non-septum connectors such as Luer locks, or the like may be used. In various embodiments, the needle apparatus 52 of the infusion path 50 may include a needle that is able to puncture the skin of the user-patient. In addition, in various embodiments, the tube 54 connects the connector 56 with the needle apparatus 52 and may be hollow, such that the infusion path 50 is able to provide a path to allow for the delivery of fluidic media from the reservoir system 40 to the body of a user-patient.

The durable housing 30 of the delivery device 12 in accordance with various embodiments of the present invention includes a housing shell configured to mate with and secure to the disposable housing 20. The durable housing 30 and the disposable housing 20 may be provided with correspondingly shaped grooves, notches, tabs, or other suitable features that allow the two parts to connect together easily, by manually pressing the two housings together, by twist or threaded connection, in a friction fit connection, in a slidable connection, and/or other suitable manner of connecting the parts that is well known in the mechanical arts.

In various embodiments, the durable housing 30 and the disposable housing 20 may be connected to each other using a twist action. The durable housing 30 and the disposable housing 20 may be configured to be separable from each other when a sufficient force is applied to disconnect the two housings from each other. For example, in some embodiments the disposable housing 20 and the durable housing 30 may be snapped together by friction fitting. In various embodiments, a suitable seal, such as an o-ring seal, may be placed along a peripheral edge of the durable housing 30 and/or the disposable housing 20 to provide a seal against water entering between the durable housing 30 and the disposable housing 20.

The durable housing 30 of the delivery device 12 may support a drive device (not shown in FIG. 2) that may include a motor and a drive device linkage portion. The drive device may be configured to apply a force to fluidic media within the reservoir system 40 to force fluidic media out of the reservoir system 40 and into an infusion path, such as the infusion path 50, for delivery to a user-patient. For example, in some embodiments, an electrically-driven motor 84 (refer to FIGS. 5B and 5C) may be mounted within the durable housing 30 with appropriate linkage for operatively coupling the motor 84 to a plunger arm (refer to FIGS. 6A-6C) connected to a plunger head (refer to FIGS. 6A-6C) arranged within the reservoir system 40. The electrically-driven motor may be configured to drive the plunger head in a direction to force fluidic media out of the port 41 of the reservoir system 40 and to the user-patient.

Also, in some embodiments, the motor 84 may be controllable to reverse direction to move the plunger arm 60 and the plunger head to cause fluid to be drawn into the reservoir system 40 from a patient. The motor 84 may be arranged within the durable housing 30 and the reservoir system 40 may be correspondingly arranged on the disposable housing 20, such that the operable engagement of the motor 84 with the plunger head, through the appropriate linkage, occurs automatically upon the user-patient connecting the durable housing 30 with the disposable housing 20 of the delivery device 12. Further examples of linkage and control structures may be found in, but are not limited to, U.S. patent application Ser. No. 09/813,660, filed Mar. 21, 2001, entitled "Control Tabs for Infusion Devices and Methods of Using the Same";

U.S. Patent Pub. No. 2006/0264894 (Ser. No. 11/211,095), filed Aug. 23, 2005, entitled "Infusion Device and Method with Disposable Portion"; U.S. patent application Ser. No. 11/210,467, filed Aug. 23, 2005, entitled "Infusion Device and Method With Drive In Separable Durable Housing Portion"; U.S. patent application Ser. No. 11/211,150, filed Aug. 23, 2005, entitled "Pump Assembly and Method For Infusion Device"; U.S. patent application Ser. No. 11/210,455, filed Aug. 23, 2005, entitled "Reservoir Support And Method For Infusion Device"; and U.S. Pat. No. 6,485,465, filed Mar. 27, 2001, entitled "Methods, Apparatuses, and Uses for Infusion Pump Fluid Pressure and Force Detection," all of which are incorporated herein by reference in its entirety.

In various embodiments, the durable housing 30 and the disposable housing 20 may be made of suitably rigid materials that maintain their shape, yet provide sufficient flexibility and resilience to effectively connect together and disconnect, as described above. The material of the disposable housing 20 may be selected for suitable compatibility with skin. For example, the disposable housing 20 and the durable housing 30 of the delivery device 12 may be made of any suitable plastic, metal, composite material, or the like. The disposable housing 20 may be made of the same type of material or a different material relative to the durable housing 30. In some embodiments, the disposable housing 20 and the durable housing 30 may be manufactured by injection molding or other molding processes, machining processes, or combinations thereof.

For example, the disposable housing 20 may be made of a relatively flexible material, such as a flexible silicone, plastic, rubber, synthetic rubber, or the like. By forming the disposable housing 20 of a material capable of flexing with the skin of a user-patient, a greater level of user-patient comfort may be achieved when the disposable housing 20 is secured to the skin of the user-patient. In addition, a flexible disposable housing 20 may result in an increase in site options on the body of the user-patient at which the disposable housing 20 may be secured.

In the embodiment illustrated in FIG. 2, the delivery device 12 is connected to the sensing device 14 through a connection element 17 of the sensing device 14. The sensing device 14 may include a sensor 15 that includes any suitable biological or environmental sensing device, depending upon a nature of a treatment to be administered by the delivery device 12. For example, in the context of delivering insulin to a diabetes patient, the sensor 15 may include a blood glucose sensor, or the like.

In some embodiments, the sensor 15 may include a continuous glucose sensor. The continuous glucose sensor may be implantable within the body of the user-patient. In other embodiments, the continuous glucose sensor may be located externally, for example on the skin of the user-patient, or attached to clothing of the user-patient. In such embodiments, fluid may be drawn continually from the user-patient and sensed by the continuous glucose sensor. In various embodiments, the continuous glucose sensor may be configured to sense and/or communicate with the CCD 16 continuously. In other embodiments, the continuous glucose sensor may be configured to sense and/or communicate with the CCD 16 intermittently, for example sense glucose levels and transmit information every few minutes. In various embodiments, the continuous glucose sensor may utilize glucose oxidase.

The sensor 15 may be an external sensor that secures to the skin of a user-patient or, in other embodiments, may be an implantable sensor that is located in an implant site within the body of the user-patient. In further alternatives, the sensor may be included with as a part or along side the infusion cannula and/or needle, such as for example as shown in U.S. patent application Ser. No. 11/149,119, filed Jun. 8, 2005, entitled "Dual Insertion Set," which is incorporated herein by reference in its entirety. In the illustrated example of FIG. 2, the sensor 15 is an external sensor having a disposable needle pad that includes a needle for piercing the skin of the user-patient and enzymes and/or electronics reactive to a biological condition, such as blood glucose level or the like, of the user-patient. In this manner, the delivery device 12 may be provided with sensor data from the sensor 15 secured to the user-patient at a site remote from the location at which the delivery device 12 is secured to the user-patient.

While the embodiment shown in FIG. 2 may include a sensor 15 connected by the connection element 17 for providing sensor data to sensor electronics (not shown in FIG. 2) located within the durable housing 30 of the delivery device 12, other embodiments may employ a sensor 15 located within the delivery device 12. Yet other embodiments may employ a sensor 15 having a transmitter for communicating sensor data by a wireless communication link with receiver electronics (not shown in FIG. 2) located within the durable housing 30 of the delivery device 12. In various embodiments, a wireless connection between the sensor 15 and the receiver electronics within the durable housing 30 of the delivery device 12 may include a radio frequency (RF) connection, an optical connection, or another suitable wireless communication link. Further embodiments need not employ the sensing device 14 and, instead, may provide fluidic media delivery functions without the use of sensor data.

As described above, by separating disposable elements of the delivery device 12 from durable elements, the disposable elements may be arranged on the disposable housing 20, while durable elements may be arranged within a separable durable housing 30. In this regard, after a prescribed number of uses of the delivery device 12, the disposable housing 20 may be separated from the durable housing 30, so that the disposable housing 20 may be disposed of in a proper manner. The durable housing 30 may then be mated with a new (unused) disposable housing 20 for further delivery operation with a user-patient.

Figure 3:
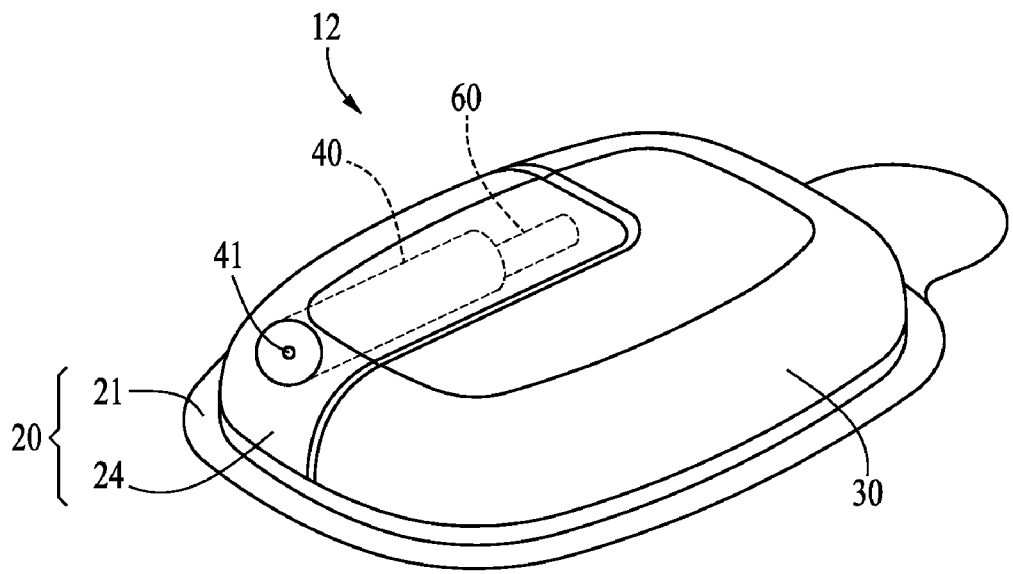
FIG. 3 illustrates an example of a delivery device in accordance with an embodiment of the present invention.

FIG. 3 illustrates an example of the delivery device 12 in accordance with another embodiment of the present invention. The delivery device 12 of the embodiment of FIG. 3 is similar to the delivery device 12 of the embodiment of FIG. 2. While the delivery device 12 in the embodiment illustrated in FIG. 2 provides for the durable housing 30 to cover the reservoir system 40, the delivery device 12 in the embodiment of FIG. 3 provides for the durable housing 30 to secure to the disposable housing 20 without covering the reservoir system 40. The delivery device 12 of the embodiment illustrated in FIG. 3 includes the disposable housing 20, and the disposable housing 20 in accordance with the embodiment illustrated in FIG. 3 includes a base 21 and a reservoir retaining portion 24. In one embodiment, the base 21 and reservoir retaining portion 24 may be formed as a single, unitary structure.

The base 21 of the disposable housing 20 may be configured to be securable to a body of a user-patient. The reservoir-retaining portion 24 of the disposable housing 20 is configured to house the reservoir system 40. The reservoir-retaining portion 24 of the disposable housing 20 may be configured to have an opening to allow for the port 41 of the reservoir system 40 to be accessed from outside of the reservoir-retaining portion 24 while the reservoir system 40 is housed in the reservoir-retaining portion 24. The durable housing 30 may be configured to be attachable to and detachable from the base 21 of the disposable housing 20. The delivery device 12 in the embodiment illustrated in FIG. 3 includes a plunger arm 60 that is connected to or that is connectable to a plunger head (not shown in FIG. 3) within the reservoir system 40.

Figure 4:
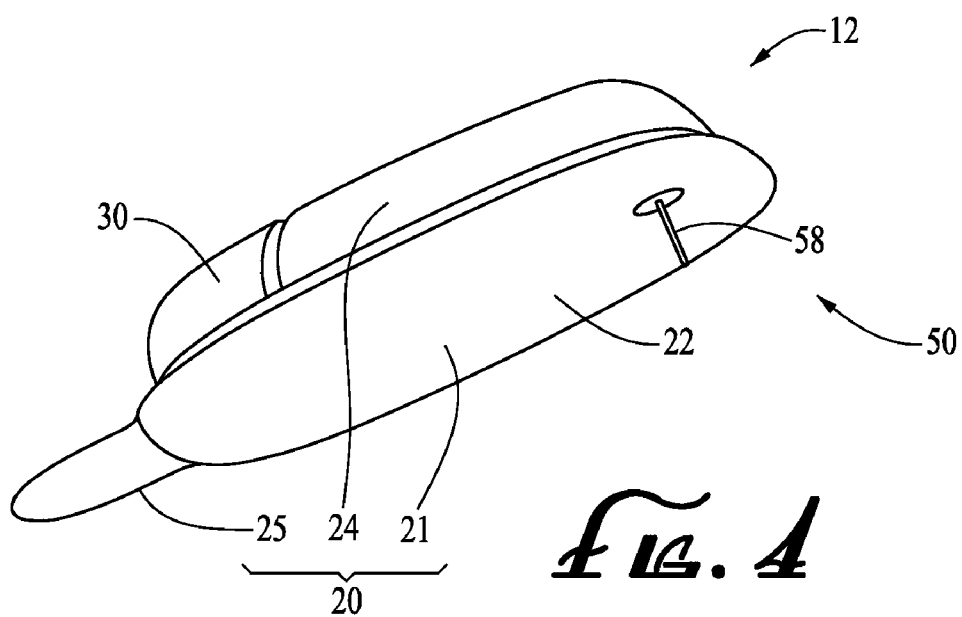
FIG. 4 illustrates a delivery device in accordance with an embodiment of the present invention.

FIG. 4 illustrates another view of the delivery device 12 of the embodiment of FIG. 3. The delivery device 12 of the embodiment illustrated in FIG. 4 includes the disposable housing 20, the durable housing 30, and the infusion path 50. The disposable housing 20 in the embodiment of FIG. 4 includes the base 21, the reservoir-retaining portion 24, and a peelable cover layer 25. The peelable cover layer 25 may cover an adhesive material on the bottom surface 22 of the base 21. The peelable cover layer 25 may be configured to be peelable by a user-patient to expose the adhesive material on the bottom surface 22 of the base 21. In some embodiments, there may be multiple adhesive layers on the bottom surface 22 of the base 21 that are separated by peelable layers.

The infusion path 50 in accordance with the embodiment of the present invention illustrated in FIG. 4 includes the needle 58 rather than the connector 56, the tube 54, and the needle apparatus 52 as shown in the embodiment of FIG. 2. The base 21 of the disposable housing 20 may be provided with an opening or pierceable wall in alignment with a tip of the needle 58, to allow the needle 58 to pass through the base 21 and into the skin of a user-patient under the base 21, when extended. In this manner, the needle 58 may be used to pierce the skin of the user-patient and deliver fluidic media to the user-patient.

Alternatively, the needle 58 may be extended through a hollow cannula (not shown in FIG. 4), such that upon piercing the skin of the user-patient with the needle 58, an end of the hollow cannula is guided through the skin of the user-patient by the needle 58. Thereafter, the needle 58 may be removed, leaving the hollow cannula in place with one end of the cannula located within the body of the user-patient and the other end of the cannula in fluid flow connection with fluidic media within the reservoir system 40. Accordingly, fluidic media may be conveyed from the reservoir system 40 to the body of the user-patient.

Figure 5A:
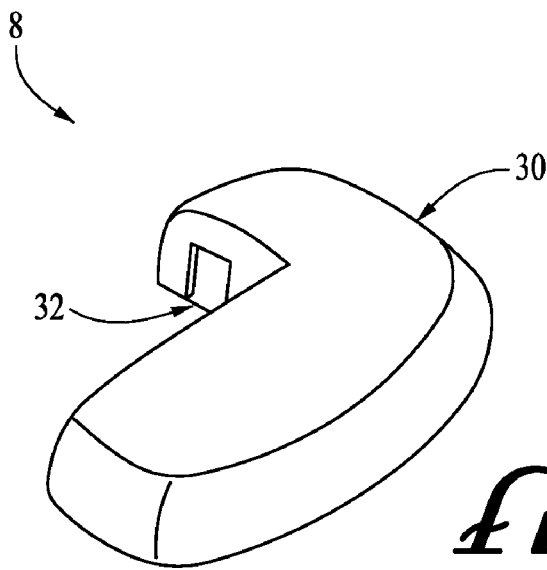
FIG. 5A illustrates a durable portion of a delivery device in accordance with an embodiment of the present invention.
Figure 5B:
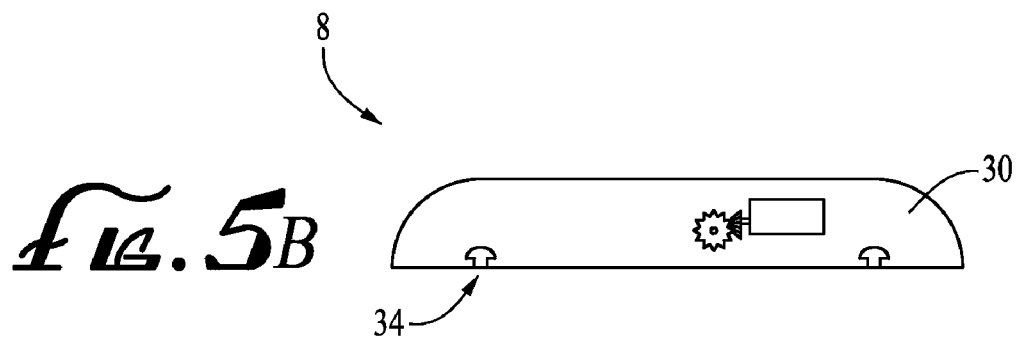
FIG. 5B illustrates a section view of a durable portion of a delivery device in accordance with an embodiment of the present invention.
Figure 5C:
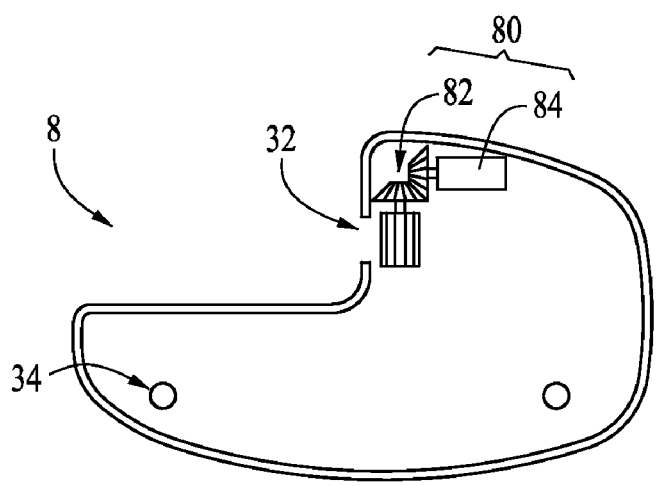
FIG. 5C illustrates a section view of a durable portion of a delivery device in accordance with an embodiment of the present invention.

FIG. 5A illustrates a durable portion 8 of the delivery device 12 (e.g., FIG. 3) in accordance with an embodiment of the present invention. FIG. 5B illustrates a section view of the durable portion 8 in accordance with an embodiment of the present invention. FIG. 5C illustrates another section view of the durable portion 8 in accordance with an embodiment of the present invention. With reference to FIGS. 5A, 5B, and 5C, in various embodiments, the durable portion 8 may include the durable housing 30, and a drive device 80. The drive device 80 may include a motor 84 and a drive device linkage portion 82.

In various embodiments, the durable housing 30 may include an interior volume for housing the motor 84, the drive device linkage portion 82, other electronic circuitry, and a power source (not shown in FIGS. 5A, 5B, and 5C). In addition, in various embodiments, the durable housing 30 may be configured with an opening 32 for receiving a plunger arm 60 (refer to FIG. 3). In addition, in various embodiments, the durable housing 30 may include one or more connection members 34, such as tabs, insertion holes, or the like, for connecting with the base 21 of the disposable housing 20 (e.g., FIG. 3).

Figure 6A:
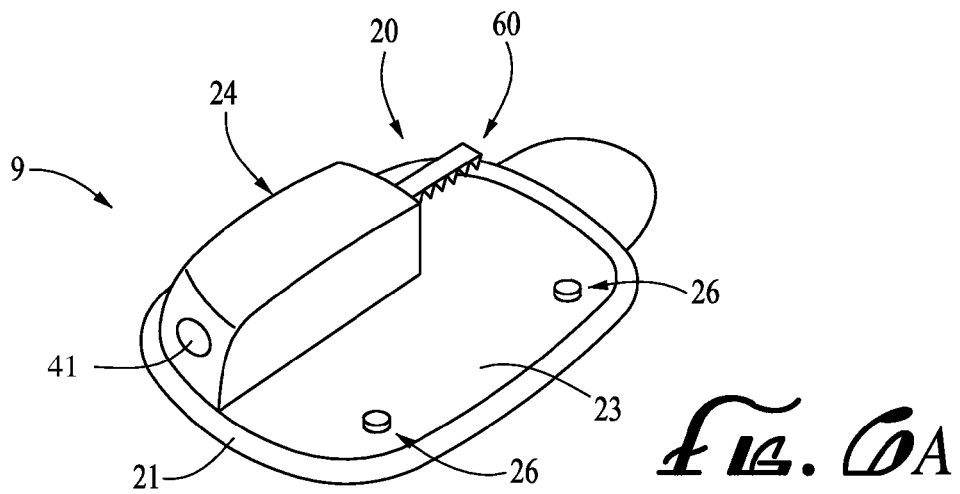
FIG. 6A illustrates a disposable portion of a delivery device in accordance with an embodiment of the present invention.
Figure 6B:
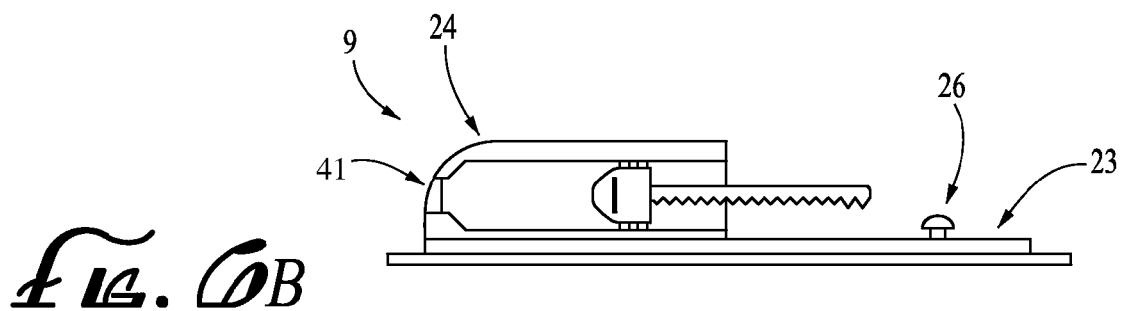
FIG. 6B illustrates a section view of a disposable portion of a delivery device in accordance with an embodiment of the present invention.
Figure 6C:
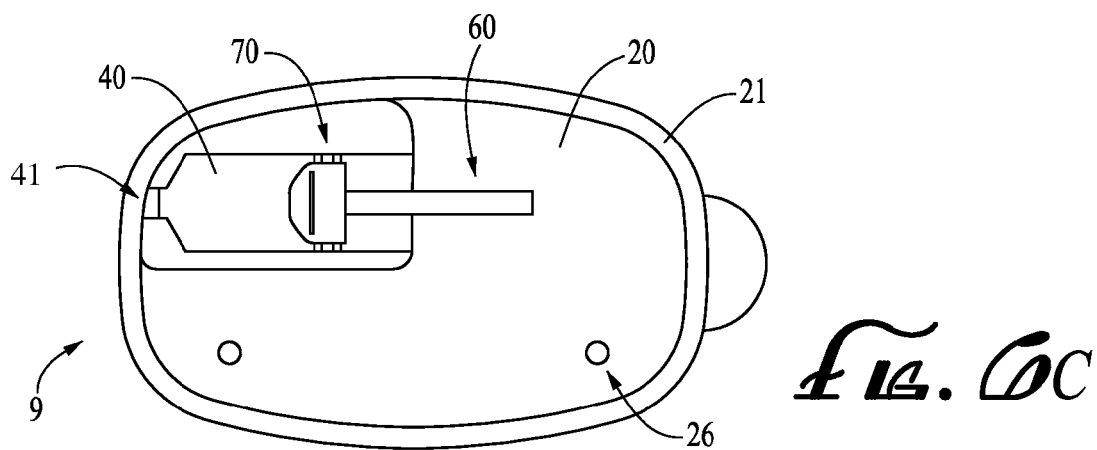
FIG. 6C illustrates a section view of a disposable portion of a delivery device in accordance with an embodiment of the present invention.

FIG. 6A illustrates a disposable portion 9 of the delivery device 12 (e.g., FIG. 3) in accordance with an embodiment of the present invention. FIG. 6B illustrates a section view of the disposable portion 9 in accordance with an embodiment of the present invention. FIG. 6C illustrates another section view of the disposable portion 9 in accordance with an embodiment of the present invention. With reference to FIGS. 6A, 6B, and 6C, in various embodiments, the disposable portion 9 includes the disposable housing 20, the reservoir system 40, the plunger arm 60, and a plunger head 70. The plunger head 70 may be made of Bromobutyl rubber, silicone rubber, or any other suitable material and/or any derivative thereof. In some embodiments, the disposable housing 20 may include the base 21 and the reservoir-retaining portion 24. In various embodiments, the base 21 may include a top surface 23 having one or more connection members 26, such as tabs, grooves, or the like, for allowing connections with the one or more connection members 34 of embodiments of the durable housing 30 (e.g., FIG. 5B).

In various embodiments, the reservoir system 40 may be housed within the reservoir retaining portion 24 of the disposable housing 20, and the reservoir system 40 may be configured to hold fluidic media. In addition, in various embodiments, the plunger head 70 may be disposed at least partially within the reservoir system 40 and may be moveable within the reservoir system 40 to allow fluidic media to fill into the reservoir system 40 and to force fluidic media out of the reservoir system 40. In some embodiments, the plunger arm 60 may be connected to or is connectable to the plunger head 70.

Also, in some embodiments, a portion of the plunger arm 60 may extend to outside of the reservoir-retaining portion 24 of the disposable housing 20. In various embodiments, the plunger arm 60 may have a mating portion for mating with the drive device linkage portion 82 of the drive device 80 (e.g., FIG. 5C). With reference to FIGS. 5C and 6C, in some embodiments, the durable housing 30 may be snap fitted onto the disposable housing 20, whereupon the drive device linkage portion 82 automatically engages the mating portion of the plunger arm 60.

When the durable housing 30 and the disposable housing 20 are fitted together with the drive device linkage portion 82 engaging or mating with the plunger arm 60, the motor 84 may be controlled to drive the drive device linkage portion 82. Accordingly, the plunger arm 60 may be moved to cause the plunger head 70 to move within the reservoir system 40. When the interior volume of the reservoir system 40 is sufficiently filled with fluidic media and an infusion path is provided from the reservoir system 40 to the body of the user-patient, the plunger head 70 may be moved within the reservoir system 40 to force fluidic media from the reservoir system 40 to the user-patient via the infusion path.

In various embodiments, once the reservoir system 40 has been sufficiently emptied or otherwise requires replacement, the user-patient may simply remove the durable housing 30 from the disposable housing 20, and replace the disposable portion 9, including the reservoir system 40, with a new disposable portion having a new reservoir. The durable housing 30 may be connected to the new disposable housing of the new disposable portion, and the delivery device including the new disposable portion may be secured to the skin of a user-patient, or otherwise attached to the user-patient.

In various other embodiments, rather than replacing the entire disposable portion 9 every time the reservoir system 40 is emptied, the reservoir system 40 may be refilled with fluidic media. In some embodiments, the reservoir system 40 may be refilled while remaining within the reservoir retaining portion 24 (e.g., FIG. 6B) of the disposable housing 20. In addition, in various embodiments, the reservoir system 40 may be replaced with a new reservoir (not shown), while the disposable housing 20 may be re-used with the new reservoir. In such embodiments, the new reservoir may be inserted into the disposable portion 9.

With reference to FIGS. 3, 5A, 6B, and 6C, in various embodiments, the delivery device 12 may include reservoir status circuitry (not shown), and the reservoir system 40 may include reservoir circuitry (not shown). In various embodiments, the reservoir circuitry stores information such as, but not limited to, at least one of (i) an identification string identifying the reservoir system 40; (ii) a manufacturer of the reservoir system 40; (iii) contents of the reservoir system 40; (iv) an amount of contents in the reservoir system 40; or the like. In some embodiments, the delivery device 12 may include the reservoir status circuitry, and the reservoir status circuitry may be configured to read data from the reservoir circuitry when the reservoir system 40 is inserted into the disposable portion 9.

In various embodiments, the reservoir status circuitry may be further configured to store data to the reservoir circuitry after at least some of the contents of the reservoir system 40 have been transferred out of the reservoir system 40 to update information in the reservoir circuitry. Such information may be related to, but is not limited to, an amount of fluidic media remaining in the reservoir system 40, an amount of fluidic media already delivered, plunger head 60 location, pressure within the reservoir system, or the like.

In some embodiments, the reservoir status circuitry may be configured to store data to the reservoir circuitry to update information in the reservoir circuitry related to an amount of contents remaining in the reservoir system 40 when the reservoir system 40 is inserted into the disposable portion 9. In some embodiments, the delivery device 12 may include the reservoir status circuitry and the reservoir system 40 may include the reservoir circuitry, and the reservoir status circuitry may selectively inhibit use of the delivery device 12 or may selectively provide a warning signal based on information read by the reservoir status circuitry from the reservoir circuitry.

In various embodiments, any of the connection structure described above for allowing one or more parts of the delivery device to be selectively connectable to and separable from one or more other parts of the delivery device may include one or more elements as will be described. The element(s) may function to provide one or more of aligning connectable parts, connection of connectable parts, and sensing the connection of connectable parts, as will be described.

FIGS. 7-15B illustrate a medical device system 100 according to various embodiments of the present invention. The medical device system 100 may include features similar to the medical device systems discussed throughout the disclosure or employed as an embodiment of the medical devices (e.g., delivery device 12 in FIGS. 1-6C) discussed throughout the disclosure. Although the medical device system 100 may include features similar or used with the embodiments of FIGS. 1-6C, it should be understood that the medical device system 100 may also include some or all of the same features and operate in a manner similar to that shown and described in the embodiments of FIGS. 16-32B. In addition, some or all of the features shown in FIGS. 1-6C and 16-32B may be combined in various ways and included in the embodiments shown in FIGS. 7-15B. Likewise, it should be understood that any of the features of the embodiments of FIGS. 7-15B may be combined or otherwise incorporated into any of the other embodiments of FIGS. 7-15B as well as any other embodiment herein discussed.

A generalized representation of a first part 101 and a second part 102 of a medical device system 100, such as, but not limited to the delivery device 12 in FIGS. 1-6C as described above, is shown in FIG. 7. The first part 101 and the second part 102 may be configured to be connectable to each other or to be otherwise operatively engageable with each other. In some embodiments, a connection structure may be provided to secure the first part 101 and the second part 102 together for operation of the medical device system 100.

In further embodiments, the connection structure may include a magnetic structure for connecting the first part 101 and the second part 102. For example, a magnet may be provided on one of the first part 101 and the second part 102 and a magnetically attractive material, such as a magnet of opposite polarity, a metal, and/or the like may be provided on the other of the first part 101 and the second part 102. Such an example as well as other examples are disclosed in, but are not limited to, U.S. patent application Ser. No. 11/759,725, entitled "Infusion Medium Delivery Device and Method with Drive Device for Driving Plunger in Reservoir," herein incorporated by reference in its entirety.

Various embodiments, additionally or alternatively, may include other suitable structural features to aid in connecting the first part 101 and the second part 102. These may include, but are not limited to, adhesives, snap-fit structures, friction-fit structures, and/or the like on the first part 101 and/or the second part 102 that abut as the first part 101 and the second part 102 are brought together for connection. Other examples of various connection structures can be found, but are not limited to, U.S. patent application Ser. No. 12/553,038, filed Sep. 2, 2009, entitled "Insertion Device Systems and Methods," herein incorporated by reference in their entirety.

The first part 101 and the second part 102 may each be one of two housing portions, such as, but not limited to, a durable housing portion 30 (e.g., FIGS. 1-6C) and a disposable housing portion 20 (e.g., FIGS. 1-6C), as previously described. As previously discussed with respect to FIGS. 1-6C, the durable housing portion 30 may include various components, such as, but not limited to, a drive device 80, drive motor 84, drive device linkage portion 82, and/or the like. The disposable housing portion 20 may include various components, such as, but not limited to, a reservoir system 40. Returning to FIG. 7, alternatively, one of the first part 101 and the second part 102 may be a base portion 21 (e.g., FIGS. 1-6C) and the other of the first part 101 and the second part 102 may be a housing portion such as, but not limited to, the durable housing portion 30 and/or the disposable housing portion 20. In some embodiments, one of the housing portions may be a reservoir system 40 (e.g., FIGS. 1-6C).

In further embodiments, the medical device system 100 may include more than two housing portions. For example, such embodiments may include, but are not limited to, a durable housing portion 30, a disposable housing portion 20, and a base portion 21. Other housing portions may include, but are not limited to, an insertion device, electronics, and/or the like.

In some embodiments, one of the medical device system 100 parts (e.g., 101 in FIG. 7) may be provided with a first interactive element 104. The other medical device system 100 part (e.g., 102 in FIG. 7) may be provided with a second interactive element 106. The first interactive element 104 and the second interactive element 106 may be configured to interact with each other when in sufficiently close proximity to each other.

The first interactive element 104 may be arranged in a fixed relation to the first part 101, for example, by attaching, forming, or otherwise supporting the first interactive element 104 to a suitable location on a wall or on other structure of or in the first part 101. The second interactive element 106 may be arranged in a fixed relation to the second part 102, for example, by attaching, forming, or otherwise supporting the second interactive element 106 to a suitable location on a wall or on other structure of or in the second part 102. In some embodiments, the second interactive element 106 may be arranged on the second part 102 to be relative to the first interactive element 104 on the first part 101 in a case where the first part 101 and the second part 102 are connected or otherwise operatively engaged and the first part 101 and the second part 102 are properly aligned. Accordingly, the first interactive element 104 and the second interactive element 106 may be aligned. As such, the first interactive element 104 and the second interactive element 106, for example, may interact with each other in a case where the first part 101 and the second part 102 are connected or otherwise operatively engaged and the first interactive element 104 and the second interactive element 106 are properly aligned.

An interaction between the first interactive element 104 and the second interactive element 106 (or between any other interactive element discussed throughout the disclosure) may occur in a case where the first part 101 and the second part 102 are operatively engaged properly or otherwise brought into a pre-defined, sufficiently aligned position and/or in a pre-defined, sufficiently close proximity. The predefined aligned position and/or proximity, for example, may correspond to a properly aligned and mutually proximate position for connection of the first part 101 and the second part 102 for operation. It should be understood that with respect to the embodiments described throughout the disclosure, operatively engaged may include connected and/or aligned, unless otherwise specified. Likewise, operatively engaged (and/or connected and/or aligned) may include operatively engaged properly (and/or connected properly and/or aligned properly), unless otherwise specified.

In various embodiments, the first interactive element 104 and the second interactive element 106 may be similar types of devices. For instance, in some embodiments, the first interactive element 104 may be configured to interact with second interactive elements (e.g., the second interactive element 106) and/or the second interactive element 106 may be configured to interact with first interactive elements (e.g., the first interactive element 104). For example, a first interactive element 104 may be a magnet arranged to provide an N (north) polarity and a second interactive element 106 may be a magnet arranged to provide an S (south) polarity. The first interactive element 104 may interact more effectively (e.g., connect and/or align) with the second interactive element 106 than with another first interactive element 104 arranged to provide an N polarity.

In various embodiments, the first interactive element 104 may be configured to interact with second interactive elements (e.g., the second interactive element 106), as well as other first interactive elements (e.g., first interactive element 104' (e.g., FIG. 8 discussed below)). In some embodiments, the second interactive element 106 may be configured to interact with first interactive elements (e.g., the first interactive element 104), as well as other second interactive elements (e.g., second interactive element 106' (e.g., FIG. 8 discussed below)).

In some embodiments, the first interactive element 104 and the second interactive element 106 may be dissimilar types of mechanisms. For example, a first interactive element 104 may be a ferrous conduit and a second interactive element 106 may be a magnet. The second interactive element 106 may interact with (e.g., connect and/or align) the first interactive element 104, as well as other magnetic second interactive elements 106. As another example, as described below with respect to, for example FIGS. 15A and 15B, first interactive element 204 may be a protrusion, pusher, finger, or other structural feature configured and/or arranged to act upon (e.g., urge) a second interactive element 206', and/or the like that may be for interacting with (e.g., functioning as a conductor for) another second interactive element 206.

Returning to FIG. 7, in some embodiments, suitable electronics may be connected to the first interactive element 104 and/or the second interactive element 106 to provide a controlled power signal to selectively activate or otherwise control one or more of the first interactive element 104 and the second interactive element 106 and/or other components as described throughout the disclosure.

In various embodiments, some or all of the interactive elements (e.g., first interactive element 104, second interactive element 106) may be integrated with the first part 101 and the second part 102 and/or be separate components placed in or on the first part 101 and the second part. For example, the interactive elements may be placed in or on the first part 101 and the second part 102 in a friction-fitting manner, during a molding a process, and/or the like. In some embodiments, one or more of the interactive elements may be insert mold labeled on its respective part. In some embodiments, a film cover may be provided for supporting one or more of the interactive elements.

In various embodiments, some or all of the interactive elements may have an exposed surface. The exposed surface of the interactive elements may be for allowing increased interactivity between each of the interactive elements, for example to allow a user to locate the interactive elements (e.g., to facilitate connection of the first part 101 and the second part 102), and/or the like. In other embodiments, some or all of the interactive elements may be covered, for example (but not limited to) being disposed completely within the first part 101 and/or the second part 102. Such embodiments may allow for protecting the interactive elements from damage, debris collection, mitigating interference with other components (e.g., other interactive elements, electronics in the medical device system 100, and/or the like), and/or the like.

In various embodiments, the first interactive element 104 and the second interactive element 106 may be properly aligned such as, but not limited to, when the first interactive element 104 and the second interactive element 106 align in one dimension or more than one dimension, are sufficiently proximate to each other, contact each other, an electrical or magnetic connection is established between the components, and/or the like. Any one or combination of these events may occur, for example, in a case where the first part 101 and the second part 102 are operatively engaged and positioned relative to each other in a predetermined manner. In other words, the first part 101 and the second part 102 have been connected sufficiently properly and/or otherwise within an operating threshold.

In other embodiments, the first interactive element 104 may be arranged on the first part 101 at a location to interact electronically (or magnetically) with the second interactive element 106 in a case where the first part 101 and the second part 102 are brought together and the first interactive element 104 and the second interactive element 106 are in relative close proximity to each other, such as, but not limited to, in contact with each other. In some embodiments, suitable electronics may be connected to at least one of the first interactive element 104 and the second interactive element 106 to provide a controlled power signal to selectively activate or otherwise control the first interactive element 104 and/or the second interactive element 106.

In some embodiments, such as the embodiment exemplified in FIG. 8, multiple pairs of first interactive elements and second interactive elements may be provided on the first part 101 and the second part 102, for example, to provide a more reliable alignment between the first part 101 and the second part 102. In the illustrated embodiment, a second pair of interactive elements including a first interactive element 104' and a second interactive element 106' are shown as supported by the first part 101 and the second part 102 respectively in a manner similar to that described above for the first interactive element 104 and the second interactive element 106. In further embodiments, more than two pairs of interactive elements may be supported by the first part 101 and the second part 102, as previously described.

In various embodiments, the first interactive element 104 and the first interactive element 104' (and/or the second interactive element 106 and the second interactive element 106') may be dissimilar from each. For instance, in some embodiments, the first interactive element 104 may be configured to interact with second interactive elements (e.g., the second interactive element 106) and/or the first interactive element 104' may be configured to interact with second interactive elements (e.g., the second interactive element 106). For example, a first interactive element 104 may be a magnet arranged to provide an N (north) polarity and a second interactive element 106 may be a magnet arranged to provide an S (south) polarity. A first interactive element 104' may be a magnet arranged to provide an S (south) polarity and a second interactive element 106' may be a magnet arranged to provide an N (north) polarity. Thus, the first interactive element 104 may interact in a more mutually attracting manner (e.g., to connect and/or align) with the second interactive element 106 than the second interactive element 106'. Similarly, the first interactive element 104' may interact in a more mutually attracting manner (e.g., to connect and/or align) with the second interactive element 106' than the second interactive element 106.

Moreover, for instance, in some embodiments, the first interactive element 104 may be configured to interact with second interactive elements (e.g., the second interactive element 106), as well as other first interactive elements (e.g., first interactive element 104'). In some embodiments, the second interactive element 106 may be configured to interact with the first interactive elements (e.g., the first interactive element 104), as well as other second interactive elements (e.g., second interactive element 106'). For example, a first interactive element 104 may be a ferrous conduit and a second interactive element 106 may be a magnet. The second interactive element 106 may interact with (e.g., connect and/or align) the first interactive element 104 as well as other magnetic second interactive elements 106'.

In some embodiments, the first interactive element 104 and the first interactive element 104' and/or the second interactive element 106 and the second interactive element 106' may be dissimilar types of mechanisms. For example, as described with respect to, for example FIGS. 15A and 15B, a first interactive element 104 may be a protrusion, pusher, finger, or other structural feature configured and/or arranged to act upon (e.g., urge) a second interactive element 106' and/or the like arranged and/or configured to interact with (e.g., function as a conductive medium) a second interactive element 106.

With reference to FIG. 7, thus in various embodiments, as part of a process of assembling a first part 101 and a second part 102 of a medical device system 100, a user may bring the first part 101 and the second part 102 together to operatively engage each other or otherwise be in sufficiently close proximity. Accordingly, a first interactive element 104 and a second interactive element 106 (and/or a first interactive element 104' and a second interactive element 106') may be interactable with each other to determine, for example, whether the first part 101 and the second part 102 have been properly aligned.

In some embodiments, the interactive elements (e.g., first interactive element 104, first interactive element 104', second interactive element 106, and second interactive element 106') may be configured to help a user-patient align the first part 101 and the second part 102 relative to each other for proper connection. For example, one or more pairs of interactive element 104, 106, 104', and/or 106' may be arranged at one or more appropriate locations on the first part 101 and the second part 102 to allow an indicator or indicator device 420 (e.g., FIG. 33) associated with the medical device system 100 to provide an indication that the first part 101 and the second part 102 are properly aligned in one or more dimensions relative to each other. Alternatively or in addition, one or more pairs of interactive element 104, 106, 104', and/or 106' may be of suitable size(s), shape(s), orientation(s), and position(s) to allow an indicator associated with the medical device system 100 to provide an indication that the first part 101 and the second part 102 are properly aligned in one or more dimensions relative to each other. For example, the indicator may provide an indication that the first part 101 and the second part 102 are properly connected in a case where the first interactive element 104 and the second interactive element 106 interact.

Figure 9:
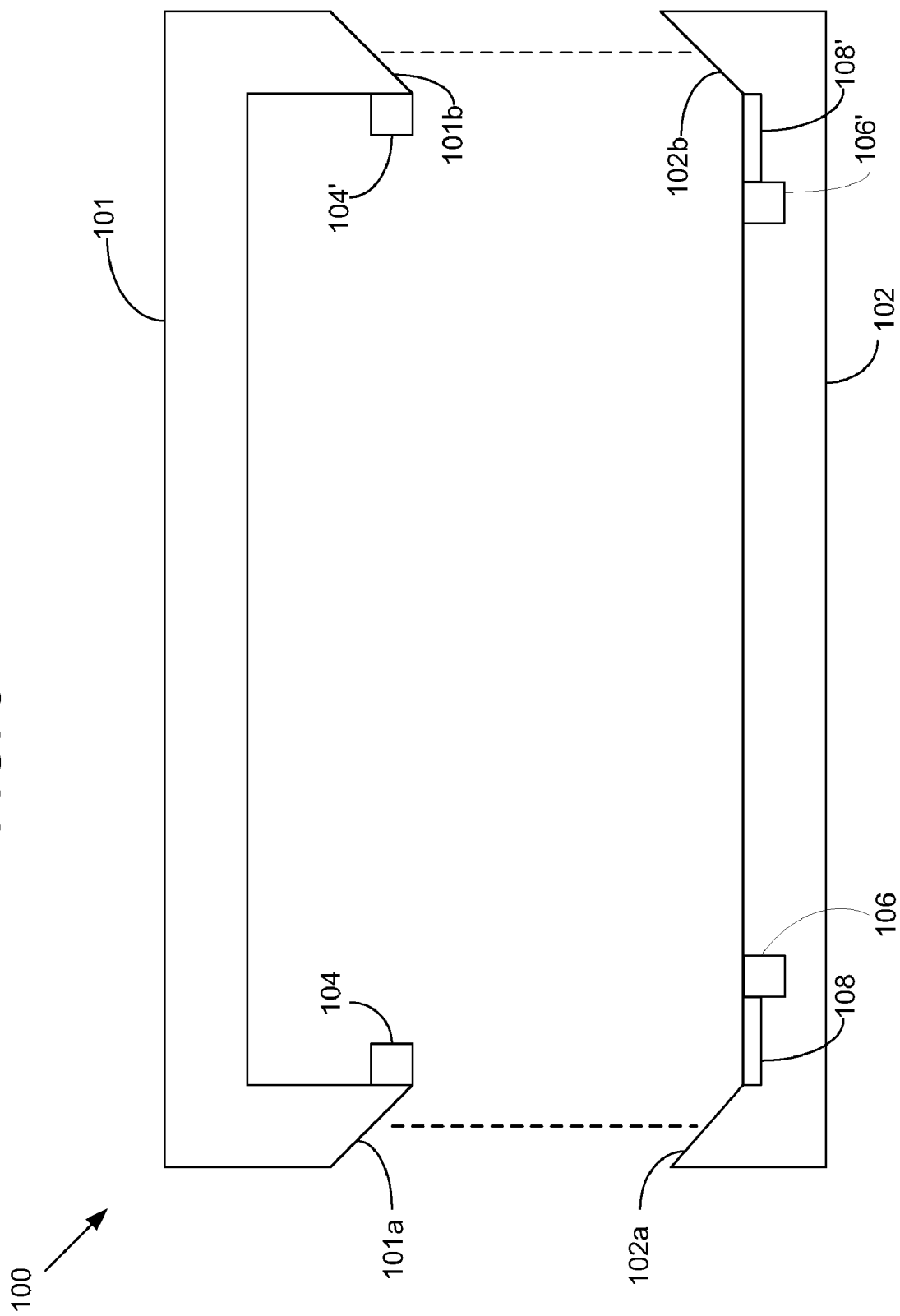
FIG. 9 illustrates a medical device system in accordance with an embodiment of the present invention.

In some embodiments, such as the embodiment exemplified in FIG. 9, a conductive medium 108 may be at a position adjacent one of the interactive element(s) (e.g., the second interactive element 106 in FIG. 9) or otherwise in communication with the interactive element to allow the conductive medium 108 to function as a conductor for the interactive element. In such embodiments, the interactive element may interact with the conductive medium 108 to allow the conductive medium 108 to be have similar characteristics or properties, though not necessarily exactly the same characteristics or properties. For example, a magnetic second interactive element 106 may provide a magnetic charge to a magnetic conductive medium 108. The conductive medium 108 may be made of a material, such as, but not limited to, an electrically conductive material (e.g., metal, graphite, salt solutions, plasma, and/or the like), a magnetically attractive material (e.g., metal), and/or the like. In some embodiments, the conductive medium 108 may be a sufficiently high thermally conductive material (e.g., metal, or any other material with a thermal conductivity, for example (but not limited to), above 1), and/or the like.

In further embodiments, the conductive medium 108 may be arranged on its respective part (e.g., the second part 102 in FIG. 9) to allow the interactive element (e.g., the second interactive element 106 in FIG. 9) to be interactable with the other interactive element (e.g., the first interactive element 104 in FIG. 9) on the opposing part (e.g., the first part 101 in FIG. 9) via the conductive medium 108 in any of the manners described throughout the disclosure. For example, in particular embodiments, the first interactive element 104 may interact with the conductive medium 108 in a case where the first part 101 and the second part 102 are operatively engaged properly. Accordingly, the first interactive element 104 and the second interactive element 106 may be interactable with each other via the conductive medium 108. Thus, some embodiments may allow the first interactive element 104 to interact with the conductive medium 108 in addition to or alternative to the second interactive element 106. For example, a magnetic second interactive element 106 may magnetize a magnetically attractive conductive medium 108, which may then interact with the first interactive element 104.

In some embodiments, the conductive medium 108 may be arranged at a position adjacent the other interactive element (e.g., the first interactive element 104) or otherwise in communication with the other interactive element to allow the conductive medium 108 to function as a conductor for the other interactive element. In further embodiments, the conductive medium 108 may be arranged on its respective part to allow the other interactive element to be interactable with the interactive element (e.g., the second interactive element 106) on the opposing part via the conductive medium 108 in any of the manners described throughout the disclosure. For example, in particular embodiments, the second interactive element 106 may interact with the conductive medium 108 in a case where the first part 101 and the second part 102 are operatively engaged properly. Accordingly, the first interactive element 104 and the second interactive element 106 may be interactable with each other via the conductive medium 108. Thus, some embodiments may allow for the second interactive element 106 to interact with the conductive medium 108 in addition to or alternative to the first interactive element 106. For example, an electrical connection between the first interactive element 104 and the second interactive element 106 may be established by contacting the conductive medium 108 (e.g., electrically conductive medium).

In some embodiments, the indicator may be configured to provide an indication corresponding to a type of alignment, for example, that a maximum alignment or a minimum required alignment has been achieved between the first interactive element 104 and the second interactive element 106 during connection of the first part 101 and the second part 102. In some embodiments, the indicator may be configured to provide an indication corresponding to various stages of alignment, for example, no alignment, alignment in one or more axes and misalignment in one or axes, complete alignment, and/or misalignment after alignment, and/or the like.

In various embodiments, additional structural features may be provided on one or both of the first part 101 and the second part 102 to provide a mechanical alignment function. Such additional structural features may include a first sloped surface 101a on the first part 101 arranged to mate or otherwise engage a corresponding sloped surface 102a on the second part 102. As the first part 101 and the second part 102 are brought together, a misalignment of the first part 101 and the second part may result in the first sloped surface 101a and the second sloped surface 102a engaging each other. Accordingly, the first sloped surface 101a and the second sloped surface 102 may engage each other in a position at which the first sloped surface 101a and the second sloped surface 102a may slide relative to each other toward a proper alignment position.

In some embodiments, multiple pairs of sloped surfaces may be provided on the first part 101 and the second part 102, for example, to provide alignment in one or more directions and/or one or more dimensions. For example, in some embodiments, such as the embodiment exemplified in FIG. 8, the first part 101 and the second part 102 may include a second pair of sloped surfaces including a first sloped surface 101b and a second sloped surface 102b in a manner similar to that described above for the first sloped surface 101a and the second sloped surface 102a. The second pair of sloped surfaces may have a similar or different size and/or shape than the first part of sloped surfaces.

In some embodiments, such as the embodiments exemplified in FIGS. 10A and 10B, at least one of the first part 101 and the second part 102 may include one or more sloped surfaces arranged to mate with corresponding sloped surfaces on the other of the first part 101 and the second part 102. In such embodiments, at least one of the one or more sloped surfaces may be mated with one or more of the plurality of corresponding sloped surfaces so that the first part 101 and the second part 102 can be aligned and/or connected in multiple orientations.

In further embodiments, some or all of the interacting components, such as the first interactive element 104 and the second interactive element 106, may be arranged along the first part 101 and the second part 102 to allow the first part 101 and the second part 102 to be connected and/or aligned in multiple orientations. For example, in FIGS. 10A and 10B, the second part 102 may include multiple sets of second interactive elements 106 and multiple sets of second interactive elements 106', thus allowing the first interactive element 104 to be selectively aligned with any of the second interactive elements 106 while allowing the first interactive element 104' to be aligned with at least one of the second interactive elements 106'. As such, the first part 101 and the second part 102 can be aligned and/or connected in at least a first orientation (e.g., FIG. 10A) and a second orientation (e.g., FIG. 10B). As another example, the first part 101 may include multiple sets of first interactive elements 106 and multiple sets of first interactive elements 104' for allowing selective alignment with the second interactive element 106 and the second interactive element 106', respectively.

Figure 11:
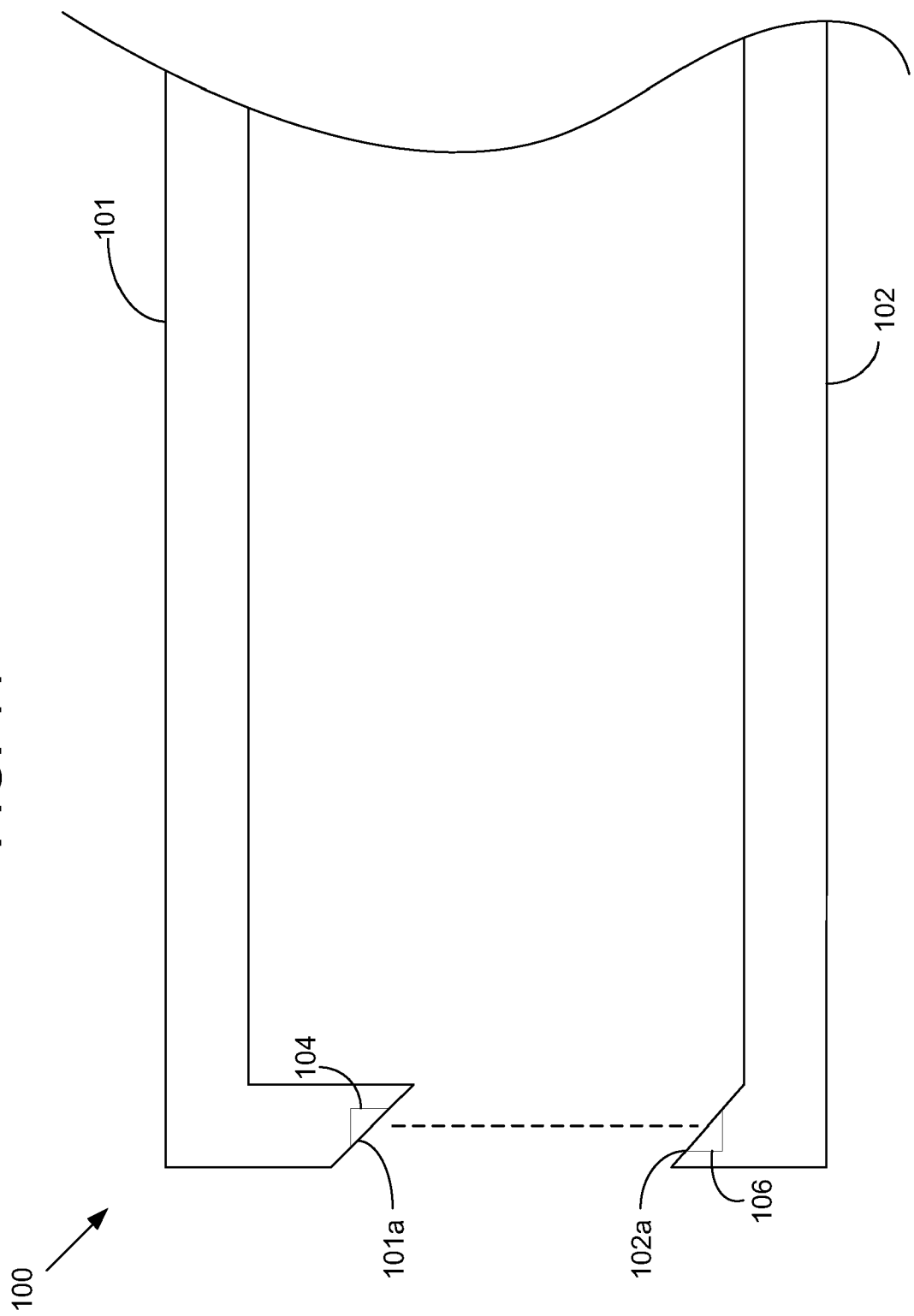
FIG. 11 illustrates a medical device system in accordance with an embodiment of the present invention.

In some embodiments, such as the embodiment exemplified in FIG. 11, the interactive elements (e.g., first interactive element 104, first interactive element 104', second interactive element 106, second interactive element 106', and/or the like) may be supported and/or be part of the sloped surfaces 101a, 102a to provide an alignment and connection function as described throughout the disclosure. Various embodiments may additionally or alternatively include other suitable structural features to aid in the alignment, including, but not limited to, curved or stepped surfaces, rollers and/or the like on the first part 101 and the second part 102 that abut as the first part 101 and the second part 102 are brought together for connection. In some embodiments, one or both of the first part 101 and the second part 102 may include a magnetic connection and/or alignment structure, such as that disclosed in U.S. patent application Ser. No. 11/759,725 entitled "Infusion Medium Delivery Device and Method with Drive Device for Driving Plunger in Reservoir," herein incorporated by reference in its entirety.

Figure 12:
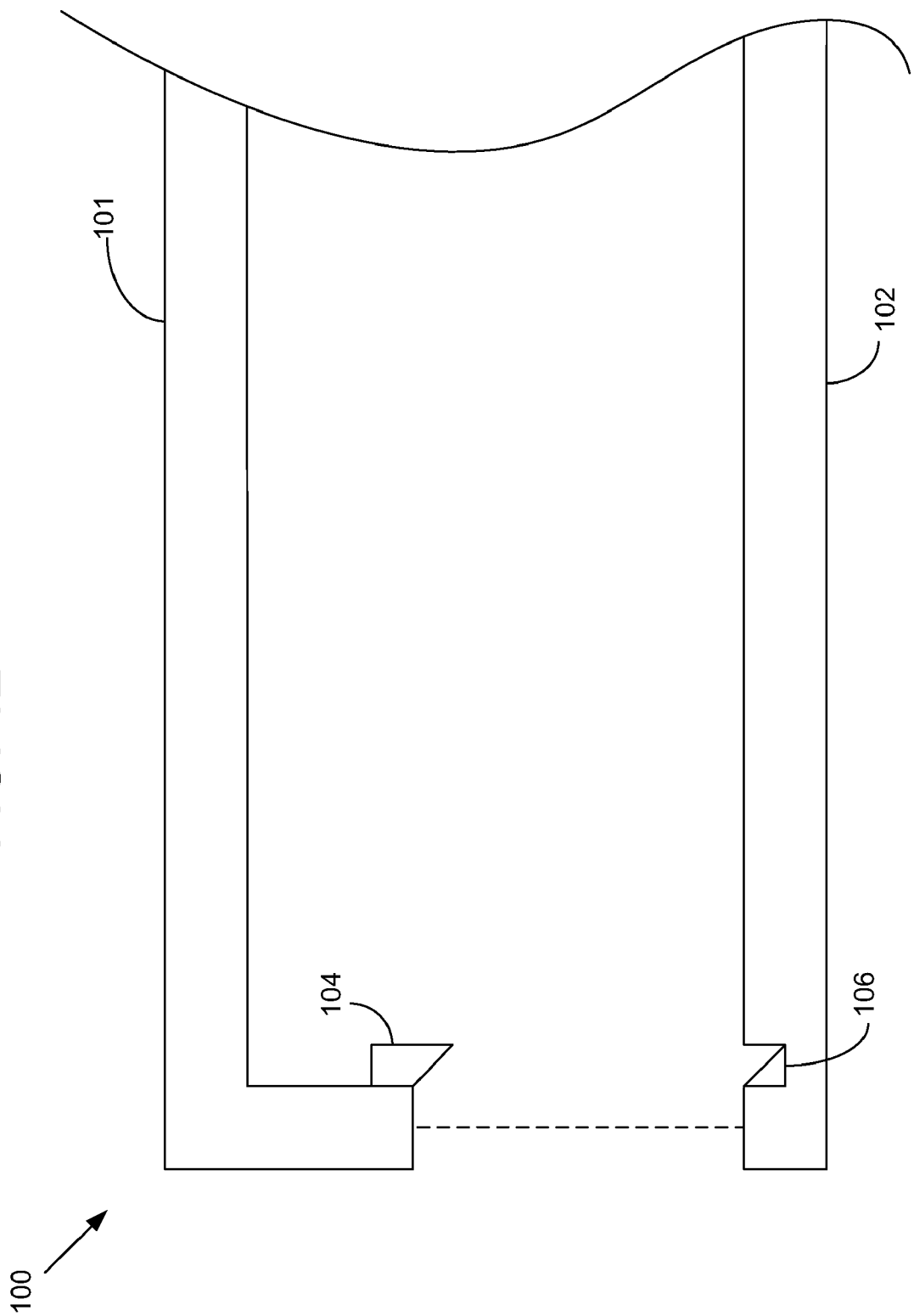
FIG. 12 illustrates a portion of a medical device system in accordance with an embodiment of the present invention.
Figure 13:
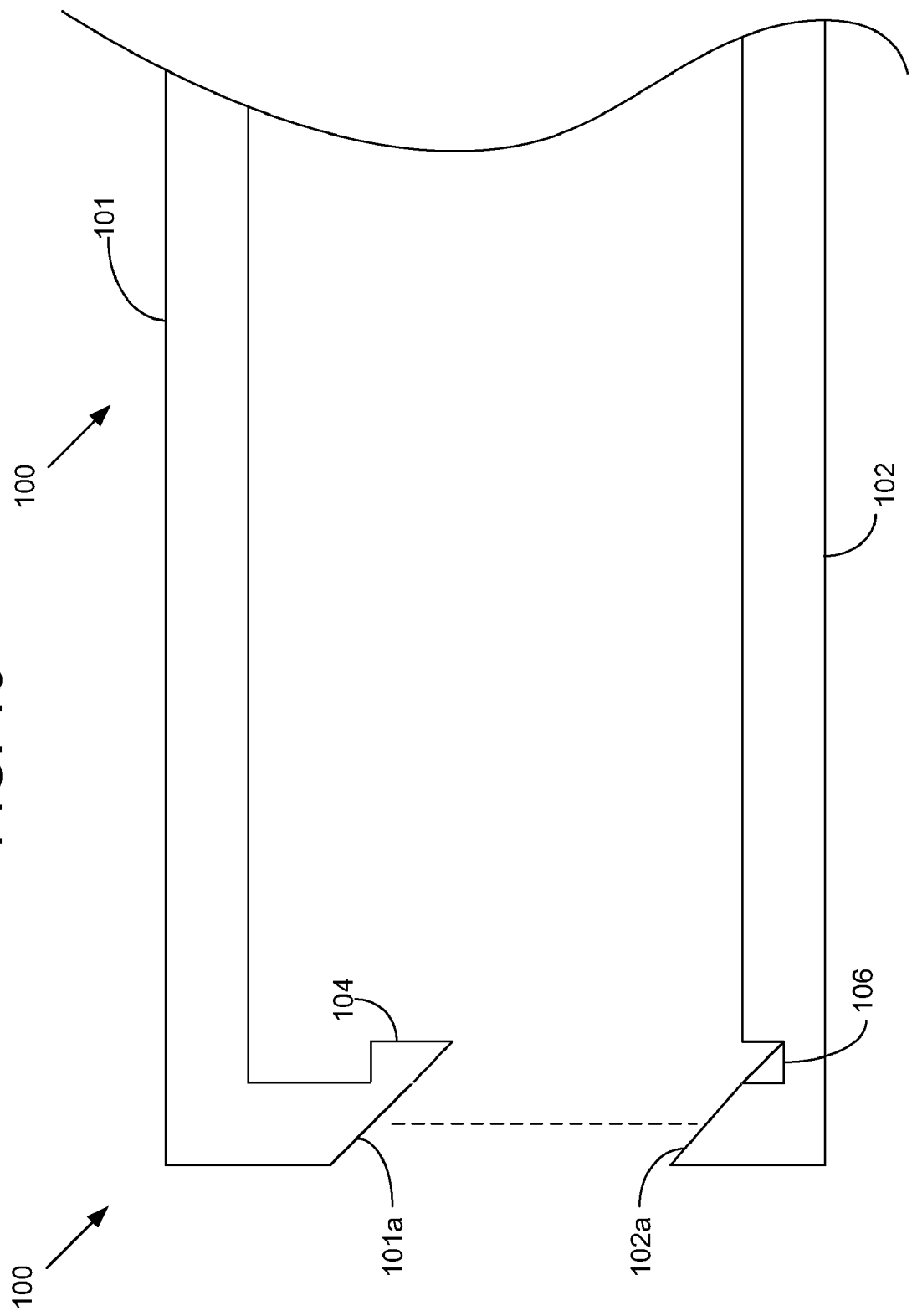
FIG. 13 illustrates a medical device system in accordance with an embodiment of the present invention.
Figure 17:
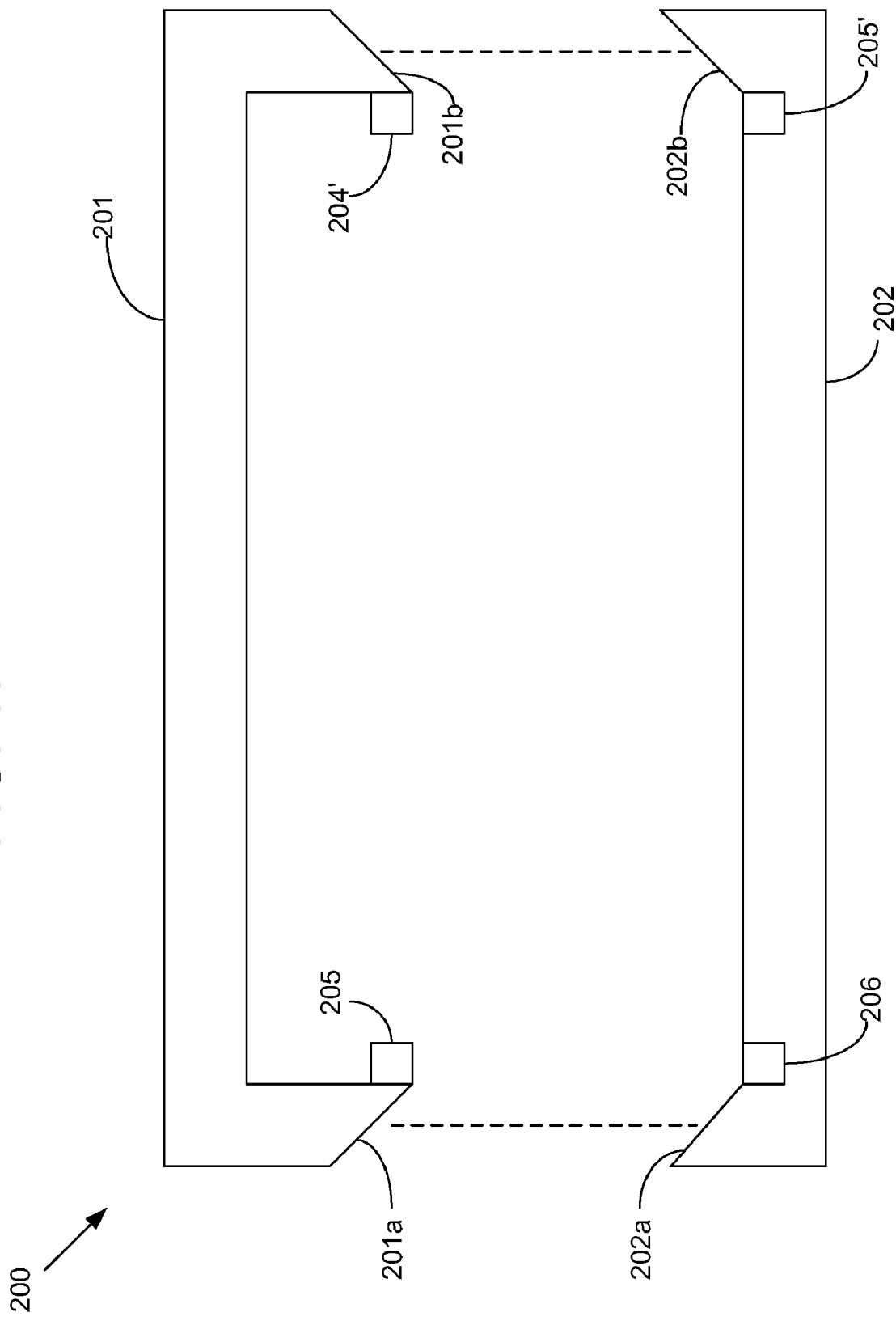
FIG. 17 illustrates a medical device system in accordance with an embodiment of the present invention.

In some embodiments, such as the embodiment exemplified in FIG. 12, one or both of the first interactive element 104 and the second interactive element 106 may have a mating, sloped or otherwise shaped surface for engaging and providing an alignment function when the first part 101 and the second part 102 are brought together for connection. For example, the first interactive element 104 may have a sloped surface adapted to be mated with a corresponding sloped surface of the second interactive element 106 in a manner similar to that described with respect to the first sloped surface 101a (e.g., FIGS. 7-11) and the second sloped surface 102a (e.g., FIGS. 7-11). In further embodiments, such as the embodiment exemplified in FIG. 13, one or both of the first part 101 and the second part 102 may include sloped surfaces 101a, 102a for mating with interactive elements (e.g., first interactive element 104, second interactive element 106) having appropriately shaped surfaces similar to that previously described.

In various embodiments, such as the embodiments exemplified in FIGS. 14A and 14B, one or more of the interactive elements (e.g., first interactive element 104, first interactive element 104', second interactive element 106, second interactive element 106', and/or the like) may be a spring, finger, or other bias member for contacting one or more of the other interactive elements upon the first part 101 and the second part 102 being operatively engaged. In such embodiments, the one or more of the interactive elements may be made of a suitably rigid material, such as, but not limited to, metal, plastic, glass, composite materials, rubber, and/or the like.

For example, as shown in FIG. 14A, the second interactive element 106 may be biased toward a first position, for example an extended position. As the first part 101 and the second part 102 are brought together, the second interactive element 106 may be urged by a portion of the opposing part to a second position, for example a collapsed position (e.g., FIG. 14B). For instance, in FIGS. 14A and 14B, the first interactive element 104 supported by the first part 101 may urge the second interactive element 106 to the second position upon operatively engaging the first part 101 and the second part 102.

In some embodiments, a spring, finger, or bias member may be arranged or otherwise provided between the interactive elements for allowing the interactive elements to interact with each other via the bias member, for example, upon the first part 101 and the second part 102 being operatively engaged. In further embodiments, the bias member may function as a conductor (e.g., an electrically conductive medium, magnetically conductive medium, thermally conductive medium, and/or the like), such as a metal and/or the like, between the interactive elements. For example, in embodiments where the bias remember is an electrically conductive medium, the bias member may be arranged and/or configured for allowing an electrical connection between the interactive elements via the bias member.

Alternatively or in addition, in some embodiments, one or more of the interactive elements may be supported by a spring, finger, or other bias member for contacting the other interactive element upon the first part 101 and the second part 102 being operatively engaged. Thus in such embodiments, the supported interactive element(s) may be biased in a first direction (e.g., FIG. 14A) and/or urgeable or otherwise moveable to a second position (e.g., FIG. 14B) as previously described.

In various embodiments, such as the embodiments exemplified in FIGS. 15A and 15B, more than one interactive element (e.g., first interactive element 104, first interactive element 104', second interactive element 106, second interactive element 106', and/or the like) may be spaced apart from each other on one of the first part 101 and the second part 102. At least one of the more than one interactive element (e.g., second interactive element 106) or a portion thereof may be movable by a portion (e.g., interactive element 104, a finger, pusher, and/or the like) of the other of the first part 101 and the second part 102 upon the first part 101 and the second part 102 being operatively engaged.

Thus, for example, as shown in FIGS. 15A and 15B, upon the first part 101 and the second part 102 being operatively engaged, the second interactive element 106' may be urged by the first interactive element 104 toward the second interactive element 106. Accordingly, the second interactive element 106' may be moved to contact or otherwise placed within range with the second interactive element 106 to allow some or all of the interactive elements (e.g., first interactive element 104, second interactive element 106', and/or second interactive element 106) to interact with each other. Likewise, in other embodiments, the first interactive element 104' (not shown) may be moved to contact or otherwise placed within range with the first interactive element 104 in a similar manner to allow the interactive elements (e.g., first interactive element 104, first interactive element 104', second interactive element 106, and/or the like) to interact with each other.

In some embodiments, for example, the first interactive element 104 and the second interactive element 106 can be arranged on one of the first part 101 and the second part 102 to be spaced apart and movable relative to each other in a manner such as that previously described. In such embodiments, for instance, a portion of the other of the first part 101 and the second part, such as a tab, finger, and/or the like may be arranged to urge the first interactive element 104 and the second interactive element 106 toward each other to allow the interactive elements to interact (e.g., contact) with each other. Thus in such embodiments, most or all of the interactive elements may be provided on one of the housing portions, for example the durable housing portion 30 (FIGS. 1-6C), which may allow for reuse of the interactive elements. In other embodiments, the movable interactive element may be any suitable intermediary member (e.g., second interactive element 106' in FIGS. 15A and 15B) configured to be movable relative to one or more of the interactive elements in a manner described, for example, with respect to FIGS. 15A and 15B.

In other embodiments (see, e.g., FIG. 31 described later), the movable interactive element (or a portion thereof) may instead be a flexible layer, such as a film made of a suitably flexible material including, but not limited to, a Mylar and/or the like, that can be pushed upon by the portion of the opposing part to contact the other interactive element. In further embodiments, the flexible layer may be a conductive layer, such an electrically conductive medium (e.g., metal and/or the like), magnetically conductive medium (e.g., a ferrous conduit), thermally conductive medium, and/or the like.

Thus in various embodiments, as part of a process of assembling a first part 101 and a second part 102 of a medical device system 100, a user may bring the first part 101 and the second part 102 together to operatively engage each other or otherwise be in sufficiently close proximity. Accordingly, a first interactive element 104 and a second interactive element 106 may be interactable with each other to determine, for example, whether the first part 101 and the second part 102 have been properly aligned and/or connected.

In various embodiments, the interactive elements (e.g., first interactive element 104, second interactive element 106, and/or the like) may allow for, but is not limited to, tracking a number of times a component has been connected to and/or disconnected from other components, verifying proper connection and/or alignment of components in a medication delivery system prior to each delivery step, checking, sensing, and/or measuring parameters, such as ambient parameters (e.g., ambient magnetic fields), operating parameters, and/or the like, alerting users to conditions, such as conditions outside operating parameters of the delivery system, and/or the like.

Various embodiments may employ different arrangements of interactive elements on the first part 101 and/or the second part 102. For instance, in embodiments in which one of the first part 101 and the second part 102 is intended to be disposable (e.g., disposed of after one or a prescribed number of uses or period of use), some of the interactive elements may be provided on the disposable part, while other interactive elements may be provided on a durable part (i.e., not intended to be disposed). As a result, after a period of usage, the interactive element(s) on the disposable part that may have attracted and collected stray material can be disposed of with the disposable part.

On the other hand, the interactive element(s) on the durable part can be sufficiently clean and free (or be cleaned) of stray material for further usage. In such embodiments, arranging at least some of the interactive element(s) on the durable portion may provide certain advantages, such as, but not limited to, being more cost-effective, for example, by arranging interactive elements on respective parts based on cost; easier to manufacture and/or install, and/or the like. For example, electronics and circuitry, such as, but not limited to, a sensor (e.g., FIGS. 16-23), a responsive device (e.g., FIGS. 24-29B and 33), and/or other circuitry or electronics, may be arranged on the durable part.

In yet other embodiments, arranging at least some of the interactive element(s) on the disposable portion may provide certain advantages, such as, but not limited to, maintenance, cost, and/or the like. For example, such embodiments may allow for the interactive element(s) that have worn down, been contaminated, or otherwise collected stray material to be disposed of with the disposable part.

FIGS. 16-19 illustrate a medical device system 200 according to various embodiments of the present invention. The medical device system 200 may include features similar to or employed as an embodiment of the medical device system 100 (e.g., FIGS. 7-15B) and/or the other medical device systems discussed throughout the disclosure. Although the medical device system 200 may include features similar or used with the embodiments of FIGS. 7-15B, it should be understood that the medical device system 200 may also include some or all of the same features and operate in a manner similar to that shown and described in the embodiments of FIGS. 1-6C and 20-32B. In addition, some or all of the features shown in FIGS. 1-15B and 20-32B may be combined in various ways and included in the embodiments shown in FIGS. 16-19. Likewise, it should be understood that any of the features of the embodiments of FIGS. 16-19 may be combined or otherwise incorporated into any of the other embodiments of FIGS. 16-19 as well as any other embodiment herein discussed.

In some embodiments, such as the embodiment exemplified in FIG. 16, at least one of a first interactive element 204, which may be similar to first interactive element 104 (e.g., FIGS. 7-15B), and a second interactive element 206, which may be similar to the second interactive element 106 (e.g., FIGS. 7-15B), may be a suitable sensor 205 for sensing the other of the first interactive element 204 and the second interactive element 206 and/or an interactive element, such as a conductive medium (e.g., FIG. 18 discussed later) operatively connected to or otherwise associated with the other of the first interactive element 204 and the second interactive element 206. Accordingly, upon the sensor 205 detecting the presence of the other of the first interactive element 204 and the second interactive element 206, the alignment system 200 may determine whether the first part 201 and second part 202 have been properly connected (i.e., aligned and connected).

In various embodiments, suitable electronics may be connected to the sensor 205 and/or the other of the first interactive element 204 and the second interactive element 206 to provide a controlled power signal to selectively activate or otherwise control the sensor 205 and/or the other of the first interactive element 204 and the second interactive element 206. For example, the sensor 205 may be controlled to activate upon a manual activation of a control button, switch, or other manual operator on one of the connectable components or on a remote-controller device (not shown) connected in wireless communication with the sensor 205 through suitable control electronics. As another example, the sensor 205 may be controlled to activate automatically after a certain action, such as activation of a button, and/or the like or after a certain amount of time. In some embodiments, the sensor 205 may be controlled to activate upon activation or insertion of a particular component or device, such as, but not limited to, a needle inserter to insert a needle or cannula.

Examples of various needle insertion tools are described in, but are not limited to, U.S. patent application Ser. No. 11/645,972, filed Dec. 26, 2006, "Infusion Medium Delivery System, Device And Method With Needle Inserter And Needle Inserter Device And Method"; U.S. patent application Ser. No. 11/646,052, filed Dec. 26, 2006, "Infusion Medium Delivery System, Device And Method With Needle Inserter And Needle Inserter Device And Method"; U.S. patent application Ser. No. 11/645,435, filed Dec. 26, 2006, "Infusion Medium Delivery System, Device And Method With Needle Inserter And Needle Inserter Device And Method"; U.S. patent application Ser. No. 11/646,000, filed Dec. 26, 2006, "Infusion Medium Delivery System, Device And Method With Needle Inserter And Needle Inserter Device And Method," all of which are herein incorporated by reference in their entirety. Thus, in such examples, the sensor 205 may be activated, for example, before or after, the first part 201 and the second part 202 are brought operatively engaged.

In some embodiments, the sensor 205 may be activated upon interacting with the other of the first interactive element 204 and the second interactive element 206. In some embodiments, an activating element, such as an activating magnet and/or the like, may be provided on at least one of the first part 201 and the second part 202. The activating element may activate the sensor 205 upon interacting with each other, for example by contacting each other when the first part 201 and the second part 202 are operatively engaged and properly aligned. In particular embodiments, the activating element may be one of the interactive elements.

The sensor 205 may be any suitable detector configured to detect a detectable feature, such as an interactive element (e.g., first interactive element 204, second interactive element 206, and/or the like) or a presence of an interactive element, such as a magnetic field, electric field, and/or the like provided by the interactive element. In further embodiments, the sensor 205 may be configured to and/or associated with electronics configured to produce an electronically detectable state or signal upon detecting the detectable feature. For example, the sensor 205 may be a sensor pad and/or the like configured to sense, detect, and/or otherwise interact with an interactive element upon the interactive element being in sufficient proximity (e.g., in contact) with the sensor pad. In certain embodiments, the sensor 205 may include a conventional activating switch or a conventional device capable of detecting a particular detectable feature such as an interactive element (e.g., first interactive element 204, second interactive element 206, and/or the like) or a presence of an interactive element, such as a magnetic field, electric field, and/or the like provided by the interactive element.

In some embodiments, the sensor 205 may be configured to sense, detect, or measure a presence of the interactive element. For example, such embodiments may allow for the sensor 205 to sense a presence (e.g., a magnetic field) of the interactive element rather than the element itself. In particular, the sensor 205 may be configured to sense, detect, or measure, but is not limited to, magnetic fields; electric fields; temperature or heat; optical and/or visual features (e.g., barcodes, colors, grayscale, and/or the like); tactile features; audio features; radio frequencies (RF) or other radio signals; ultraviolet light, or other light; force; torque; resistances (e.g., coded resistance pattern); capacitances; inductances; ultrasonic signals, and/or the like; and/or the like provided by, emitted from, produced by, or otherwise present in an interactive element (e.g., the second interactive element 206).

For example, the sensor 205 may be configured to sense a magnetic field emitted by a magnetic second interactive element 206 in a case where the first part 201 and the second part 202 are connected and the sensor 205 and the second interactive element 206 are in proper alignment. If the first part 201 and the second part 202 are operatively engaged and the sensor 205 fails to detect the magnetic field provided by the magnetic second interactive element 206, then this may indicate that the first part 201 and the second part 202 are not properly aligned. On the contrary, if the first part 201 and the second part 202 are operatively engaged and the sensor 205 detects the magnetic field provided by the magnetic second interactive element 206, then this may indicate that the first part 201 and the second part 202 are properly aligned (i.e., the first part 201 and the second part 202 are within a certain tolerance of alignment relative to each other).

In further embodiments, the sensor 205 may be configured to measure a value or presence parameter, magnitudes, changes, gradients, polarities, vectors, field directions, and/or any other measurable parameter suitable for detecting and/or measuring a detectable feature. For example, a sensor 205 may be configured to measure a gauss level of a magnetic field provided by a second interactive element 206.

In various embodiments, the detectable feature (e.g., second interactive element 206) may be selected, configured, and/or arranged to provide a particular detectability (i.e., a characteristic or trait capable of being detected) such that, for example, the interactive element and/or the presence of the interactive element may be sensed by the sensor 205 only when the first part 201 and the second part 202 are properly aligned. For instance, a magnetic second interactive element 206 may be selected to provide a magnetic field having a particular gauss level that may be detectable by the sensor 205 only if sufficiently proximate to the magnetic second interactive element (i.e., the first part 201 and the second part 202 are within a certain tolerance of alignment relative to each other).

Alternatively or in addition, the sensor 205 may be selected, configured, and/or arranged to select a sensitivity of the sensor or otherwise control an amount sensed of the detectable feature by the sensor 205. Thus, for example, the interactive element and/or the presence of the interactive element may be sensed by the sensor 205 only when the first part 201 and the second part 202 are properly aligned; otherwise, the detectable feature would not be sufficiently proximate to be detectable by the sensor 205 having a reduced sensitivity. For instance, a sensor 205 may be configured to sense, for example, a magnetic second interactive element 206 or a field of the magnetic second interactive element 206 only if sufficiently proximate to the magnetic second interactive element 206.

Such embodiments may allow, for example, for a lesser tolerance in connecting the first part 201 and the second part 202. Accordingly, such embodiments may be used in a case where a connection between the first part 201 and the second part 202 need (but not limited to) more precision. In other embodiments, the sensor may have an increased sensitivity or the like. Such embodiments may allow, for example, for a greater tolerance in connecting the first part and second part.

In some embodiments, the sensor 205 or other associated circuitry may be configured such that a detection not meeting a certain range (e.g., below the range or above the range) or threshold may be ignored or otherwise determined to be unacceptable by the sensor 205 (or other associated circuitry). Thus, in such embodiments, a case where the sensor 205 does not detect the interactive element and/or the presence of the interactive element, the sensor 205 (or other circuitry) may provide an indication that the first part 201 and the second part 202 have not been properly engaged (e.g., connected and/or aligned).

In yet further embodiments, the sensor 205 and/or other associated electronics may be configured such that a detection not meeting a certain range or threshold (i.e., determined to be unacceptable) may provide an indication that the detection does not meet the certain range or threshold. For example, such an indication may indicate that the first part 201 and the second part 202 are operatively engaged, but not properly aligned. In further embodiments, the indicator may indicate, for example, that the parts are laterally misaligned in one or more directions, the parts are have not been brought sufficiently together, and/or the parts have not been connected properly (e.g., connected backwards).

In some embodiments, other interactive elements or structures may be provided to regulate the sensing and/or measuring ability of the sensor 205 and/or the detectability and/or measurability of the detectable feature. For example, a heat-emitting second interactive element 206 may be at least partially surrounded by a low thermally conductive material, such as plastic, rubber, wood, and/or the like. This may allow a heat-sensing sensor 205 to sense the heat-emitting second interactive element 206 and/or a suitable presence thereof only when the first part 201 and the second part 202 are properly aligned, thus substantially preventing a false detection of heat that may be emitted, for example, laterally from the heat-emitting second interactive element 206.

In various embodiments, one of the interactive elements may have a capacitance that is measurable. Another interactive element (or other component) may be configured to affect the capacitance of the one of the interactive elements, for example, by being brought in proximity or contact with the one of the interactive elements. The affected capacitance of the one of the interactive elements may be measured or otherwise, for example, by a sensor (e.g., sensor 205) detected to indicate a change in state (e.g., that two components have been connected).

In various embodiments, one of the interactive elements may have an inductance that is measurable. Another interactive element (or other component) may be configured to affect the inductance of the one of the interactive elements, for example, by being brought in proximity or contact with the one of the interactive elements. The affected inductance of the one of the interactive elements may be measured or otherwise, for example, by a sensor (e.g., sensor 205) detected to indicate a change in state (e.g., that two components have been connected).

In some embodiments having multiple pairs of interactive elements, the first interactive element 204 and the first interactive element 204' may be sensor 205 and sensor 205' respectively that may be configured to detect, for example, the second interactive element 206 and the second interactive element 206' respectively. Thus, the system 200 may be deemed to have been properly connected in case where the sensor 205 detects the second interactive element 206 and the sensor 205' detects the second interactive element 206'. In other embodiments, the second interactive element 206 and the second interactive element 206' may be sensor 205 and sensor 205' respectively that may be configured to detect, for example, the first interactive element 204 and the first interactive element 204' respectively. In some embodiments, such as the embodiment exemplified in FIG. 17, at least one of the first interactive element 204 and the first interactive element 204' may be a sensor 205 configured to detect one of the second interactive element 206 and the second interactive element 206' and the other of the second interactive element 206 and the second interactive element 206' may be a sensor 205' configured to detect the other of the first interactive element 204 and the first interactive element 204'.

In some embodiments, both the first interactive element 204 and the second interactive element 206 may each be sensors 205. In such embodiments, one or more of the sensors 205 may be configured to detect the other sensor 205 and/or other interactive element(s). For example, the first part 201 and the second part 202 may be deemed to have been operatively engaged properly in a case where (but not limited to) one of the sensors 205 detects the other sensor 205, the sensors 205 both detect each other, one or more of the sensors 205 detects an other interactive element, and/or the like.

In further embodiments, further sensors may be provided for detecting other sensors (and/or interactive elements). In such embodiments, the first part 201 and the second part 202 may be deemed to have been operatively engaged properly, but is not limited to, upon one or more or a predetermined amount of the sensors 205 detecting a particular or any of the other sensors 205, the sensors 205 detecting each other, one or more of the sensors 205 detecting an other interactive element, and/or the like.

In various embodiments, one or more additional sensing structures, such as those described above, may be provided to align the first part 201 and the second part 202, for example, to increase reliability of alignment and/or decrease time for sensing proper alignment.

Thus in various embodiments, as part of a process of assembling a first part 201 and a second part 202 of a medical device system 200, a user may bring the first part 201 and the second part 202 together to operatively engage each other or otherwise be in sufficiently close proximity. Accordingly, a sensor 205 may detect a detectable feature to determine, for example, whether the first part 201 and the second part 202 have been operatively engaged properly (e.g., aligned and/or connected).

Figure 18:
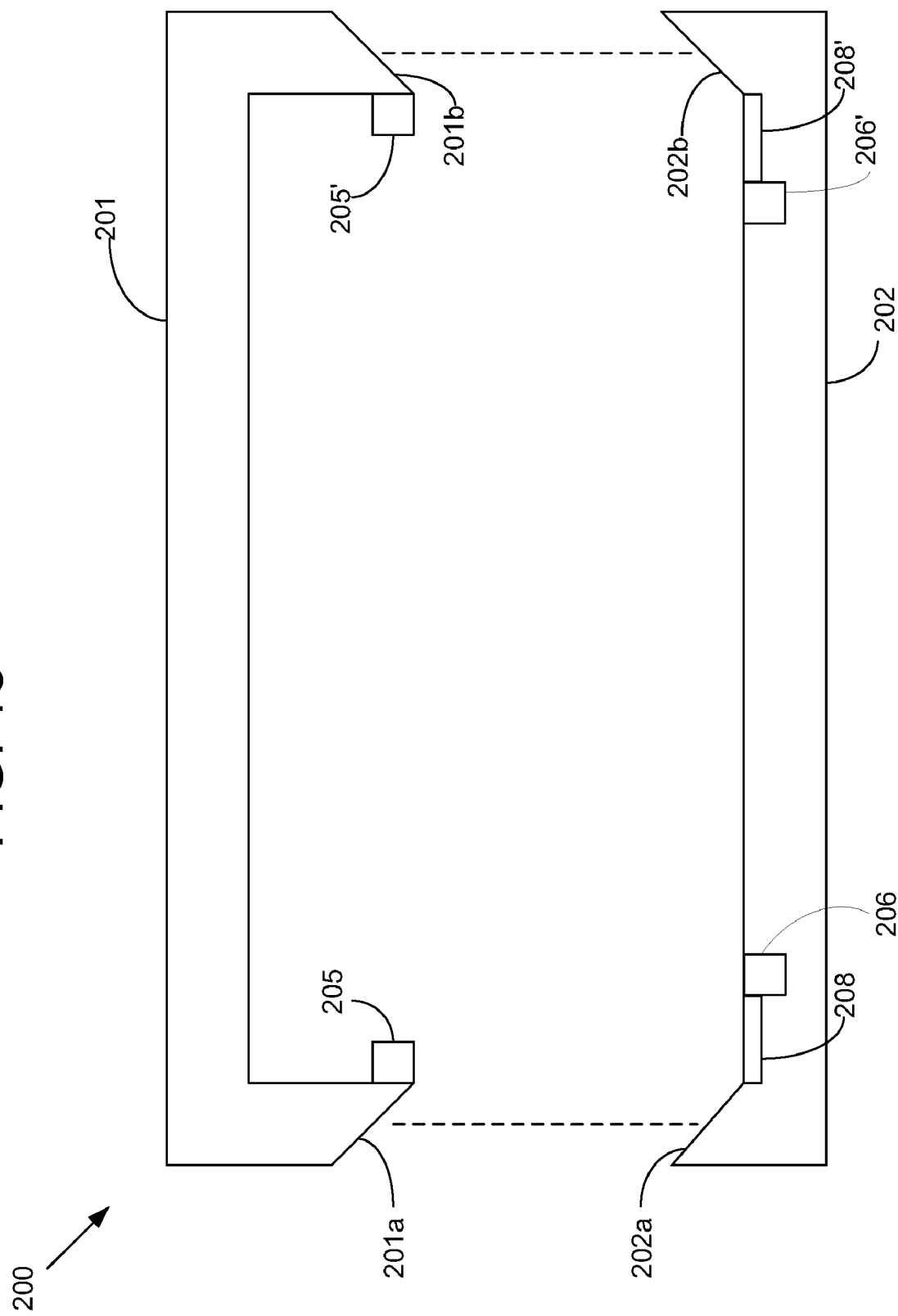
FIG. 18 illustrates a medical device system in accordance with an embodiment of the present invention.

In some embodiments, such as the embodiment exemplified in FIG. 18, a conductive medium 208 may be at a position adjacent one of the interactive element(s) (e.g., the second interactive element 206 in FIG. 18) or otherwise in communication with the interactive element to allow the conductive medium 208 to function as a conductor for the interactive element. In such embodiments, the interactive element may interact with the conductive medium 208 to allow the conductive medium 208 to be have similar characteristics or properties, though not necessarily exactly the same characteristics or properties. For example, a magnetic second interactive element 206 may provide a magnetic charge to a magnetic conductive medium 208. The conductive medium 208 may be made of a material, such as, but not limited to, an electrically conductive material (e.g., metal, graphite, salt solutions, plasma, and/or the like), a magnetically attractive material (e.g., metal), a sufficiently high thermally conductive material (e.g., metal, or any other material with a thermal conductivity, for example (but not limited to), above 1), and/or the like.

In further embodiments, the conductive medium 208 may be arranged on its respective part to allow the interactive element to be interactable with the other interactive element (e.g., the sensor 205 in FIG. 18) on the opposing part via the conductive medium 208 in any of the manners described throughout the disclosure. For example, in particular embodiments, the sensor 205 may detect or otherwise interact with the conductive medium 208 in a case where the first part 201 and the second part 202 are operatively engaged properly. Accordingly, the second interactive element 206 or presence thereof may be detectable by the sensor 205 via the conductive medium 208. Thus, some embodiments may allow for the sensor 205 to detect the conductive medium 208 in addition to or alternative to the interactive element (e.g., the second interactive element 206). For example, a magnetic second interactive element may magnetize a magnetically attractive conductive medium 208, which may then be detected by the sensor 205.

Figure 19:
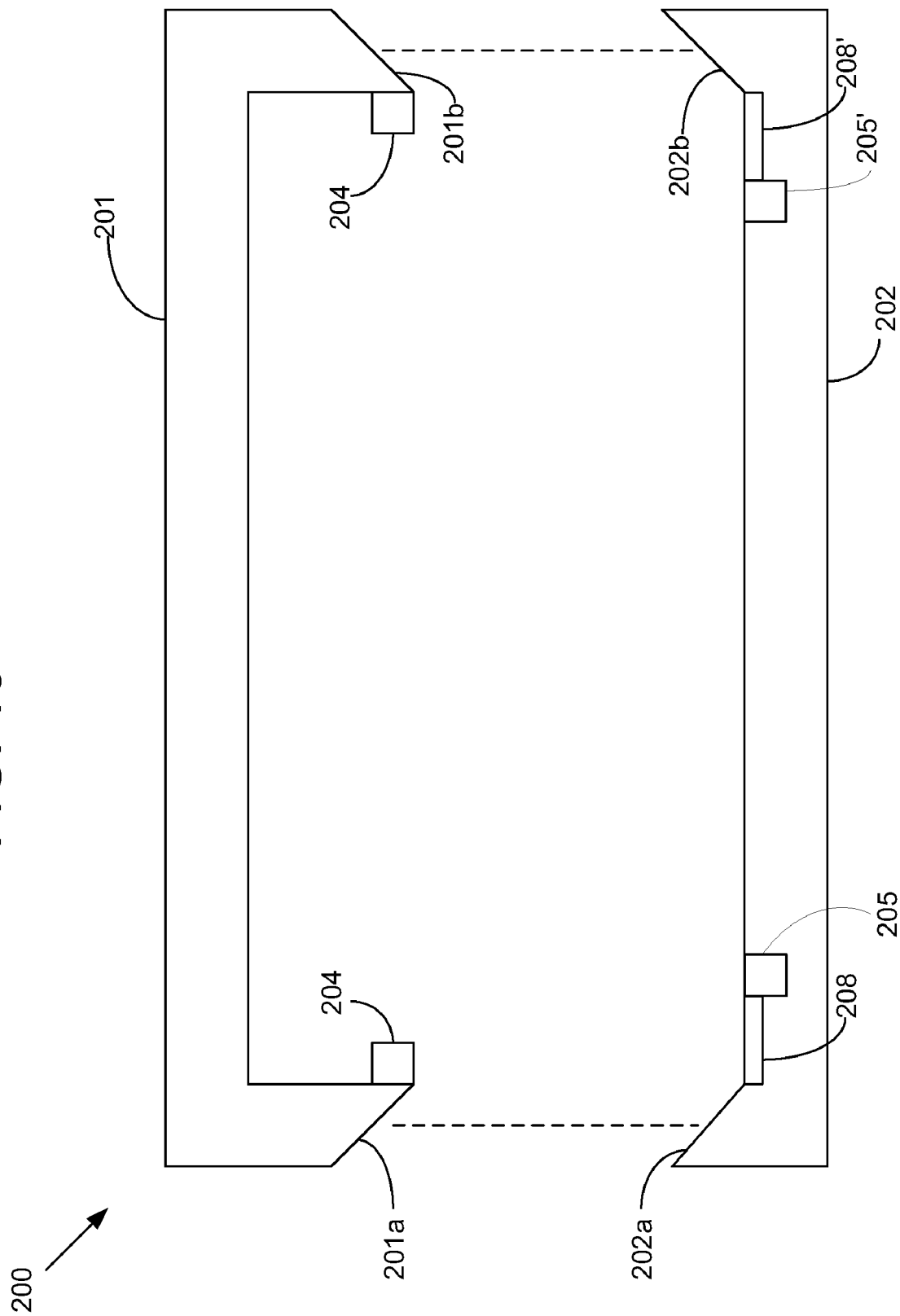
FIG. 19 illustrates a medical device system in accordance with an embodiment of the present invention.

In some embodiments, such as the embodiment exemplified in FIG. 19, the conductive medium 208 may be arranged at a position adjacent the other interactive element (e.g., the sensor 205 in FIG. 19) or otherwise in communication with the other interactive element to allow the conductive medium 208 to function as a conductor for the other interactive element. In further embodiments, the conductive medium 208 may be arranged on its respective part to allow the other interactive element to be interactable with the interactive element (e.g., the first interactive element 204 in FIG. 19) on the opposing part via the conductive medium 208 in any of the manners described throughout the disclosure.

For example, in particular embodiments, the first interactive element 204 may interact with the conductive medium 208 in a case where the first part 201 and the second part 202 are operatively engaged properly. Accordingly, the first interactive element 204 may be detectable by the sensor 205 via the conductive medium 208. Thus, some embodiments may allow for the sensor 205 to detect the interactive element (e.g., the second interactive element 206) through the conductive medium 208 in addition to or alternative directly detecting the interactive element. For example, an electrical connection between the first interactive element 204 and the conductive medium 208 (e.g., electrically conductive medium) may be established by contacting the conductive medium 208, which may then be detected by the sensor 205.

Thus in various embodiments, as part of a process of assembling a first part 201 and a second part 202 of a medical device system 200, a user may bring the first part 201 and the second part 202 together to operatively engage each other or otherwise be in sufficiently close proximity. Accordingly, an interactive element (e.g., first interactive element 204, second interactive element 206, and/or the like), a sensor 205, and/or an conductive material 208 may interactable with each other to determine, for example, whether the first part 201 and the second part 202 have been operatively engaged properly aligned (e.g., connected and/or aligned).

In various embodiments, the interactive element(s) (e.g., first interactive element 204, second interactive element 206, and/or the like), the sensor(s) 205, and/or the conductive medium 208 need not be used or otherwise limited to two housing portions. FIGS. 20-23 illustrate a medical device system 300 according to various embodiments of the present invention. The medical device system 300 may include features similar or employed as an embodiment of the medical device system 100 (e.g., FIGS. 7-15B), the medical device system 200 (e.g., FIGS. 16-19) and/or other delivery devices discussed throughout the disclosure. Although the medical device system 300 may include features similar or used with the embodiments of FIGS. 7-19, it should be understood that the medical device system 300 may also include some or all of the same features and operate in a manner similar to that shown and described in the embodiments of FIGS. 1-6C and 24-32B. In addition, some or all of the features shown in FIGS. 1-19 and 24-32B may be combined in various ways and included in the embodiments shown in FIGS. 20-23. Likewise, it should be understood that any of the features of the embodiments of FIGS. 20-23 may be combined or otherwise incorporated into any of the other embodiments of FIGS. 20-23 as well as any other embodiment herein discussed.

As previously described, a first part 301, which may be similar to the first part 101 (and 201) (e.g., FIGS. 7-19), and a second part 302, which may be similar to the second part 102 (and 202) (e.g., FIGS. 7-19), may be two housing portions, such as, but not limited to, a durable housing portion 30 (e.g., FIGS. 1-6C) and a disposable housing portion 20 (e.g., FIGS. 1-6C), as previously described. A third part 303 may be provided that may be, but is not limited to, a base portion 21 (e.g., FIGS. 1-6C). In some embodiments, the conductive medium 308 or further conductive mediums (e.g., electrically conductive medium, magnetically attractive material, such as a yoke, ferrous conduit, thermally conductive material, and/or the like) may be provided on at least one of the parts. This may allow for a connection or interaction between the interactive element(s) (e.g., first interactive element 304, second interactive element 306, and/or the like) and/or the sensor(s) 305.

For example, in the embodiment exemplified in FIG. 20, a conductive medium 308 (e.g., electrically conductive medium, yoke, ferrous conduit, and/or the like) may be provided in a third part 303. A first interactive element 304 may supported by a first part 301 in a position to interact with the conductive medium 308 of the third part 303 upon the first part 301 being operatively engaged with the third part 303. A sensor 305 may be supported by a second part 302 in a position to interact with the conductive medium 308 of the third part 303 upon the second part 302 being operatively engaged with the third part 303.

Thus in some embodiments, in a case where a first part 301 is operatively engaged with a third part 303 and a second part 302 is operatively engaged with the third part 303, a first interactive element 304 may be detectable by a sensor 305 via a conductive medium 308. In various embodiments, the arrangement of each of the conductive medium 308, the first interactive element 304 (or other interactive elements, such as second interactive element 306, and/or the like), and the sensor 305 need not be limited to the third part 303, the first part 301, and the second part 302, respectively, but may be arranged on any of the components as well as any other components as needed.

Another example as exemplified in FIG. 21, a conductive medium 308' (e.g., electrically conductive medium, yoke, ferrous conduit, and/or the like) may be provided in a third part 303 as well as a first part 301. A first interactive element 304 may supported by a second part 302 in a position to interact with the conductive medium 308' of the third part 303 upon the second part 302 being operatively engaged with the third part 303. A sensor 305 may be supported by the second part 302 in a position to interact with a conductive medium 308 of the first part 301 in a case where each of the first part 301 and the second part 302 is operatively engaged with the third part 303.

Thus in some embodiments, in a case where a first part 301 is operatively engaged with a third part 303 and a second part 302 is operatively engaged with the third part 303, a first interactive element 304 may be detectable by a sensor 305 via a conductive medium 308 and a conductive medium 308'. In various embodiments, the arrangement of each of the conductive medium 308 and 308', the first interactive element 304 (or other interactive elements (e.g., second interactive element 306, and/or the like), and the sensor 305 need not be limited to the exemplified arrangements, but may be arranged on any of the components as well as any other components as needed.

Figure 22:
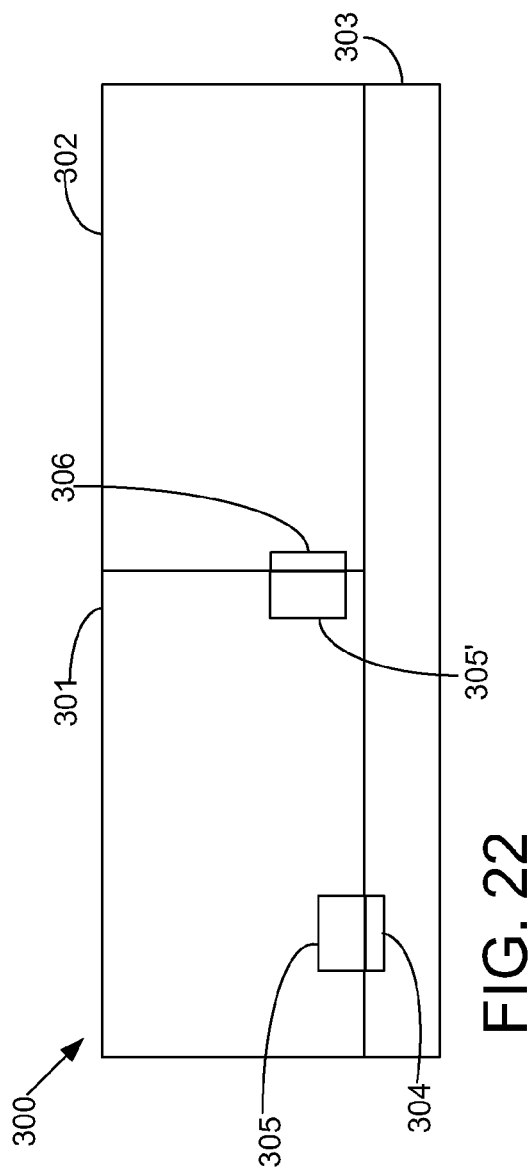
FIG. 22 illustrates a medical device system in accordance with an embodiment of the present invention.

In some embodiments, such as the embodiment exemplified in FIG. 22, more than one sensor, such as a sensor 305 and a sensor 305', may be arranged on one of the parts (e.g., first part 301, and/or the like). Each of the sensor 305 and the sensor 305' may be configured to sense a respective interactive element (e.g., first interactive element 304, second interactive element 306, and/or the like) located on each of the remaining parts (e.g., second part 302, third part 303, and/or the like). Thus in some embodiments, in a case where each of a first part 301 and a second part 302 is operatively engaged with a third part 303, a first interactive element 304 of the third part 303 may be detectable by a sensor 305 (i.e., a first sensor). Similarly, a second interactive element 306 of the second part 302 may be detectable by a sensor 305' (i.e., a second sensor).

Figure 23:
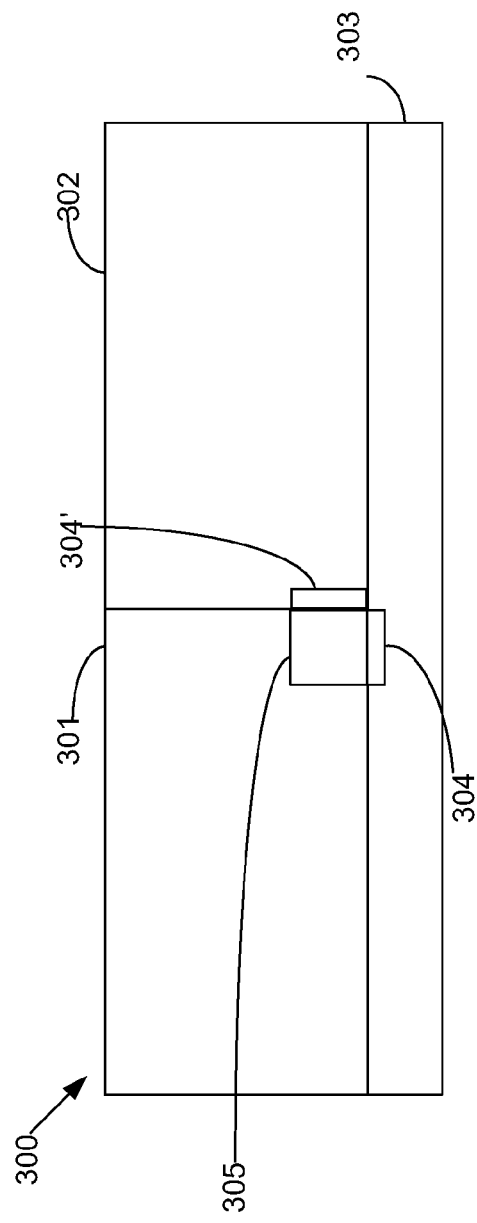
FIG. 23 illustrates a medical device system in accordance with an embodiment of the present invention.

In other embodiments, such as the embodiment exemplified in FIG. 23, a sensor 305 may be arranged on one of the parts (e.g., the second part 302, and/or the like) and configured to sense interactive elements (e.g., first interactive element 304, first interactive element 304', second interactive element 306, second interactive element 306', and/or the like), and/or the like arranged on each of the remaining parts (e.g., first part 301, third part 303, and/or the like). Thus in some embodiments, in a case where each of a first part 301 and a second part 302 is operatively engaged with a third part 303, a first interactive element 304 of the third part 303 and a first interactive element 304' of the second part 302 may be detectable by the sensor 305.

With reference to FIGS. 20-23, in various embodiments, arrangement of each of the interactive element(s) (e.g., first interactive element 304 (and/or 304'), second interactive element 306 (and/or 306'), and/or the like), sensor(s) 305 (and/or 305'), and/or conductive medium(s) 308 (and/or 308') need not be limited to the exemplified arrangements. The various interactive element(s), sensor(s), and/or conductive medium(s) may be arranged as needed in any suitable configuration amongst some or all of the components (e.g., first part 301, second part 302, third part 303) as well as any other components (e.g., further parts, such as an needle-inserting device as discussed further below, electronics housing, and/or the like). As a non-limiting example, in FIG. 22, the sensor 305 and the sensor 305' may be arranged on the second part 302, and/or the third part 303, or further part. As another non-limiting example, in FIG. 21, the first interactive element 304 and the sensor 305 may be arranged on the first part 301 and the conductive medium 308 may be arranged on the second part 302 (or any other part) to allow the first interactive element 304 to interact with the sensor 305 through the conductive medium 308 and the conductive medium 308'.

With reference to FIGS. 20-23, in some embodiments, each of the interactive element(s) (e.g., first interactive element 304 (and/or 304'), second interactive element 306 (and/or 306'), and/or the like), sensor(s) 305 (and/or 305'), and/or conductive medium(s) 308 (and/or 308') may be configured and/or arranged on their respective parts such that the components can interact with each other only if the first part 301, the second part 302, and/or the third part 303 (and/or any further part) are operatively engaged properly. For example, in FIG. 21, if while the parts are operatively engaged, the first part 301 is not moved close enough to the second part 302, the conductive medium 308 of the first part 301 may not provide a connection between the first interactive element 304, the conductive medium 308' of the third part 303, and the sensor 305. Thus, in such an example, the first part 301, the second part 302, and the third part 303 have not been operatively engaged properly.

Thus various embodiments may allow for verification between three (or two or more than three) distinct and separate components, verification of correct positioning between three distinct and separate components, verification that three distinct and separate components have been connected in the correct order, a safety mechanism to provide notification of separation (intentional or accidental) of any individual component in a multi-component system, and/or the like.

Although the medical device system 300 may be similar or used with the embodiments of FIGS. 7-19, it should be understood that the medical device system 200 may also include some or all of the same components and operate in a manner similar to that shown and described in the embodiments relating to the medical device system 300. In addition, some or all of the features shown in FIGS. 20-23 may be combined in various ways and included in the embodiment shown in FIGS. 7-19. For instance, although the description relating to FIGS. 20-23 applied to embodiments having three (or more) housing portions, the features relating to the embodiments of FIGS. 20-23 may be used in addition with or in place of those embodiments having two housing portion discussed, for example, with respect to FIGS. 7-19.

FIGS. 24-29B and 33 illustrate a medical device system 400 according to various embodiments of the present invention. The medical device system 400 may include features similar or employed as an embodiment of the medical device system 100 (e.g., FIGS. 7-23), the medical device system 200 (e.g., FIGS. 16-19), the medical device system 300 (e.g., FIGS. 20-23), and/or other medical device system discussed throughout the disclosure. Although the medical device system 400 may include features similar or used with the embodiments of FIGS. 7-23, it should be understood that the medical device system 400 may also include some or all of the same features and operate in a manner similar to that shown and described in the embodiments of FIGS. 1-6C and 30A-32B. In addition, some or all of the features shown in FIGS. 1-23 and 30A-32B may be combined in various ways and included in the embodiments shown in FIGS. 24-29B and 33. Likewise, it should be understood that any of the features of the embodiments of FIGS. 24-29B and 33 may be combined or otherwise incorporated into any of the other embodiments of FIGS. 24-29B and 33 as well as any other embodiment herein discussed.

The medical device system 400 may include a responsive device 410 configured to provide an electronically detectable state or signal in response to an interaction (or lack thereof) between two or more interactive elements. As previously discussed, an interaction between two or more interactive elements may occur in a case where the first part 401 and the second part 402 are operatively engaged properly or otherwise brought into a pre-defined, sufficiently aligned position and/or in a pre-defined, sufficiently close proximity. The pre-defined aligned position and/or proximity, for example, may correspond to a properly aligned and mutually proximate position for connection of the first part 401 and the second part 402 for operation. Thus, in some embodiments, the responsive device 410 may be configured to provide a signal in a case where the first part 401 and the second part 402 are operatively engaged (or otherwise in sufficient proximity) and properly aligned. The signal may indicate, for example, the two or more interactive elements have interacted, and thus the first part 401 and the second part 402 have been operatively engaged properly. In some embodiments, the responsive device 410 may be configured to change between a relatively non-detectable state to a detectable state (e.g., electrically detectable state) in response to an interaction between two or more interactive elements.

In some embodiments, the responsive device 410 may be configured to detect the interaction between the two or more interactive elements. In further embodiments, the responsive device 410 may be configured to produce an electronically detectable state or signal in response to the responsive device 410 detecting an interaction between the two or more interactive elements. In other embodiments, a sensor, such as the sensor 205 (or 305) (e.g., FIGS. 16-23) or other electronics may be configured to detect the interaction between the two or more interactive elements or to detect a detectable feature as previously described. In further embodiments, the responsive device 410 may be configured to produce an electronically detectable state or signal in response to the sensor detecting an interaction between the two or more interactive elements.

Figure 24:
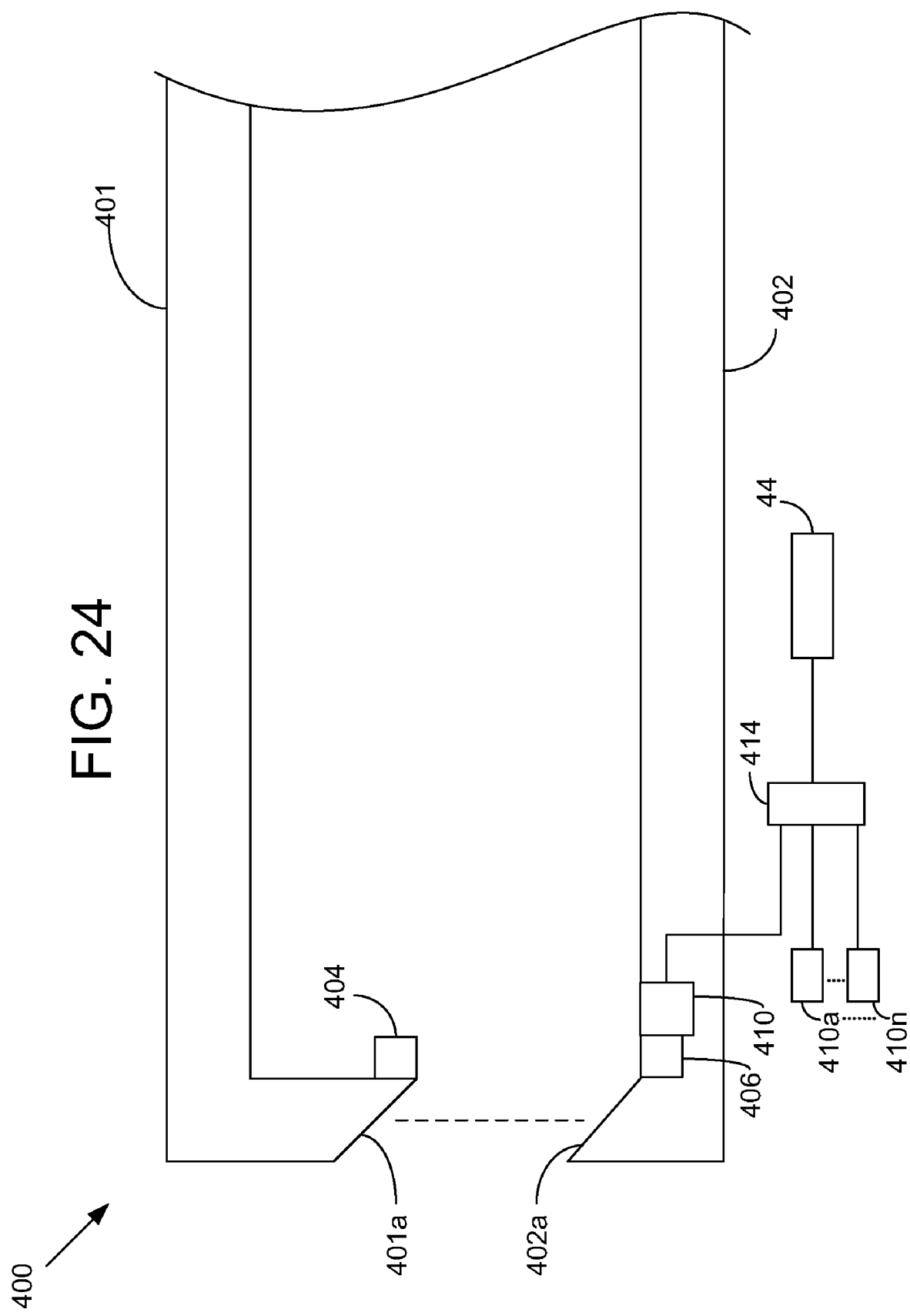
FIG. 24 illustrates a portion of a medical device system in accordance with an embodiment of the present invention.

In some embodiments, such as the embodiment shown in FIG. 24, the responsive device 410, may be configured to provide an electronically detectable state or signal in response to an interaction between two interactive elements, such as a first interactive element 404, which may be similar to the first interactive element 104 (204, and/or 304) (e.g., FIGS. 7-23), and a second interactive element 406, which may be similar to the second interactive element 106 (206, and/or 306) (e.g., FIGS. 7-23). For example, the responsive device 410 may be configured to detect an electrical connection (or lack thereof) between the first interactive element 404, which may be an electrically conductive material, on the first part 401 and a second interactive element, such as an electrical contact, on the second part 402.

Figure 25:
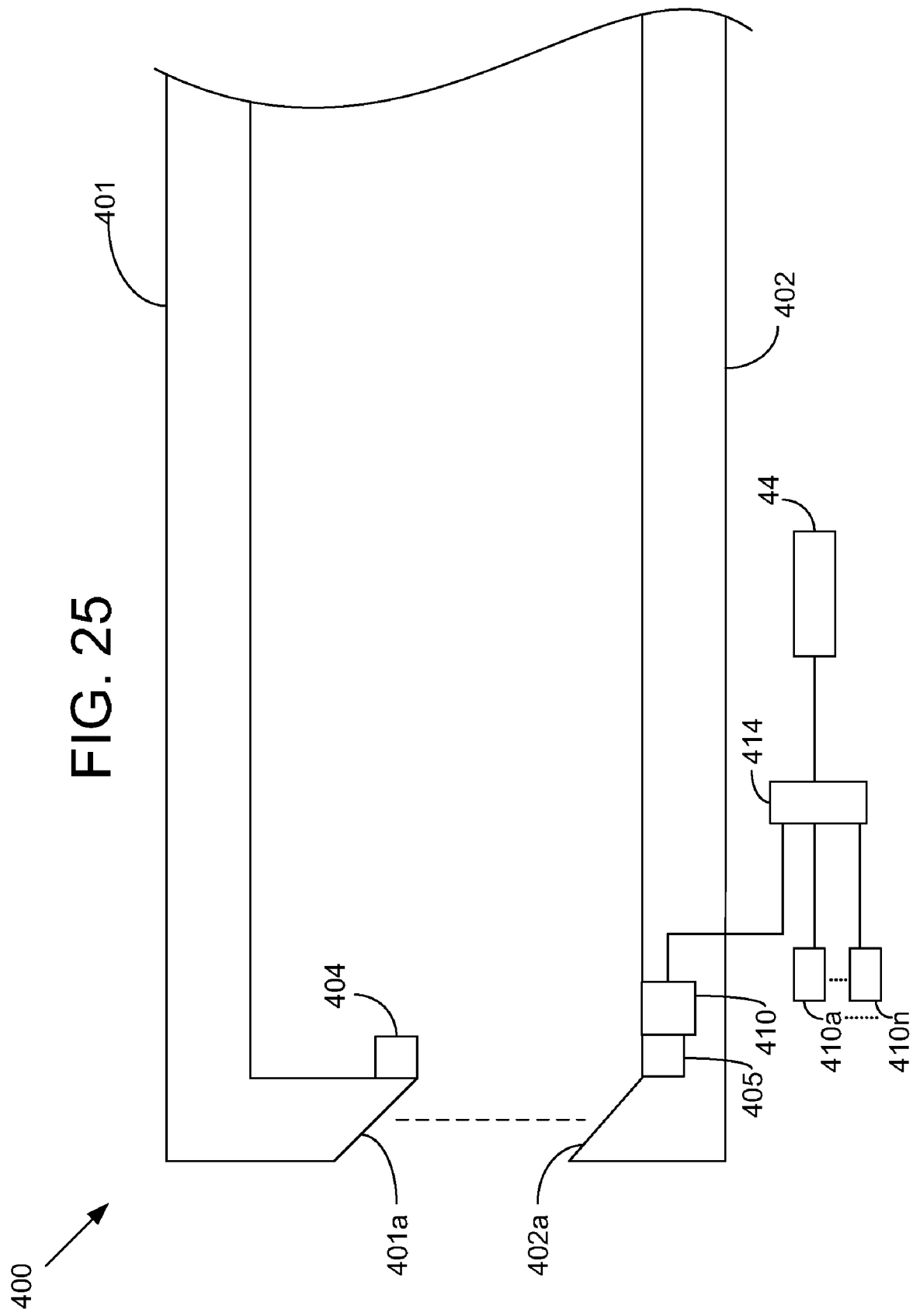
FIG. 25 illustrates a medical device system in accordance with an embodiment of the present invention.

In some embodiments, such as the embodiment shown in FIG. 25, the responsive device 410, may be configured to provide an electronically detectable state or signal in response to an interaction (or lack thereof) between an interactive element or detectable feature (e.g., first interactive element 404) and a sensor 405, for example as described in FIGS. 16-23.

In some embodiments, such as the embodiment shown in FIG. 26, the responsive device 410, may be configured to provide an electronically detectable state or signal in response to an interaction between the responsive device 410 and an interactive element 412, which may be similar to the first interactive element 404 (e.g., FIG. 23) and/or the second interactive element 406 (e.g., FIG. 23). In further embodiments, the responsive device 410 may be an activating switch or the like configured and/or arranged to be activated upon interacting with the interactive element 412. For example, the responsive device 410 may be supported by one or both of the first part 401 and the second part 402 in a position to be activated by the interactive element 412, when the first part 401 and the second part 402 are brought into a pre-defined, sufficiently aligned position and/or in a pre-defined, sufficiently close proximity. The predefined aligned position and/or proximity, for example, may correspond to a properly aligned and mutually proximate position for connection of the first part 401 and the second part 402 for operation.

The interactive element 412 may activate the responsive device 410, for example, by contacting the responsive device 410 and/or a part associated with the responsive device 410, such as an electrically conductive material 408 adjacent the responsive device 410 (e.g., FIG. 28). Accordingly, in such embodiments, in a case where the first part 401 and the second part 402 are brought together and the responsive device 410 is activated by the interactive element 412, the responsive device 410 may provide a signal and/or the like indicating that the first part 401 and the second part 402 have been operatively engaged properly. In other embodiments, a similar responsive device 410 may be provided on the first part 401 and an associated interactive element 412 for activating the responsive device 410 may be provided on the second part 402, either in addition to or as an alternative to the arrangement shown in FIG. 26.

In some embodiments, such as the embodiment exemplified in FIG. 27, multiple responsive devices 410 and 410' and interactive elements 412 and 412' may be provided on the first part 401 and the second part 402 respectively. The interactive element 412', for example, may be similar to or one or more of the first interactive element 104 (204, or 304), the first interactive element 104' (204', or 304'), the second interactive element 106 (206, or 306), the second interactive element 106' (206', or 306'), and/or the like previously described with respect to FIGS. 7-23. Returning to FIG. 27, in other embodiments, multiple responsive devices 410 may be provided with at least one responsive device 410 on each of the first part 401 and the second part 402 for interacting with a respective interactive element 412 on the opposing part. The embodiments described need not be limited to multiple responsive devices 410 and 410' and interactive elements 412 and 412'. Various embodiments may include multiple first interactive elements 404, 404' and second interactive elements 406, 406', as described, for example, with respect to FIG. 24 in addition to or in alternative to the interactive elements 412 and 412' of FIG. 27. Some embodiments may include multiple first interactive elements 404, 404' and sensors 405, 405', as described, for example, with respect to FIG. 25 in addition to or in alternative to the interactive elements 412 and 412' of FIG. 27.

In some embodiments, such as the embodiment exemplified in FIG. 28, an interactive element 412 on the first part 401 (and/or the second part 402) may be arranged to function with a conductive medium 408 on the second part 402 (and/or the first part 401), for example, as previously described with respect to FIGS. 9 and 18-23. With reference to FIG. 28, a responsive device 410 may be located at a position adjacent the conductive medium 408 or otherwise in communication with the conductive medium 408 to allow the conductive medium 408 to function as a conductor for the responsive device 410. The responsive device 410 may be remote from the location of the interactive element 412 on the first part 401. In such embodiments, the interactive element 412 may interact with the conductive medium 408 and thus, interact with the responsive device 410 through the conductive medium 408, for example, to activate the responsive device 410. For example, this may occur in a case where the first part 401 and the second part 402 are brought together for operative engagement and the conductive medium 408 and the interactive element 412 contact each other or otherwise interact with each other.

In some embodiments, a conductive medium 408 may be arranged adjacent to or otherwise in communication with the interactive element 412 to allow the conductive medium 408 to function as a conductor for the interactive element 412, for example, as previously described with respect to FIGS. 9 and 18-23. Returning to FIG. 28, in such embodiments, the interactive element 412 may interact with the conductive medium 408, which may be then interacted with the responsive device 410, for example upon the first part 401 and the second part 402 being operatively engaged. For example, in a case where the interactive element 412 is an electrical contact and the conductive medium 408 is an electrically conductive medium (e.g., copper, aluminum, graphite, and/or the like), the interactive element 412 may energize the conductive medium 408. Thus, an electrical connection may be formed between the interactive element 412 and the responsive device 410 via the conductive medium 408, for example, to activate the responsive device 410 in a case where the first part 401 and the second part 402 are operatively engaged properly.

With reference to FIGS. 24-28, the responsive device 410 may be connected in electrical communication with control electronics 414. The control electronics 414 may be incorporated within the control electronics for controlling a drive device 44 (e.g., FIG. 4) such as, but not limited to, the control electronics 52 (e.g., FIG. 4) for controlling the drive device 44. Alternatively, the control electronics 414 may be separate from and in addition to the control electronics 52, but connected in electrical communication with the control electronics 52 and/or the drive device 44 to provide a drive control signal to the drive device 44. More specifically, the control electronics 414 may be configured to inhibit operation of the drive device 44, unless the responsive device 410 provides a signal or a change in state to the control electronics 414. For instance, as previously discussed, the responsive device 410 may provide such a signal or a change in state upon being activated by the interactive element 412, for example, in a case where the first part 401 and the second part 402 are in proper alignment and sufficiently close in proximity to connect for operation. In other words, the drive device 44 may be inoperable unless the first part 401 and the second part 402 are operatively engaged properly (i.e., aligned and/or connected properly).

In other embodiments, the sensor 205 (305, 405) (e.g., FIGS. 16-28) or electronics associated with the sensor 205 may be connected in electrical communication with control electronics 414 in addition to or in place of the responsive device 410. The control electronics 414 may be configured to inhibit operation of the drive device 44, unless the sensor 205 or electronics associated with the sensor 205 may provides a signal or a change in state to the control electronics 414. For example, as previously discussed, the sensor 205 or electronics associated with the sensor 205 may provide such a signal or a change in state upon detecting an interactive element, for example, in a case where the first part 401 and the second part 402 are in proper alignment and sufficiently close in proximity to connect for operation. In other words, the drive device 44 may be inoperable unless the first part 401 and the second part 402 are operatively engaged properly (i.e., aligned properly).

In some embodiments, the control electronics 414 may provide a detect signal such as, but not limited to an electronic signal, flag setting, or other indicator to the control electronics 52 and/or the drive device 44 upon activation of the responsive device 410 by the interactive element 412. In such embodiments, the control electronics 52 and/or the drive device 44 may be configured to allow operation of the drive device 44 only upon the presence of the detect signal.

As discussed above, in certain embodiments, multiple responsive devices 410 and interactive elements 412 (and/or first interactive element(s) 404, second interactive element(s) 406, sensor(s) 405) may be provided on the first part 401 and the second part 402 and electronically connected to the control electronics 414. In such embodiments, the multiple responsive devices 410 and interactive elements 412 may be located, for example, at different respective positions around or within the first part 401 and the second part 402 to provide multiple alignment readings from different locations. In such embodiments, for instance, the control electronics 414 may be configured to provide a detect signal, for example, to allow operation of the drive device 44 only upon an activation of all or a predefined number or set of the responsive devices 410.

In further embodiments, the control electronics 414 may be configured to provide a detect signal, for example, to allow operation of the drive device 44 only upon an activation of all or a predefined number or set of the responsive devices 410 in a particular order. For example, the control electronics 414 may be configured to provide a detect signal only if a first responsive device is activated before, after, or simultaneously with a second responsive device. In the embodiments exemplified in FIGS. 29A and 29B, first, the first part 401 and the second part 402 may be connected so that the interactive element 412 aligns, activates, or otherwise interacts with a first responsive device 410 as shown in FIG. 29A. Then the first part 401 may be moved relative to the second part 402 to align the interactive element 412 with a second responsive device 410' shown in FIG. 29B. Such embodiments may allow, for example, for connection of components in a particular sequence, orientation, and/or in a particular direction.

With reference to FIGS. 24-29B, the control electronics 414 and/or the control electronics 52 (e.g., FIG. 4) may be configured to control the drive device 44 (e.g., FIG. 4) in various manners in accordance with various embodiments of the invention. For example, the drive device 44 may be controlled to stop pumping (delivery) operation upon a detection of an interruption of a fluid-flow path or a disconnection of a critical component in the delivery device 400. These may include, but are not limited to, a disconnection of a housing portion from another housing portion or from a base portion, a disconnection of a conduit from another conduit or from a reservoir, a disconnection of a reservoir from a housing portion or a base, and/or the like.

In alternative or in addition, the control electronics 414 and/or the control electronics 52 (e.g., FIG. 4) may be configured to detect a first-time connection of the first part 401 and the second 402 or a first-time connection of other components, as compared to a re-connection after previous or partial usage. In this manner, the drive device 44 may be controlled to provide a priming operation or other suitable first-time operation(s) upon detection of a first-time connection of the first part 401 and the second part 402.

In yet further embodiments, additional sensors and/or responsive devices 410a-410n may be provided within the medical device system 400 and connected for electrical communication with the control electronics 414. Such additional sensors and/or responsive devices 410a-410n may comprise magnetically and/or electronically actuating switches, magnetic and/or electric field magnitude and direction sensors, inductive sensors, other proximity sensors, contact sensors, and/or the like for providing a detectable signal or change in a state upon proper connection of other components in the medical device system 400. In some embodiments, such additional sensors and/or responsive devices 410a-410n may be similar to the sensor 205 (or 305) (e.g., FIG. 16-23) previously described. Such proper connection of other components may comprise, for example, one or more of a proper connection of a reservoir into a housing portion or base, a proper connection of a conduit to a reservoir, a proper connection of two conduits together, a proper setting of a needle or cannula in an inserted state, a proper connection of a conduit to a cannula or needle, or a proper connection of other components of or to the medical device system 400.

Alternatively, or in addition, the additional sensors and/or responsive devices 410a-410n may include one or more flow detectors for detecting the occurrence or blockage of a fluid flow path in the infusion device. In such embodiments, the control electronics 414 may be configured to provide a detect signal, for example, to allow operation of the drive device 44 only upon an activation of all or a predefined number or set of the responsive devices 410 and a proper state of the additional sensors and/or responsive devices 410a-410n.

In alternative or in addition, the control electronics 414 and/or the control electronics 52 (e.g., FIG. 4) may be configured to provide a user-perceptible indication of a proper alignment and/or connection of the first part 401 and the second part 402 or of other components. These may include, but are not limited to, the connection of a reservoir to a housing portion 401 or the connection of an injection site module to one or both of the first part 401 and the second part 402, and/or the like. For example, upon detection of a proper alignment and/or connection of the first part 401 and the second part 402, the control electronics 414 or 52 may provide a suitable control signal to activate an indicator device 420, as shown in FIG. 33.

The indicator device 420 may operated by a processor 422. The processor 422 may be configured to execute various programs and/or to process various information, such as data received from one or more sensors, responsive devices, and/or other interactive elements. The processor 422, for example, may be configured to compare detected signals with thresholds and/or pre-stored values in memory 424.

With reference to FIGS. 24-29B and 33, the indicator device 420 may include, but is not limited to, an audible indicator, an optical indicator, a tactile indicator, combinations of one or more those indicators, and/or the like. For example, upon a proper alignment or connection of components as described above, an audible beeping sound or other suitable sound may be generated by a sound generating device in or associated with one or both of the first part 401 and the second part 402. For example, upon a proper alignment or connection of components as described above, a flashing light or other suitable visual indicator may be generated by an LED or other light source or a display device on or associated with one or both of the first part 401 and the second part 402. For example, upon a proper alignment or connection of components as described above, a vibration and/or the like may be generated by a vibration device and/or the like in or associated with one or both of the first part 401 and the second part 402.

In some embodiments, one or more signals may be communicated from a transmitter (not shown) in one of the first part 401 and the second part 402 to a remotely located communication device (not shown), such as, but not limited to, a hand-held controller, a computer, and/or the like. Accordingly, the transmitter may provide one or more of the above-noted user-perceptible indications to a user of the communication device. In some embodiments, a text or graphic message may be displayed on a display screen on one of the first part 401, the second part 402, and/or on the communication device as an indicator of a proper or improper alignment or connection of the first part 401 and the second part 402.

FIGS. 30A-32B illustrate a medical device system 500 according to various embodiments of the present intention. The medical device system 500 may include features similar or may be employed as an embodiment of the medical device system 100 (e.g., FIGS. 7-23, the medical device system 200 (e.g., FIGS. 16-19), the medical device system 300 (e.g., FIGS. 20-23), the medical device system 400 (e.g., FIGS. 24-29B and 33), and/or any of the other embodiments described throughout the disclosure. Although the medical device system 500 may include features similar or used with the embodiments of FIGS. 7-29B, it should be understood that the medical device system 500 may also include some or all of the same features and operate in a manner similar to that shown and described in the embodiments of FIGS. 1-6C. In addition, some or all of the features shown in FIGS. 1-29B may be combined in various ways and included in the embodiments shown in FIGS. 30A-32B. Likewise, it should be understood that any of the features of the embodiments of FIGS. 30A-32B may be combined or otherwise incorporated into any of the other embodiments of FIGS. 30A-32B as well as any other embodiment herein discussed.

The medical device system 500 may include, but is not limited to, a container or body 510 of the reservoir, a plunger head 520, a plunger arm 526, and a plunger arm casing 530. The reservoir body 510 may have an interior volume 515 for containing fluidic media. The reservoir body 510 may have a first port 514 for allowing fluidic media to flow into the interior volume 515 of the reservoir body 510. The reservoir body 510 may have a second port 516 for expelling fluidic media contained in the interior volume 515 of the reservoir body 510. In various embodiments, one of the first port 514 and the second port 516 of the reservoir body 510 may be for allowing fluidic media to flow into the interior volume 515 of the reservoir body 510 and for expelling fluidic media contained in the interior volume 515 of the reservoir body 510. In various embodiments, the reservoir body 510 may be made of various suitable materials, including, but not limited to, glass, plastic, TOPAS® polymer (or any other cyclic olefin copolymer (or polymer)), and/or the like. The reservoir body 510 may be of any suitable shape and/or size and may be adapted to hold any volume of fluidic media depending on needs of user-patients.

The plunger head 520 may be located within the reservoir body 510 and may be moveable in an axial direction of the reservoir body 510 to expand (e.g., FIG. 32A) or contract (e.g., FIG. 32B) the interior volume 515 of the reservoir body 510. The plunger head 520 may be advanced within the reservoir body 510 to expel fluidic media contained in the interior volume 515 of the reservoir body 510 out the second port 516 of the reservoir body 510. The plunger head 520 may be made of Bromobutyl rubber, silicone rubber, or any other suitable material and/or any derivative thereof. The plunger head 520 may have a front portion 522 and a rear portion 523.

The front portion 522 of the plunger head 520 may be in contact with fluidic media contained in the interior volume 515 of the reservoir body 510. In some embodiments, the front portion 522 of the plunger head 520 may comprise a material compatible with fluidic media contained in the interior volume 515 of the reservoir body 510. For example, in some embodiments where the interior volume 515 of the reservoir body 510 is for containing insulin, the front portion 522 of the plunger head 520 may comprise an insulin compatible material, such as, but not limited to, polyethylene, and/or the like.

The rear portion 523 of the plunger head 520 may be connected or connectable to an end of the plunger arm 526 in any suitable manner. For example, the rear portion 523 of the plunger head 520 may include an aperture (not shown) for receiving a tab (not shown) and/or the like of the plunger arm 526. The tab (not shown) may be snap-fit into the aperture (not shown) to connect the plunger arm 526 to the rear portion 523 of the plunger head 520. In various other embodiments, the plunger arm 526 may be connected to the plunger head 520 and/or the rear portion 523 of the plunger head 520 in any suitable manner, such as, but not limited to, an adhesive, friction fitting, laser welding, magnetic coupling, and/or the like.

The plunger arm 526 may be moveable in an axial direction within the plunger arm casing 530 and the reservoir body 510. The plunger arm 526 may be made of a material of suitable strength and durability such, but not limited to, plastic, metal, glass (e.g., tempered glass), and/or the like. In some embodiments, the plunger arm 526 may be made of the same material as the reservoir body 510. In some embodiments, the plunger arm 526 and the rear portion 523 of the plunger head 520 may be integral to one another. In other embodiments, the plunger arm 526 and the rear portion 523 of the plunger head 520 may be separate components.

The plunger arm 526 may include an engagement side 528 for operatively engaging a drive member 540, drive linkage, and/or the like that may be part of a drive device, such as the drive device 44 (e.g., FIG. 4). For example, the engagement side 528 of the plunger arm 526 and the drive member 540 may be complementing gears, complementing threaded members, and/or the like, that may operatively engage one another. The drive member 540 may be a drive screw, drive rack, and/or the like. The drive member 540 may be connected to a motor (not shown) to move the drive member 540 to cause the plunger arm 526 to move within the plunger arm casing 530 and the reservoir body 510. Accordingly, the plunger arm 520 may be moved within the reservoir body 510 to expand and contact the interior volume 515 of the reservoir body 510.

The plunger arm casing 530 may be for supporting the plunger arm 526 as the plunger arm 526 is moved along the plunger arm casing 530. At least one side of the plunger arm 526 may be in contact with one or more interior sides of the plunger arm casing 530. In some embodiments, the plunger arm casing 530 may be for aligning or otherwise guiding the plunger arm 526, for example, into the reservoir body 510 as the plunger arm 526 moves along the reservoir body 510, for example, by the drive member 540. The plunger arm casing 530 may be made of a material of suitable strength and durability such, but not limited to, plastic, metal, glass (e.g., tempered glass), and/or the like. In some embodiments, the plunger arm casing 530 may be made of the same material as the reservoir body 510 and/or the plunger arm 526.

In various embodiments, the plunger arm casing 530 may be sized and configured to substantially envelop the plunger arm 526, for example in a case where the plunger head 520 is drawn substantially near the back end of the reservoir body 510 (e.g., FIG. 7A). Thus in some embodiments, the plunger arm 526 may be located within the reservoir body 510 and/or the plunger arm casing 530 during use of the reservoir system 500 by the user-patient (e.g., during delivery of fluidic media to the user-patient). In some embodiments, the plunger arm casing 530 may be part of the first part 501 or the second part 502. In other embodiments, the plunger arm casing 530 may be omitted or configured to envelop other components, in addition to or in alternative to, the plunger arm 526, such as the drive member 540, the motor, and/or the like.

In some embodiments, the plunger arm casing 530 may have an opening 536 for allowing a portion of the engagement side 528 of the plunger arm 526 to operatively engage the drive member 540. In such embodiments, the plunger arm 526 may be surrounded by the plunger arm casing 530 and/or the reservoir body 510. Accordingly in such embodiments, only the portion of the engagement side 528 of the plunger arm 526 exposed by the opening 536 free from (i.e., not surrounded by) the plunger arm casing 530 and/or the reservoir body 510. This may allow the drive member 540 to operatively engage the engagement side 528 of the plunger arm 526 while the plunger arm 526 or a portion thereof remains in the plunger arm casing 530 and/or the reservoir body 510.

The reservoir system 500 may include a reservoir cover (or casing) 534 that may be sized and configured to cover an end 517 of the reservoir body 510. For example, in a case where the first port 514 and the second port 516 is located on a first end of the reservoir body 510, a second end opposite the first end may be the end 517 of the reservoir body 510 covered by the reservoir cover 534. The reservoir cover 534 may be made of a material of suitable strength and durability such, but not limited to, plastic, metal, glass (e.g., tempered glass), and/or the like. In some embodiments, the reservoir cover 534 may be made of the same material as the plunger arm casing 530 and/or the reservoir body 510.

The reservoir cover 534 may be integral with the plunger arm casing 530. In other embodiments, the reservoir cover 534 may be separate from the plunger arm casing 530. For example, the reservoir cover 534 may be removably attachable to the plunger arm casing 530. In such embodiments, the reservoir cover 534 may be connected to or connectable to the plunger arm casing 530 in any suitable manner, such as those previously described.

In some embodiments, the end 517 of the reservoir body 510 may be open. The reservoir cover 534 may cover the open end 517 of the reservoir body 510 or be configured to fit within the open end 517 of the reservoir body 510 to seal or close the open end 517 of the reservoir body 510. The open end 517 may allow the plunger head 520 and/or at least a portion of the plunger arm 526 attached to the plunger head 520 to be insertable into the reservoir body 510, for example, before the reservoir cover 534 is placed in/on the reservoir body 510 to cover the open end 517.

In some embodiments, the reservoir cover 534 and/or the plunger arm casing 530 may be configured for minimizing an expansion of the reservoir body 510. In such embodiments, by fitting the reservoir cover 534 to the back of the reservoir body 510 in one or more dimensions, the reservoir cover 534 may help to retain a shape of the reservoir body 510.

A seal member 524, such as an o-ring and/or the like, may be positioned between the reservoir body 510 and a portion of the plunger head 520. The seal member 524 may be made of silicone, rubber, or any other suitable material for substantially preventing fluid from flowing between the reservoir body 510 and the plunger head 520. The interior volume 515 of the reservoir body 510 may be on one side of the seal member 524. The reservoir body 510 may have a chamber 552 located on an opposite side of the seal member 524 from the interior volume 515 of the reservoir body 510.

The seal member 524 may be for substantially preventing fluidic media from flowing from the interior volume 515 of the reservoir body 510 to the chamber 552 of the reservoir body 510. The chamber 552 of the reservoir body 510 may be located between the seal member 524 and the reservoir cover 534 in a case where the plunger head 520 is in the reservoir body 510 and the reservoir cover 534 and/or the plunger arm casing 530 are fitted or otherwise attached to the reservoir body 510. In some embodiments, the seal member 524 may be located between the front portion 522 and the rear portion 523 of the plunger head 520.

In some embodiments, the reservoir system 500 may include at least one support flange 527 positioned on the plunger arm 526 and the rear portion 523 of the plunger head 520. The support flange 527 may provide additional structural strength to the plunger arm 526 and/or the plunger head 520. For example, the support flange 527 may have a triangular configuration and be positioned with one side of the support flange 527 connected to a top surface of the plunger arm 526 and a second side of the support flange 527 connected to the rear portion 523 of the plunger head 520.

In addition to or alternative to, a second support flange (not shown) may be positioned with one side of the second support flange (not shown) connected to a side surface of the plunger arm 526 and a second side of the second support flange (not shown) connected to the rear portion 523 of the plunger head 520. One or both of the support flanges may be made of a material of suitable strength and durability such, but not limited to, plastic, metal, glass (e.g., tempered glass), and/or the like. In some embodiments, the one or both of the support flanges may be made of the same material as the plunger arm casing 530, the reservoir cover 534, and/or the reservoir body 510.

In some embodiments, such as the embodiments exemplified in FIGS. 30A and 30B, the first part 501 may include a first interactive element 504 adapted and/or configured to be moveable relative to the second part 502 to interact with at least one interactive element on the second part 502. The first interactive element 504 may be or be similar to, but is not limited to, the first interactive element, the second interactive element, the conductive medium, the sensor, and/or the like as previously described with respect to FIGS. 7-29B. For example, the first interactive element 504 may be, but is not limited to, one or more of the first interactive element 104 (204, 304, or 404), the first interactive element 104' (204', 304', or 404'), the second interactive element 106 (206, 306, or 406), the second interactive element 106' (206', 306', or 406'), the conductive medium 108 (208, 308, or 408), the sensor 205 (305, or 405), and/or the like.

Returning to FIGS. 30A and 30B, the first interactive element 504 may be arranged along a suitable moveable portion of the first part 501 (or any other part), such as, but not limited to, the plunger head 520 and/or the plunger arm 526. The first interactive element 504 may be configured to interact with a second interactive element 506, which may be or be similar, but is not limited to, the first interactive element, the second interactive element, the conductive medium, the sensor, and/or the like as previously described with respect to FIGS. 7-29B in a manner previously described to provide proper alignment of the first part 501 and the second part 502. For example, the second interactive element 506 may be, but is not limited to, one or more of the first interactive element 104 (204, 304, or 404), the first interactive element 104' (204', 304', or 404'), the second interactive element 106 (206, 306, or 406), the second interactive element 106' (206', 306', or 406'), the conductive medium 108 (208, 308, or 408), the sensor 205 (305, or 405), and/or the like.

Returning to FIGS. 30A and 30B, the first interactive element 504 may be further configured for interacting with a third interactive element 507, for example after proper alignment of the first part 501 and the second part 502. The third interactive element 507 may be or be similar to, but is not limited to, the first interactive element, the second interactive element, the conductive medium, the sensor, and/or the like as previously described with respect to FIGS. 7-29B. For example, the third interactive element 507 may be, but is not limited to, one or more of the first interactive element 104 (204, 304, or 404), the first interactive element 104' (204', 304', or 404'), the second interactive element 106 (206, 306, or 406), the second interactive element 106' (206', 306', or 406'), the conductive medium 108 (208, 308, or 408), the sensor 205 (305, or 405), and/or the like. In other embodiments, the third interactive element 507 of FIGS. 30A and 30B may be from the first interactive element, the second interactive element, the conductive medium, the sensor, and/or or the like as previously described with respect to FIGS. 7-29B.

Returning to FIGS. 30A and 30B, in some embodiments, the first interactive element 504 may be for interacting with the third interactive element 507 in a case where the first part 501 and the second part 502 have been operatively engaged properly and the first interactive element 504 and the third interactive element 507 are moved relative to each other (e.g., the medical device system 500 is primed). That is, the first interactive element 504 is moved relative to the third interactive element 507 or the third interactive element 507 is moved relative to the first interactive element 504.

In particular embodiments, the first interactive element 504 (or any other interactive element) may be (or associated with) a linear sensor. The linear sensor, for example, may be configured to sense a linear position of another component, such as, but not limited to, the second interactive element 506, the plunger head 520, or the like.

According to various embodiments, a signal may be provided to the drive device 44 (FIG. 4), and/or the like, for example from the responsive device 410 (e.g., FIGS. 24-29B and 33) or other suitable electronics, upon the first interactive element 504 interacting with the second interactive element 506 indicating proper alignment of the first part 501 and the second part 502. Accordingly, the drive device 44 may then prime the reservoir body 510 for use, for example, by moving the plunger head 520 to allow the first interactive element 504 to interact with the third interactive element 507. Thus in various embodiments, a first interactive element 504 may first interact with a second interactive element 506 to determine whether the first part 501 and the second part 502 have been operatively engaged properly. The first interactive element 504 then may interact with a third interactive element 507, for example by being moved relative to the third interactive element 507 or having the third interactive element 507 moved relative to the first interactive element 504.

In other embodiments, a user-perceptible indication may be provided as previously described to inform the user to prime manually the medical device system 500. For example, the medical device system 500 may include an interface for allowing the user to have the medical device system 500 primed.

In some embodiments, the third interactive element 507 may extend along a portion of the second part 502. Accordingly, the first interactive element 504 and the third interactive element 507 may be moveable relative to each other, for example, as the plunger head 520 and plunger arm 526 moves along the reservoir body 510. A position of the first interactive element 504 relative to the third interactive element 507 may allow for providing information relating to the reservoir system 500. For instance, a position of the first interactive element 504 relative to the third interactive element 507 may correspond to, but is not limited to, an amount of fluidic media delivered from the reservoir body 510, an amount of fluidic media remaining in the reservoir 510, pressure within the reservoir body 510, occlusion detection within the reservoir 510 and/or the delivery device 500, and/or a distance traveled by the plunger head 520, the plunger arm 526, and/or the interactive element 512, and/or the like.

In other embodiments, the third interactive element 507 (and/or the second interactive element 506) may be movable relative to the first interactive element 504. In particular embodiments, the third interactive element 507 (and/or the second interactive element 506) may be arranged along a suitable moveable portion of the second part 502 (or any other part). For example, the third interactive element 507 may be arranged on the plunger arm 526 for movement with the plunger arm 526 relative to the first interactive element 504 that may be arranged, for example in the plunger arm casing 530, the reservoir body 510, and/or the like.

In some embodiments, the third interactive element 507 may be the same interactive element used to align the first part 501 and the second part 502. In such embodiments, the third interactive element 507 may replace or be used in addition to the second interactive element 506. Furthermore, in such embodiments, the part (e.g., plunger head 520, plunger arm 526, etc.) supporting the first interactive element 504 may or may not be moved relative to the third interactive element 507 to prime the reservoir system 500.

In some embodiments, the third interactive element 507 may have generally the same magnitude of strength across the third interactive element 507. In other embodiments, portions of the third interactive element 507 may have different magnitudes of strength.

In some embodiments, at least one of the first interactive element 504, the second interactive element 506, and the third interactive element 507 may be arranged in a bias configuration or with a bias mechanism in a manner previously described (e.g., FIGS. 14A and 14B). For example, the first interactive element 504 may be biased toward an expanded state to allow the first interactive element 504 to press upon or otherwise contact the second interactive element 506 and/or the third interactive element 507.

In some embodiments, such as the embodiment exemplified in FIG. 31, at least one of the second interactive element 506 and the third interactive element 507 may have a flexible layer 509 that may be pressed upon by the first interactive element 504 (or by a portion of the opposing part (e.g., first part 501)). As shown, a portion of the flexible layer 509 pressed by the first interactive element 504 may correspond to a portion of the flexible layer 509 (e.g., on an opposite surface) that contacts the third interactive element 507. Accordingly, the portion that contacts the third interactive element 507 may correspond to a relative position of the first interactive element 504 to the third interactive element 507 as previously described, for example, with respect to FIGS. 30A and 30B. Returning to FIG. 31, in other embodiments, the second interactive element 506 and/or the third interactive element 507 may be a flexible layer—as opposed to including such a layer—for contacting another interactive element, layer, and/or the like, in a manner described above.

The flexible layer 509 may be selected or otherwise configured to be a conductor between the first interactive element 504, the second interactive element 506, and/or the third interactive element 507. For example, the flexible layer 509 may be like the conductive medium 108 (208, 308, or 408) (e.g., FIGS. 7-29B). Thus in some embodiments, the flexible layer 509 may be a conductive medium, such as an electrically conductive layer (e.g., metal), ferrous conduit, and/or the like. In other embodiments, the flexible layer 509 may be selected or otherwise configured to be a conductor with one or more of the interactive elements and a nonconductor with one or more of the interactive elements. For example, the flexible layer 509 may be a conductor with the second interactive element 506 and/or the third interactive element 507, but not the first interactive element 504. In such embodiments, for example, the first interactive element 504 may be a finger, pusher, and/or the like for pressing upon the flexible layer 509. In other embodiments, the flexible layer 509 may be a film made of a suitable flexible material, including, but not limited to, Mylar and/or the like. In some embodiments, the flexible layer may be nonconductive. In such embodiments, for example, at least one of the interactive elements may be a finger, pusher, and/or the like for applying a force or the like to the flexible layer 509 that may be detectable by the third interactive element 507 (e.g., a force and/or pressure sensor).

In some embodiments, the flexible layer 509 may be arranged to be substantially still, for example in the plunger arm casing 530, and the first interactive element 504 may be arranged to be movable relative to the flexible layer 509, for example, with movement of the plunger arm, plunger head, and/or the like. In other embodiments, the flexible layer 509 may be arranged to be movable relative to the first interactive element 504, for example, with movement of the plunger arm, the plunger head, and/or the like, and the first interactive element 504 may be arranged to be substantially still, for example in the plunger arm casing 530.

In other embodiments, such as the embodiments exemplified in FIGS. 32A and 32B, the third interactive element 507 may comprise a plurality of third interactive elements 507a-507n arranged along a portion of the second part 502 (or the first part 501). The plurality of third interactive elements 507a-507n may be in contact with, adjacent to (with or without a material in between), and/or spaced apart (with or without a material in between) from each other.

An interactive element of the plurality of third interactive elements 507a-507n interacting with the first interactive element 504 may provide similar information as previously described with respect to FIGS. 30A-31. For instance, returning to 32A and 32B, each of the plurality of third interactive elements 507a-507n may be arranged to correspond to a certain amount of fluidic media delivered (e.g., 0.1 ml), amount of fluidic media remaining, distance traveled by the plunger head 520, and/or the like. For example in one embodiment, movement of the first interactive element 504 relative to the plurality of third interactive elements 507a-507n a certain number of interactive elements of the plurality of third interactive elements 507a-507n may correspond to a certain volume of fluidic media having been delivered. Similarly, movement of the first interactive element 504 relative to the plurality of third interactive elements 507a-507n a certain number of interactive elements of the plurality of third interactive elements 507a-507n may correspond to a certain volume of fluidic media remaining in the reservoir 510.

In some embodiments, each of the plurality of third interactive elements 507a-507n may have the same magnitude of strength. For example, in a case where the third interactive elements 507a-507n are magnets, some or each of the plurality of third interactive elements 507a-507n may have the same magnetic strength and/or provide similar magnetic fields. In other embodiments, some or each of the plurality of third interactive elements 507a-507n may have different magnitudes of strength. In some embodiments where the plurality of third interactive elements 507a-507n are magnets, each of the plurality of the third interactive elements 507a-507n may have the same polarity, while in other embodiments, each of the plurality of third interactive elements 507a-507n may have different polarities.

In some embodiments, one or more of the plurality of third interactive elements 507a-507n may be the same interactive element used to align the first part 501 and the second part 502. In such embodiments, the third interactive element 507 may replace or be used in addition to the second interactive element 506. Furthermore, in such embodiments, the part (e.g., plunger head 520, plunger arm 526, etc.) supporting the first interactive element 504 may or may not be moved relative to the third interactive element 507 to prime the reservoir system 500.

With reference to FIGS. 30A-32B, in various embodiments, the arrangement of each of the interactive elements (e.g., first interactive element 504, second interactive element 506, third interactive element 507 need not be limited to the exemplified arrangements. The various interactive elements may be arranged as needed in any suitable configuration amongst some or all of the components (e.g., first part 101, second part 102, and/or the like) as well as other components (e.g., further parts, such as an needle-inserting device as discussed, electronics housing, and/or the like). As a non-limiting example, in FIG. 32B, the first interactive element 504 may comprise a plurality of first interactive elements arranged along a portion of the first part 501 (or the second part 501) in addition to or in place of a plurality of third interactive elements 507a-507n on the second part 502. As another non-limiting example, with reference to FIGS. 31-32B, the flexible layer 509 may be arranged over a plurality of third interactive elements 507a-507n such that the flexible layer 509 may contact at least one of the interactive elements of the plurality of third interactive elements 507a-507n, for example, upon being pressed upon by the first interactive element 504.

With reference to FIGS. 7-30B, while particular embodiments of the present invention have been shown and described, it will be apparent to those skilled in the art that the invention is not limited to the particular embodiments shown and described and that changes and modifications may be made without departing from the spirit and scope of the claimed invention. For example, while embodiments described above may include an adhesive material and a cover film 23 (FIGS. 2 and 3), further embodiments may include a plurality of adhesive material layers alternating with a corresponding plurality of cover film layers 23 to allow the delivery device to be secured, removed and re-secured to the skin of the patient-user one or more times.

In such embodiments, a first cover film layer located at the end of the stack of alternating layers of adhesive material and cover film may be removed to expose a first layer of adhesive material. With the first layer of adhesive material exposed, a medical device system (e.g., 100) (or component thereof) may be adhered to skin of a patient-user, as previously described. After a suitable period of usage, the medical device system (or component having the adhesive) may be removed from the skin of the patient-user, for example, for servicing, re-filling, replacement of one or more components, or the like. After removal of the medical device system (or component) from the skin of the patient-user, a second cover film layer on the medical device system (or component) may be removed to expose a second layer of adhesive material. With the second layer of adhesive material exposed, the medical device system (or component) may be secured to the same patient-user or, in certain contexts, to a different patient-user, for further operation. The process may be repeated a number of times up to the number of adhesive material and cover film layer pairs are included in the plural alternating layers of adhesive material and cover film.

In addition, while various embodiments described above may include one or more adhesive layers, each having a peelable cover layer, other embodiments may employ a single adhesive layer having (or plural adhesive layers, each having) a pattern of plural peelable cover layer portions. Accordingly, a patient-user may peel off one portion of the cover layer for adhering a medical device system (e.g., 100) to the patient-user as described above, while leaving the rest of the pattern of peelable cover layer portions on the adhesive. In such an embodiment, after completion of a first period of operation of the medical device system and removal of the medical device system from the patient-user, a second portion of the peelable cover layer may be removed from the adhesive layer and the medical device system may be adhered to the same patient-user or, in certain contents, to a different patient-user for a second period of operation.

In various embodiments, while various medical device system (e.g., 100) embodiments described above may include base portions (e.g., 21 in FIGS. 1-6C) that are configured to be secured to skin of a patient-user (or other suitable surface of operation) and that extend along a length and/or width of the medical device system structure, other embodiments may employ base portions configured to be secured to the skin of the patient-user (or other surface) and extend less than a full length or width dimension of the medical device system structure to minimize surface area in contact with the patient-user (or other surface). Such embodiments may increase comfort of the patient-user during operation of the medical device system. Base portions having shapes and sizes different from those shown in the accompanying drawings may be employed for additional improvements with regard to the comfort of the patient-user and/or minimizing the surface area in contact with the patient-user. Furthermore, as noted above, the base portion may be composed of a flexible material that at least partially conforms to the curvature and movement of a body of the patient-user.

In any of the above-described embodiments in which an adhesive material is used to secure one or more medical device system (e.g., 100) components to skin of a patient-user (or other suitable surface), multiple types of adhesive materials (or multiple strengths of adhesives) may be employed, such that a stronger adhesive may be provided in certain areas (e.g., around the needle injection site), while a weaker adhesive may be provided in other areas. Examples of various adhesive systems may be found in, but are not limited to, U.S. application Ser. No. 12/027,963, filed Feb. 7, 2008, entitled "Adhesive Patch Systems and Methods," herein incorporated by reference in its entirety.

The embodiments disclosed herein are to be considered in all respects as illustrative, and not restrictive of the invention. The present invention is in no way limited to the embodiments described above. Various modifications and changes may be made to the embodiments without departing from the spirit and scope of the invention. The scope of the invention is indicated by the attached claims, rather than the embodiments. Various modifications and changes that come within the meaning and range of equivalency of the claims are intended to be within the scope of the invention.

What is claimed is:

1. A delivery system for delivering fluidic media to a user, the delivery system comprising:
    a first housing portion adapted to be carried by a user;
    a second housing portion configured to be selectively operatively engaged with and disengaged from the first housing portion, one of the first housing portion and the second housing portion supporting a reservoir having an interior volume for containing fluidic media and a plunger head moveable within the interior volume of the reservoir along an axial direction of the reservoir;
    a drive device supported by the other of the first housing portion and the second housing portion relative to the one of the first housing portion and the second housing portion supporting the reservoir such that upon the first housing portion and the second housing portion being operatively engaged, the reservoir is operatively coupled to the drive device;
    a pair of interactive elements including a first interactive element supported on the first housing portion and a second interactive element supported on the second housing portion at a location to be interactable with the first interactive element; and
    circuitry configured to detect an interaction between the first interactive element and the second interactive element, the interaction having a state of a plurality of states;
    the circuitry configured to determine the state of the interaction;
    the circuitry configured to provide a signal from a plurality of signals, the plurality of signals corresponding to the plurality of states; and
    the circuitry configured to, in response to the first housing portion and the second housing portion being operatively engaged and the interaction between the first interactive element and the second interactive element being detected, provide the signal corresponding to the state of the interaction.

2. The delivery system of claim 1, the first interactive element and the second interactive element configured to be interactable with each other in a case where the first housing portion and the second housing portion are positioned relative to each other in a predetermined manner.

3. The delivery system of claim 2, wherein the first housing portion and the second housing portion are positioned relative to each other in the predetermined manner in a case where the first housing portion and the second housing portion are aligned in more than one dimension.

4. The delivery system of claim 2, wherein the first housing portion and the second housing portion are positioned relative to each other in the predetermined manner in a case where the first interactive element and the second interactive element are sufficiently proximate to each other.

5. The delivery system of claim 1, the first interactive element and the second interactive element configured to be interactable with each other in a case where the first housing portion and the second housing portion are and the first interactive element and the second interactive element are sufficiently proximate to each other.

6. The delivery system of claim 5, wherein the first interactive element and the second interactive element are sufficiently proximate to each other in a case where the first interactive element and the second interactive element contact each other.

7. The delivery system of claim 1, the delivery system further comprising:
    a user-perceptible indicator operatively connected to the circuitry, the user-perceptible indicator for providing a user-perceptible indication in response to the signal provided by the circuitry in a case where the first housing portion and the second housing portion are operatively engaged and the interaction between the first interactive element and the second interactive element is detected.

8. The delivery system of claim 7, wherein the user-perceptible indication comprises at least one of an audible indication, a visual indication, and a tactile indication.

9. The delivery system of claim 1, the first interactive element and the second interactive element configured to be electronically interactable with each other.

10. The delivery system of claim 1,
    wherein one of the first interactive element and the second interactive element comprises an electrical contact and the other of the first interactive element and the second interactive element comprises an electrically conductive material; and
    the circuitry configured to detect the interaction in a case where the first housing portion and the second housing portion are operatively engaged and the electrical contact contacts the electrically conductive material.

11. The delivery system of claim 10, wherein one of the electrical contact and the electrically conductive material comprise at least one of a spring and a protrusion adapted to contact the other of the electrical contact and the electrically conductive material upon the first housing portion and the second housing portion being operatively engaged.

12. The delivery system of claim 1, the delivery system further comprising:
    control electronics operatively connected to the circuitry for controlling the drive device to drive fluid from the reservoir based upon the signal provided by the circuitry.

13. The delivery system of claim 12, the control electronics configured to inhibit operation of the drive device unless the signal provided by the circuitry corresponds to the state for an interaction determined when the first housing portion and the second housing portion are operatively engaged and the interaction between the first interactive element and the second interactive element is detected.

14. The delivery system of claim 12, the control electronics configured to change from a first power state to a second power state in a case where the first housing portion and the second housing portion are operatively engaged and the interaction between the first interactive element and the second interactive element is detected.

15. The delivery system of claim 1,
at least one of the first interactive element and the second interactive element arranged on a movable portion of at least one of the reservoir and the drive device;
wherein a position of the first interactive element relative to the second interactive element corresponds to reservoir data.

16. The delivery system of claim 1,
at least one of the first interactive element and the second interactive element configured to be moveable relative to the other of the first interactive element and the second interactive element;
wherein a position of the first interactive element relative to the second interactive element corresponds to reservoir data.

17. The delivery system of claim 16, wherein the reservoir data includes data relating to a volume of fluidic media in the reservoir.

18. The delivery system of claim 16,
the drive device comprising at least one of a plunger head for driving fluid out from the reservoir and a plunger arm operatively connected to the plunger head for moving the plunger head; and
the at least one of the first interactive element and the second interactive element supported on at least one of the plunger head and the plunger arm.

19. The delivery system of claim 16, wherein at least one of the first interactive element and the second interactive element comprise a linear sensor.

20. The delivery system of claim 19, wherein the linear sensor is configured to sense a linear position.

21. The delivery system of claim 16, wherein at least one of the first interactive element and the second interactive element comprise one of a linear conductor and a linear resistor.

22. The delivery system of claim 1,
at least one of the first interactive element and the second interactive element configured to be moveable relative to the other of the first interactive element and the second interactive element;
at least one of the first interactive element and the second interactive element comprising a plurality of conductors;
wherein a position of the other of the first interactive element and the second interactive element relative to one of the plurality of conductors corresponds to reservoir data.

23. The delivery system of claim 1, the delivery system further comprising:
a second pair of interactive elements including a third interactive element supported on the first housing portion and a fourth interactive element supported on the second housing portion at a location to be interactable with the third interactive element;
the circuitry configured to detect an interaction between the third interactive element and the fourth interactive element, the circuitry configured to provide a signal in response to the first housing portion and the second housing portion being operatively engaged and an interaction between the third interactive element and the fourth interactive element being detected.

24. The delivery system of claim 23,
at least one of the third interactive element and the fourth interactive element configured to be moveable relative to the other of the first interactive element and the second interactive element.

25. The delivery system of claim 24, wherein a position of the third interactive element relative to the fourth interactive element corresponds to reservoir data.

26. The delivery system of claim 24,
the drive device comprising at least one of a plunger head for driving fluid out from the reservoir and a plunger arm operatively connected to the plunger head for moving the plunger head; and
the at least one of the third interactive element and the fourth interactive element supported on at least one of the plunger head and the plunger arm.

27. The delivery system of claim 24, wherein at least one of the third interactive element and the fourth interactive element comprise a linear sensor.

28. The delivery system of claim 27, wherein the linear sensor is configured to sense a linear position.

29. The delivery system of claim 1, at least one of the first interactive element and the second interactive element adapted to be insert mold labeled to the first housing portion and the second housing portion respectively.

30. The delivery system of claim 1, the delivery system further comprising:
a film cover for supporting at least one of the first interactive element and the second interactive element on the first housing portion and the second housing portion respectively.

31. The delivery system of claim 1, the delivery system further comprising:
a reservoir supported by one of the first housing portion and the second housing portion, the reservoir having an interior volume for containing fluidic media.

32. The delivery system of claim 1, wherein the one of the first housing portion and the second portion comprises a reservoir supported by one of the first housing portion and the second housing portion, the reservoir having an interior volume for containing fluidic media.

33. The delivery system of claim 1, the circuitry comprising a responsive device configured to provide the signal in response to the first housing portion and the second housing portion being operatively engaged and the interaction between the first interactive element and the second interactive element being detected.

34. The delivery system of claim 1, the delivery system further comprising a bias mechanism for biasing at least one of the first interactive element and the second interactive element toward each other.

35. The delivery system of claim 1, one of the first interactive element and the second interactive element comprising a flexible conductive membrane, the other of the first interactive element and the second interactive element configured to press against the flexible conductive membrane upon the first housing portion and the second housing portion being operatively engaged.

36. The delivery system of claim 1,
wherein the first interactive element comprises a detectable feature;
wherein the second interactive element comprises a sensor configured to sense the detectable feature;
the circuitry configured to provide the signal in a case where the first housing portion and the second housing portion are operatively engaged and the detectable feature is detected by the sensor.

37. The delivery system of claim 36, at least one of the sensor and the detectable feature comprising at least one of a linear resistor and a discrete contact switch.

38. The delivery system of claim 36, wherein the detectable feature comprises at least one of a coded resistor pattern, an electrical contact, an electromechanical switch.

39. The delivery system of claim 36, wherein the sensor comprises an optical sensor.

40. The delivery system of claim 39, wherein the optical sensor comprises at least one of a color detector and a gray-scale detector.

41. The delivery system of claim 39,
wherein the optical sensor comprises a bar code reader; and
wherein the detectable feature comprises a bar code.

42. The delivery system of claim 36,
wherein the sensor comprises an ultrasonic sensor; and
wherein the detectable feature comprises an ultrasonic signature.

43. The delivery system of claim 36, wherein the detectable feature comprises a radio frequency identification device.

44. The delivery system of claim 1,
wherein one of the first interactive element and the second interactive element has a capacitance that is measurable;
wherein the other of the one of the first interactive element and the second interactive element is configured to affect the capacitance;
the circuitry configured to provide the signal in a case where the first housing portion and the second housing portion are operatively engaged and the capacitance is affected by the other of the one of the first interactive element and the second interactive element.

45. The delivery system of claim 1,
wherein one of the first interactive element and the second interactive element has an inductance that is measurable;
wherein the other of the one of the first interactive element and the second interactive element is configured to affect the inductance;
the circuitry configured to provide the signal in a case where the first housing portion and the second housing portion are operatively engaged and the inductance is affected by the other of the one of the first interactive element and the second interactive element.

46. The delivery system of claim 36,
wherein the sensor comprises at least one magnetic sensor; and
wherein the detectable feature comprises a magnetic material.

47. The delivery system of claim 36, wherein one of the sensor and the detectable feature comprises an occlusion sensor of the delivery system for sensing an occlusion in the reservoir.

48. A method of making a delivery system, the method comprising:
adapting a first housing portion to be carried by a user;
configuring a second housing portion to be selectively operatively engaged with and disengaged from the first housing portion, one of the first housing portion and the second housing portion supporting a reservoir having an interior volume for containing fluidic media and a plunger head moveable within the interior volume of the reservoir along an axial direction of the reservoir;
supporting a drive device on the other of the first housing portion and the second housing portion relative to the one of the first housing portion and the second housing portion supporting the reservoir such that upon the first housing portion and the second housing portion being operatively engaged, the reservoir is operatively coupled to the drive device;
supporting a pair of interactive elements including supporting a first interactive element on the first housing portion and supporting a second interactive element on the second housing portion at a location to be interactable with the first interactive element; and
configuring circuitry to detect an interaction between the first interactive element and the second interactive element, the interaction having a state of a plurality of states;
the circuitry configured to determine the state of the interaction;
the circuitry configured to provide a signal from a plurality of signals, the plurality of signals corresponding to the plurality of states; and
the circuitry configured to, in response to the first housing portion and the second housing portion being operatively engaged and an interaction between the first interactive element and the second interactive element being detected, provide the signal corresponding to the state.

\* \* \* \* \*